(12) United States Patent
Narimatsu et al.

(10) Patent No.: US 7,629,150 B2
(45) Date of Patent: Dec. 8, 2009

(54) TRANSFORMED CELL HARBORING DNA OR RNA ENCODING SUGAR CHAIN SYNTHESIZING AGENT HAVING β1,3-N-ACETYLGLUCOSAMINYLTRANSFERASE ACTIVITY

(75) Inventors: Hisashi Narimatsu, 5-1082-1, Mukouhara, Higashiyamato-shi, Tokyo (JP) 207-0013; Katsutoshi Sasaki, Machida (JP); Ayumi Natsume, Machida (JP); Hiroyuki Mio, Chiyoda-ku (JP); Satoshi Nakagawa, Machida (JP); Susumu Sekine, Machida (JP); Akira Togayachi, Higashikurume (JP)

(73) Assignees: Kyowa Hakko Kirin Co., Ltd., Tokyo (JP); Hisashi Narimatsu, Tokyo (JP)

( * ) Notice: Subject to any disclaimer, the term of this patent is extended or adjusted under 35 U.S.C. 154(b) by 0 days.

(21) Appl. No.: 11/837,804

(22) Filed: Aug. 13, 2007

(65) Prior Publication Data
US 2008/0050745 A1 Feb. 28, 2008

Related U.S. Application Data

(62) Division of application No. 10/363,145, filed as application No. PCT/JP01/07563 on Aug. 31, 2001, now Pat. No. 7,279,310.

(30) Foreign Application Priority Data
Sep. 1, 2000 (JP) ............................. 2000-265430

(51) Int. Cl.
| | |
|---|---|
| C12P 19/00 | (2006.01) |
| C12P 1/00 | (2006.01) |
| C12P 19/18 | (2006.01) |
| C12N 9/00 | (2006.01) |
| C12N 9/10 | (2006.01) |
| C12N 1/20 | (2006.01) |
| C12N 15/00 | (2006.01) |
| C07K 14/00 | (2006.01) |
| C07H 21/04 | (2006.01) |

(52) U.S. Cl. .............................. 435/72; 435/41; 435/97; 435/183; 435/252.3; 435/320.1; 530/350; 536/23.2

(58) Field of Classification Search .................. None
See application file for complete search history.

(56) References Cited

FOREIGN PATENT DOCUMENTS

| | | |
|---|---|---|
| JP | 6-181759 | 7/1994 |
| WO | WO 01/44479 | 6/2001 |
| WO | WO 02/04612 | 1/2002 |
| WO | WO 02/18556 | 3/2002 |

OTHER PUBLICATIONS

Chica et al. Curr Opin Biotechnol. Aug. 2005;16(4):378-84.*
Juengst. BMJ. Jun. 28, 2003;326(7404):1410-1.*
Sato, et al., "Molecular cloning of a human cDNA encoding β-1,4-galactosyltransferase with ...", Proc. Natl. Acad. Sci., vol. 95 (1998) 472-77.
Mattila, et al., The Centrally Acting β1,6-N-Acetylglucosaminyltransferase (GlcNAc to Gal), J. Biol. Chem., vol. 273, No. 42 (1998) 27633-39.
Zhou, et al., Accession AAD09763 (Aug. 9, 2000).
Zhou, et al., "A β-1,3-acetylglucosaminyltransferase with ...", Proc. Natl Acad. Sci. USA, vol. 96, No. 2 (1999) 406-11.
Van Cott, et al., "Transgenic pigs as bioreactors: a comparison of gamma-carboxylation of glutamic acid in recombinant human protein C and factor IX by the mammary gland", Genetic Analysis: Biomolecular Engineering, vol. 15, Nos. 3-5 (1999) 155-60.
Chaudhary, et al., "Transgenic *Brassica carinata* as a vehicle for the production of recombinant protein in seeds", Plant Cell Reports, vol. 17 (1998) 195-200.
Henion et al., Cloning of a Mouse β1,3 N-Acetylglucosaminyltransferase GlcNAc(β1,3)Gal(β1,4)Glc-ceramide Synthase Gene Encoding the Key Regulation of Lacto-series Glycolipid Biosynthesis, J. Biol. Chem., vol. 276, No. 32 (2001) 30261-69.

* cited by examiner

*Primary Examiner*—Christian L Fronda
(74) *Attorney, Agent, or Firm*—Fitzpatrick, Cella, Harper & Scinto

(57) ABSTRACT

The present invention provides a novel polypeptide having a β1,3-N-acetylglucosaminyltransferase activity, an agent for synthesizing a sugar chain comprising the polypeptide, a process for producing a sugar chain or a complex carbohydrate using the agent for synthesizing a sugar chain, DNA encoding the polypeptide, a process for producing the polypeptide, an antibody against the polypeptide, and a diagnosis method and a medicament for treatment for inflammation, cancer or tumor metastasis using the DNA or the antibody. The present invention is useful for synthesis of a useful sugar chain and diagnosis and treatment for inflammatory diseases, cancer or tumor metastasis.

5 Claims, 5 Drawing Sheets

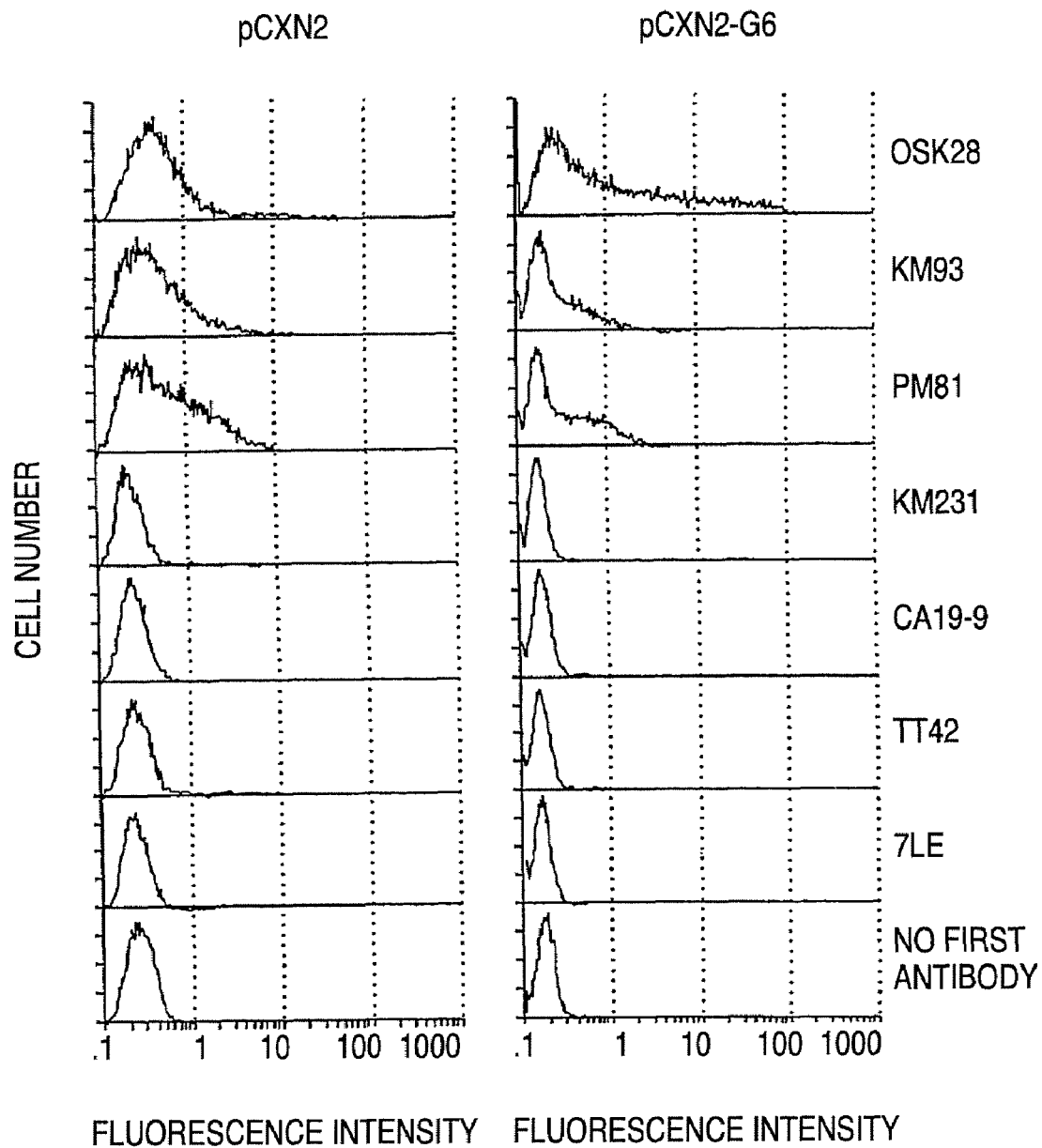

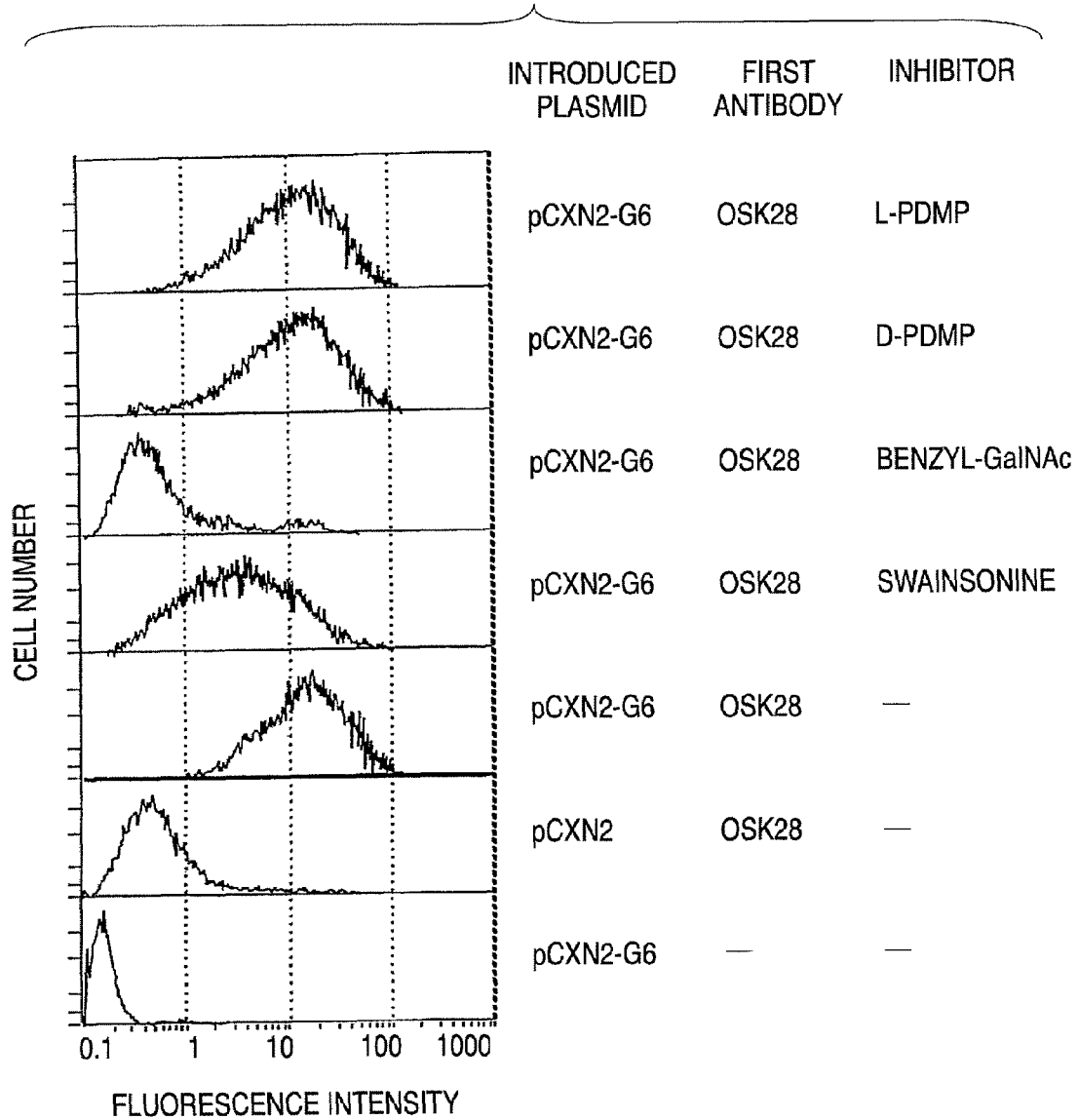

TRANSFORMED CELL HARBORING DNA OR RNA ENCODING SUGAR CHAIN SYNTHESIZING AGENT HAVING β1,3-N-ACETYLGLUCOSAMINYLTRANSFERASE ACTIVITY

This application is a divisional of application Ser. No. 10/363,145 filed Sep. 12, 2003, which in turn is a national stage of PCT application No. PCT/JP01/07563 filed Aug. 31, 2001.

TECHNICAL FIELD

The present invention relates to a novel polypeptide having a lactosylceramide β1,3-N-acetylglucosaminyltransferase activity and a paragloboside β1,3-N-acetylglucosaminyltransferase activity; an agent for synthesizing a sugar chain, which comprises the polypeptide as an active ingredient; a DNA encoding the polypeptide, an agent for detecting inflammation, cancer or tumor metastasis, which comprises the DNA; a recombinant DNA obtainable by inserting the DNA into a vector; a transformant comprising the recombinant DNA; a process for producing the polypeptide using the transformant; a process for producing a sugar chain or complex carbohydrate using the polypeptide; a process for producing a sugar chain or complex carbohydrate using the transformant; a method for detecting inflammation, cancer or tumor metastasis using an oligonucleotide obtainable from a DNA encoding the polypeptide; an antibody which recognizes the polypeptide; a method for immunohistostaining using the antibody; an agent for immunohistostaining or an agent for diagnosing inflammatory disease, cancer or tumor metastasis, which comprises the antibody; a medicament comprising the polypeptide, the DNA, the recombinant vector or the antibody; a method for screening a compound which changes a lactosylceramide β1,3-N-acetylglucosaminyltransferase activity and a paragloboside β1,3-N-acetylglucosaminyltransferase activity of the polypeptide; a method for screening a compound which changes expression of the gene; a promoter DNA which controls transcription of the gene; a method for screening a compound which changes efficiency of transcription by the promoter DNA; a compound obtainable by the screening methods; a non-human knockout animal the gene is deleted or mutated; and the like.

BACKGROUND ART

Lactosylceramide β1,3-N-acetylglucosaminyltransferase is an enzyme having an activity to transfer N-acetylglucosamine via β1,3-linkage to a galactose residue present in the non-reducing terminal of lactosylceramide (Galβ1-4Glc-ceramide). Neolacto-series glycolipids, lacto-series glycolipids, ganglio-series glycolipids, globo-series glycolipids and isoglobo-series glycolipids are synthesized from the lactosylceramide (Galβ1-4Glc-ceramide), and lactosylceramide β1,3-N-acetylglucosaminyltransferase is a key enzyme of the synthesis of neolacto-series glycolipids and lacto-series glycolipids.

Ganglioside GM3 (NeuAcα2-3Galβ1-4Glc-ceramide) is synthesized when GM3 synthase acts upon lactosylceramide. AsialoGM2 (GalNAcβ1-4Galβ1-4Glc-ceramide) is synthesized when GM2 synthase acts upon lactosylceramide. Since many other gangliosides are synthesized from GM3 and asialoGM2, GM3 synthase and GM2 synthase can be regarded as key enzymes of the synthesis of ganglio-series glycolipids. On the other hand, when lactosylceramide α1,4-galactosyltransferase acts upon lactosylceramide, Galα1-4Galβ1-4Glc-ceramide is synthesized and then a series of globo-series glycolipids are synthesized. When lactosylceramide α-1,3-galactosyltransferase acts upon lactosylceramide, Galα1-3Galβ1-4Glc-ceramide is synthesized and then a series of isoglobo-series glycolipids are synthesized.

Accordingly, it can be said that lactosylceramide α1,4-galactosyltransferase and lactosylceramide α1,3-galactosyltransferase are key enzymes of the synthesis of globo-series glycolipids and isoglobo-series glycolipids, respectively. It is considered that synthesis of a specific glycolipid in a cell is controlled by the expression and expression level of the above key enzymes.

Neolacto-series glycolipid is a glycolipid having Galβ1-4GlcNAcβ1-3Galβ1-4Glc-ceramide backbone, and lacto-series glycolipid is a glycolipid having a Galβ1-3GlcNAcβ1-3Galβ1-4Glc-ceramide backbone. Examples of the neolacto-series glycolipid include paragloboside (Galβ1-4GlcNAcβ1-3Galβ1-4Glc-ceramide), sialylparagloboside (NeuAcα2-3Galβ1-4GlcNAcβ1-3Galβ1-4Glc-ceramide), NeuAcα2-3Galβ1-4(Fucα1-3)GlcNAcβ1-3Galβ1-4Glc-ceramide and the like. Examples of the lacto-series glycolipid include Galβ1-3GlcNAcβ1-3Galβ1-4Glc-ceramide, NeuAcα2-3Galβ1-3GlcNAcβ1-3Galβ1-4Glc-ceramide, NeuAcα2-3Galβ1-3(Fucα1-4)GlcNAcβ1-3Galβ1-4Glc-ceramide and the like.

It has been found that lacto- or neolacto-series glycolipids to which fucose and sialic acid are added are accumulated in large amounts in many human cancers (particularly colon cancer or gastric cancer) [*Annu. Rev. Immunol.*, 2, 103 (1984), *Chem. Phys. Lipids*, 42, 209 (1986)]. As a result of the measurement of glycosyltransferase activity in colon cancer tissues and their peripheral normal tissues or various colon cancer cell lines, it has been found that the activity of lactosylceramide β1,3-N-acetylglucosaminyltransferase is increased in colon cancer tissues and various colon cancer cell lines [*J. Biol. Chem.*, 262, 15649 (1987)]. This result suggests that increase of the lacto- or neolacto-series glycolipids in colon cancer is caused by the increased lactosylceramide β1,3-N-acetylglucosaminyltransferase activity.

When a human promyelocytic cell line, HL-60, is treated with dimethyl sulfoxide or retinoic acid, it differentiates into granulocyte cells. On the other hand, when HL-60 is treated with phorbol ester such as phorbol-12-myristate-13-acetate (PMA), it differentiates into monocyte/macrophage. While neolacto-series glycolipids (paragloboside and sialylparagloboside) increase and ganglioside GM3 decreases when it is differentiated into granulocyte cells, ganglioside GM3 increases and neolacto-series glycolipids decrease when it is differentiated into monocyte/macrophage. Also, when HL-60 is cultured by adding a neolacto-series glycolipid, it differentiates into granulocyte cells, and when HL-60 is cultured by adding ganglioside GM3, it differentiates into monocyte/macrophage. The results show that expression of a specific glycolipid is important in determining the induction and direction of the differentiation. When HL-60 is treated with retinoic acid, the GM3 synthase activity does not change but the lactosylceramide β1,3-N-acetylglucosaminyltransferase activity increases [*J. Biol. Chem.*, 267, 23507 (1992)]. Thus, it is considered that, in the HL-60 treated with retinoic acid, increase of neolacto-series glycolipids and decrease of ganglioside GM3 are induced caused by the increased lactosylceramide β1,3-N-acetylglucosaminyltransferase activity, and it differentiates into granulocyte cells as the result. On the other hand, when HL-60 is treated with PMA, the GM3 synthase activity increases and the lactosylceramide β1,3-N-acetylglucosaminyltransferase activity decreases [*J. Biol. Chem.*, 267, 23507 (1992)].

Accordingly, it is considered that, in the HL-60 treated with PMA, increase of ganglioside GM3 and decrease of neolacto-series glycolipids are caused by the increased GM3 synthase activity and the reduced lactosylceramide β1,3-N-acetylglucosaminyltransferase activity, and it differentiates into monocyte/macrophage as the result. It is considered that lactosylceramide β1,3-N-acetylglucosaminyltransferase and GM3 synthase are taking an important role in determining the induction and direction of the differentiation of promyelocyte.

It is known that leukocytes express different glycolipids depending on their types and differentiation stages. For example, mature myelogenous cell expresses only neutral neolacto-series glycolipid [*Mol. Cell. Biochem.*, 47, 81 (1982), *J. Biol. Chem.*, 260, 1067 (1985)]. On the other hand, mature lymphocyte expresses only globo-series glycolipid [*Mol. Cell. Biochem.*, 47, 81 (1982)]. It is suggested based on an analysis using leukocyte cell lines that the above differences of glycolipids are due to difference in the lactosylceramide β1,3-N-acetylglucosaminyltransferase activity. It has been found that the lactosylceramide β1,3-N-acetylglucosaminyltransferase activity is detected in myelogenous cell lines such as K-562, KG-1 and HL-60, but this enzyme activity is not detected in lymphocyte cell lines such as Reh, CCRF-CEM, MOLT-4, Ramos and RPMI 8226 [*Archives of Biochemistry and Biophysics*, 303, 125 (1993)].

It is known that a glycolipid having 3-sulfoglucuronic acid on the non-reducing terminal of its sugar chain (e.g., $SO_4$3GlcAβ1-3Galβ1-4GlcNAcβ1-3Galβ1-4Glc-ceramide) is expressed at a specific period of time and in a specific region during the differentiation of nerve system. It has been suggested that this glycolipid is concerned in the mutual recognition of nerve cells and migration of nerves [*J. Biol. Chem.*, 273, 8508 (1998)]. Since expression of the 3-sulfoglucuronic acid-containing glycolipid ($SO_4$3GlcAβ1-3Galβ1-4GlcNAcβ1-3Galβ1-4Glc-ceramide) in nerve cells is controlled by lactosylceramide β1,3-N-acetylglucosaminyltransferase, it is considered that mutual recognition and migration of nerve cells are controlled by the expression of lactosylceramide β1,3-N-acetylglucosaminyltransferase [*J. Biol Chem.*, 273, 8508 (1998)]. Since 3-sulfoglucuronic acid is recognized also by monoclonal antibody HNK-1 for a marker of human NK cell, it is also called HNK-1 epitope. Thus, it is considered that the 3-sulfoglucuronic acid-containing glycolipid plays an important role in the function of NK cell.

A sugar chain having GlcNAcβ1-3Gal structure is present in sugar chains of neolacto- and lacto-series glycolipids and also in N-linked sugar chains and O-linked sugar chains of glycoproteins, and in oligonsaccharide. For example, lacto-N-neotetraose (Galβ1-4GlcNAcβ1-3Galβ1-4Glc) and lacto-N-tetraose (Galβ1-3GlcNAcβ1-3Galβ1-4Glc), which exist in human milk, or various oligosaccharides having them as backbones can be cited as the oligosaccharides having GlcNAcβ1-3Gal structure [*Acta Paediatrica*, 82, 903 (1993)]. The GlcNAcβ1-3Gal structure is also an element constituting a poly-N-acetyllactosamine sugar chain. The poly-N-acetyllactosamine sugar chain is a sugar chain having structure in which N-acetyllactosamine is repeatedly bound via β1,3-linkage [(Galβ1-4GlcNAcβ1-3)$_n$; n is 2 or more], which is present in N-linked sugar chains and O-linked sugar chains of glycoproteins and also present in glycolipid sugar chains and oligosaccharides. Whether or not lactosylceramide β1,3-N-acetylglucosaminyltransferase uses substrates other than lactosylceramide, such as paraglobside, N-linked sugar chains and O-linked sugar chains of glycoproteins or oligosaccharides, has not been found.

Up to date, the lactosylceramide β1,3-N-acetylglucosaminyltransferase activity has been detected in colon tissues, colon cancer tissues, colon cancer cell lines (Colo205, SW403 and the like) and myeloid cell lines (K-562, KG-1 and HL-60), but there are no reports on the high purity purification of lactosylceramide β1,3-N-acetylglucosaminyltransferase [*J. Biol. Chem.*, 262, 15649 (1987), *Archives of Biochemistry and Biophysics*, 260, 461 (1988), *Carbohydrate Research*, 209, 261 (1991), *Archives of Biochemistry and Biophysics*, 303, 125 (1993)].

On the other hand, regarding enzymes having the activity to transfer N-acetylglucosamine via β1,3-linkage to the galactose residue present in the non-reducing terminal of sugar chains (hereinafter referred to as "Gal β1,3-N-acetylglucosaminyltransferase"), there are reports on their partial purification but it is not clear whether these enzymes use lactosylceramide as a substrate [*J. Biol. Chem.*, 268, 27118 (1993), *J. Biol. Chem.*, 267, 2994 (1992), *J. Biol. Chem.*, 263, 12461 (1988), *Jpn. J. Med. Sci. Biol.*, 42, 77 (1989)].

Regarding cloning of genes, genes of two types of Gal β1,3-N-acetylglucosaminyltransferases have so far been cloned [*Proc. Natl. Acad. Sci. USA*, 94, 14294-14299 (1997), *Proc. Natl. Acad. Sci. USA*, 96, 406-411 (1999)]. It has been shown that β3GnT as one of them uses paragloboside as its substrate in vitro, but its activity is weak when lactosylceramide is used as the substrate [*Glycobiology*, 9, 1123 (1999)]. Also, it has not been found whether β3GnT uses lactosylceramide and paragloboside as its substrates inside cells. In addition, the presence of the other Gal β1,3-N-acetylglucosaminyltransferase is not clear.

Since a large number of sugar chains having the GlcNAcβ1-3Gal structure are present, it seems highly possible that two or more Gal β1,3-N-acetylglucosaminyltransferases having different acceptor specificity and expression tissue are present and have respective different functions. Accordingly, it is considered that lactosylceramide β1,3-N-acetylglucosaminyltransferase can be identified by cloning a Gal β1,3-N-acetylglucosaminyltransferase which is different from the two Gal β1,3-N-acetylglucosaminyltransferases so far cloned, and examining its acceptor specificity.

As described above, it is known that lacto-N-neotetraose (Galβ1-4GlcNAcβ1-3Galβ1-4Glc) and lacto-N-tetraose (Galβ1-3GlcNAcβ1-3Galβ1-4Glc) or various oligosaccharides having them as backbones are present in human milk [*Acta Paediatrica*, 82, 903 (1993)]. These oligosaccharides have the GlcNAcβ1-3Gal structure in common. It is considered that they have a function to prevent babies from infection with viruses and microorganisms and a function to neutralize toxins. Also, they have an activity to accelerate growth of *Lactobacillus bifidus* which is a beneficial enteric bacterium. On the other hand, kinds of oligosaccharide existing in the milk of animals such as cows and mice are few and mostly lactose, and the above oligosaccharides existing in human milk are hardly present therein.

It may be industrially markedly useful if the above oligosaccharides contained in human milk or a milk containing them can be produced efficiently. When the gene of a Gal β1,3-N-acetylglucosaminyltransferase involved in the synthesis of the above oligosaccharides contained in human milk can be obtained, it is possible to use it in the efficient synthesis of the above oligosaccharides, but the enzyme has not been found yet.

Among sugar chains having the GlcNAcβ1-3Gal structure, particularly poly-N-acetyllactosamine sugar chain is a backbone sugar chain of many functional sugar chains (selectin ligand sugar chains, receptor sugar chains for microorganisms and viruses, SSEA-1 sugar chains, cancer-related sugar chains and the like) and deeply related to embryogenesis, cell differentiation or diseases such as inflammation and cancer. The poly-N-acetyllactosamine sugar chain also plays an important role in the stabilization of glycoprotein.

Since there is a possibility that Gal β1,3-N-acetylglucosaminyltransferases involved in the synthesis of poly-N-acetyllactosamine sugar chain functioning in respective cases are different, there is a possibility that a Gal β1,3-N-acetylglucosaminyltransferase different from the two enzymes so far cloned exists. There is a possibility that lactosylceramide β1,3-N-acetylglucosaminyltransferase is related to the synthesis of poly-N-acetyllactosamine sugar chain by transferring N-acetyllactosamine to sugar chains having Galβ1-4Glc or Galβ1-4GlcNAc at the non-reducing terminal (e.g., paraglobosid) in addition to lactosylceramide.

Synthesis, function and application of the poly-N-acetyllactosamine sugar chain are described below.

The poly-N-acetyllactosamine sugar chain is synthesized by the mutual actions of a GlcNAc β1,4-galactosyltransferase (an enzyme having an activity to transfer galactose via β1,4-linkage to the N-acetylglucosamine residue present in the non-reducing terminal of sugar chains) and Gal β1,3-N-acetylglucosaminyltransferase. Regarding GlcNAc β1,4-galactosyltransferase, genes of four enzymes (β4Gal-T1, β4Gal-T2, β4Gal-T3 and β4Gal-T4) have so far been cloned, and acceptor specificity of each enzyme has been analyzed [*J. Biol. Chem.*, 272, 31979-31991 (1997), *J. Biol. Chem.*, 273, 29331-29340 (1997)].

Saccharides such as fucose, sialic acid, N-acetylgalactosamine and galactose, a sulfate group and the like are added to linear or branched poly-N-acetyllactosamine sugar chains to thereby form various cell-specific or stage-specific sugar chains (functional sugar chains, blood group sugar chains, cancer-related sugar chains and the like) [*Glycobiology Series*, (1) to (6), edited by Akira Kobata, Senitiroh Hakomori and Yoshitaka Nagai, published by Kodansha (1993)].

It is known that poly-N-acetyllactosamine sugar chains having a sialyl Lewis x sugar chain [NeuAcα2-3Galβ1-4(fucα1-3)GlcNAc] at their terminal are present on granulocytes, monocytes or activated T cells, and it is considered that these sugar chains relate to the accumulation of the leukocytes into inflammatory regions by functioning as ligands of adhesion molecules, E-selectin and P-selectin [*Glycobiology Series*, (1) to (6), edited by Akira Kobata, Senitiroh Hakomori and Yoshitaka Nagai, published by Kodansha (1993)].

It is also known that poly-N-acetyllactosamine sugar chains having a sialyl Lewis x sugar chain and a sialyl Lewis a sugar chain [NeuAcα2-3Galβ1-3(fucα1-4)GlcNAc] at the terminal are present on cancer cells such as colon cancer, and it is suggested that the sugar chains are also involved in tumor metastasis by functioning as ligands of E-selectin and P-selectin [*Glycobiology Series*, (1) to (6), edited by Akira Kobata, Senitiroh Hakomori and Yoshitaka Nagai, published by Kodansha (1993)].

It is known that the structure of the poly-N-acetyllactosamine sugar chain changes during the process of embryogenesis, cell differentiation or malignant transformation of cells [*Glycobiology Series*, (1) to (6), edited by Akira Kobata, Senitiroh Hakomori and Yoshitaka Nagai, published by Kodansha (1993)]. While a linear poly-N-acetyllactosamine sugar chain is expressed on human fetal erythrocytes, a branched poly-N-acetyllactosamine sugar chain is expressed on adult erythrocytes [*Glycobiology Series*, (1) "Various World of Sugar Chains", edited by Akira Kobata, Senitiroh Hakomori and Yoshitaka Nagai, published by Kodansha, 1993]. ABO blood type antigens are expressed at the termini of the poly-N-acetyllactosamine sugar chains on erythrocytes. When a blood type antigen is expressed at respective termini of branched poly-N-acetyllactosamine sugar chains, it becomes a multivalent antigen and its binding ability with antibodies for blood type sugar chains increases $10^3$ times or more in comparison with a linear type antigen.

It is known that a series of sugar chain antigens are systemically expressed during the developing stage of mouse early embryo. SSEA-1 (stage specific embryonic antigen-1) is a Lewis x sugar chain [Galβ1-4(fucα1-3)GlcNAc] existing at the terminal of a poly-N-acetyllactosamine sugar chain, and expression of the antigen starts at the 8-cell stage, reaches its peak at the morula stage and gradually disappears after the blastocyst stage [*Glycobiology Series*, (3) "Glycobiology of Cell Society", edited by Akira Kobata, Senitiroh Hakomori and Yoshitaka Nagai, published by Kodansha, 1993]. The morula stage corresponds to a shifting stage in which germ cells so far proliferated by repeating simple numerical increase by cell division shift for the first time to the stage of blastocyst having differentiated "shape". Just before forming blastocyst, the morula cells closely assemble and cause cell compaction. When an oligosaccharide having the SSEA-1 is added, this cell compaction is inhibited and normal development thereafter is also inhibited [*J. Exp. Med.*, 160, 1591 (1984)]. It is also known that adhesion of mouse teratocarcinoma is inhibited by an anti-SSEA-1 antibody [*Glycobiology Series*, (3) "Glycobiology of Cell Society", edited by Akira Kobata, Senitiroh Hakomori and Yoshitaka Nagai, published by Kodansha, 1993]. The above findings show that the SSEA-1 plays an important role in the development of early embryo by acting as an adhesion molecule or a sugar chain signal.

It is known that poly-N-acetyllactosamine sugar chains are expressed in a large quantity in cancer cells in comparison with corresponding normal cells [*J. Biol. Chem.*, 259, 10834 (1984), *J. Biol. Chem.*, 261, 10772 (1986), *J. Biol. Chem.*, 266, 1772 (1991), *J. Biol. Chem.*, 267, 5700 (1992)]. It is known that when N-ras proto-oncogene is expressed in NIH3T3 cell, molecular weight of N-linked sugar chain on the cell surface is increased and the cell acquires infiltrating ability, and at the same time, the amount of poly-N-acetyllactosamine sugar chain in the N-linked sugar chain is increased and activities of β1,4-galactosyltransferase and β1,3-N-acetylglucosaminyltransferase which relates to the synthesis of poly-N-acetyllactosamine sugar chain are also increased [*J. Biol. Chem.*, 266, 21674 (1991)].

Galectins are a group of lectins having affinity for β-galactoside, which relate to the adhesion and signal transduction of cells, and their relation to diseases such as cancer is also suggested [*Trends in Glycoscience and Glycotechnology*, 9, 9 (1997)]. To date, 10 types of galectins are known in mammals. It is known that among these, galectin-1 and galectin-3 bind to linear poly-N-acetyllactosamine sugar chains with high affinity, and it is considered that certain glycoproteins containing these sugar chains are ligands of these galectins [*Trends in Glycoscience and Glycotechnology*, 9, 9 (1997), *Trends in Glycoscience and Glycotechnology*, 9, 47 (1997)].

Poly-N-acetyllactosamine sugar chains having sialic acids added to their termini serve as receptors for *Mycoplasma* and microorganisms [*Acta Paediatrica*, 82, 903 (1993)].

Thus, poly-N-acetyllactosamine sugar chains form backbone sugar chains of many functional sugar chains (selectin ligand sugar chains, receptor sugar chains for microorganisms and viruses, SSEA-1 sugar chain, cancer-related sugar chains and the like) and blood type sugar chains, and play important roles in efficiently presenting the sugar chains.

It is expected that poly-N-acetyllactosamine sugar chains having sialyl Lewis x sugar chains will become a medicament having anti-inflammatory effect or tumor metastasis inhibitory effect, as a selectin antagonist.

It is known that an oligosaccharide in which multivalent (four) sialyl Lewis x sugar chains (tetrasaccharides) is linked to poly-N-acetyllactosamine sugar chains shows the activity as a selectin antagonist at a low concentration of 1/100 or less in comparison with non-multivalent sialyl Lewis x sugar chains (tetrasaccharides) [*J. Exp. Med.*, 182, 1133 (1995), Glycobiology, 6, 65 (1996), *Glycobiology*, 1, 453 (1997), *Eur. J. Immunol.*, 27, 1360 (1997)]. Although a partially purified β1,3-N-acetylglucosaminyltransferase has been used for the synthesis of the poly-N-acetyllactosamine sugar chain moiety of the oligosaccharides, supply of this enzyme is a limiting factor so that it is difficult to synthesize a large amount of poly-N-acetyllactosamine sugar chains [*Glycobiology*, 7, 453 (1997)].

On the other hand, it is possible to synthesize poly-N-acetyllactosamine sugar chains by chemical synthesis, but its synthesis requires markedly complex steps [*Tetrahedron Letter*, 24, 5223 (1997)].

Accordingly, an efficient method for synthesizing poly-N-acetyllactosamine sugar chains is expected. Although the two types of Gal β1,3-N-acetylglucosaminyltransferases and their genes so far cloned may be used, it is considered that the use of other Gal β1,3-N-acetylglucosaminyltransferase having different substrate specificity and functions (e.g., lactosylceramide β1,3-N-acetylglucosaminyltransferase) and its gene may be efficient in some cases depending on the purpose.

The poly-N-acetyllactosamine sugar chains are also important for the stabilization of glycoprotein. Lysosome associated membrane glycoprotein-1 (lamp-1) and lysosome associated membrane glycoprotein-2 (lamp-2) are glycoproteins which exist in lysosome (partly exist on the cell surface) and almost completely cover inner face of lysosome membrane. Many sugar chains (some of them containing a poly-N-acetyllactosamine sugar chain) are added to lamp-1 and lamp-2 to prevent degradation of lamp-1 and lamp-2 by hydrolases in lysosome. It is known that when a human promyelocyte cell line HL-60 is treated with dimethyl sulfoxide, it differentiates into granulocyte cells, and during this differentiation process, the number of poly-N-acetyllactosamine sugar chains added to lamp-1 and lamp-2 increases and the metabolic rate (degradation rate) of lamp-1 and lamp-2 decreases [*J. Biol. Chem.*, 265, 20476 (1990)].

Examples for increase of the ability to synthesize poly-N-acetyllactosamine sugar chains are shown below.

It is shown that poly-N-acetyllactosamine sugar chains are added to sugar chains of cell membrane glycoproteins when F9 cell is treated with retinoic acid or when Swiss 3T3 cell is treated with TGF-β [*J. Biol. Chem.*, 268, 1242 (1993), *Biochim. Biophys. Acta.*, 1221, 330 (1994)].

It is known that activities of β1,4-galactosyltransferase and β1,3-N-acetylglucosaminyltransferase involved in the synthesis of poly-N-acetyllactosamine sugar chains are increased, and the amount of poly-N-acetyllactosamine sugar chains in N-binding type sugar chains of glycoprotein is increased, when N-ras proto-oncogene is expressed in NIH3 T3 cells [*J. Biol. Chem.*, 2, 21674 (1991)]. The molecular weight of a cell surface membrane protein CD43, CD45 or CD44 is increased when a core 2 β1,6-N-acetylglucosaminyltransferase gene is expressed in a T-cell line EL-4 [*J. Biol. Chem.*, 271, 18732 (1996)]. The reason for this may be that sugar chains synthesized by the core 2 β1,6-N-acetylglucosaminyltransferase become a good substrate of β1,3-N-acetylglucosaminyltransferase involved in the synthesis of poly-N-acetyllactosamine sugar chains.

Also, it is known that the amount of poly-N-acetyllactosamine sugar chains added to lamp-1 or lamp-2 is increased when HL-60 cells are cultured at 27° C. [*J. Biol. Chem.*, 266, 23185 (1991)].

However, there are no reports to date on the efficient production of recombinant glycoproteins to which poly-N-acetyllactosamine sugar chains are added, in host cells suitable for the production of recombinant glycoproteins (e.g., Namalwa cell, Namalwa KJM-1 cell, CHO cell). Accordingly, development of a process for efficiently producing a recombinant glycoprotein to which poly-N-acetyllactosamine sugar chains are added is an industrially important subject.

Although the two types of Gal β1,3-N-acetylglucosaminyltransferases so far cloned can be used, it is considered that use of other Gal β1,3-N-acetylglucosaminyltransferase having different substrate specificity and functions (e.g., lactosylceramide β1,3-N-acetylglucosaminyltransferase) may be efficient in some cases depending on the purpose.

DISCLOSURE OF THE INVENTION

An object of the present invention is to provide synthesis of useful sugar chains; medicaments such as antiinflammatory agents, anti-infective agents and tumor metastasis inhibitory agents; foods such as dairy products; a method for improving protein stability, and the like; and a method for diagnosing inflammatory diseases and types and malignancies of cancers, by use of a novel polypeptide having a β1,3-N-acetylglucosaminyltransferase activity.

The present invention relates to the following (1) to (79).

(1) A polypeptide which comprises the amino acid sequence represented by SEQ ID NO:1.

(2) A polypeptide which comprises an amino acid sequence of positions 39 to 378 in the amino acid sequence represented by SEQ ID NO:1.

(3) A polypeptide which comprises an amino acid sequence in which at least one amino acid in the amino acid sequence in the polypeptide according to (1) or (2) is deleted, substituted or added, and has a β1,3-N-acetylglucosaminyltransferase activity.

(4) A polypeptide which comprises an amino acid sequence having 60% or more homology with the amino acid sequence in the polypeptide according to (1) or (2), and has a 1,3-N-acetylglucosaminyltransferase activity.

(5) The polypeptide according to (3) or (4), wherein the β1,3-N-acetylglucosaminyltransferase activity is an activity to transfer N-acetylglucosamine via β1,3-linkage to a galactose residue present in its non-reducing terminal of a sugar chain.

(6) The polypeptide according to any one of (3) to (5), wherein the β1,3-N-acetylglucosaminyltransferase activity is an activity to transfer N-acetylglucosamine via β1,3-linkage to a galactose residue present in its non-reducing terminal of a sugar chain of an acceptor selected from i) galactose, N-acetyllactosamine (Galβ1-4GlcNAc), Galβ-1,3GlcNAc or lactose (Galβ1-4Glc), ii) an oligosaccharide having galactose, N-acetyllactosamine, Galβ1-3GlcNAc or lactose structure in its non-reducing terminal, and iii) a complex carbohydrate having a galactose, N-acetyllactosamine, Galβ1-3GlcNAc or lactose structure in its non-reducing terminal.

(7) The polypeptide according to (6), wherein the complex carbohydrate having galactose, N-acetyllactosamine, Galβ1-3GlcNAc or lactose structure in its non-reducing terminal is lactosylceramide (Galβ1-4Glc-ceramide) or paragloboside (Galβ1-4GlcNAcβ1-3Galβ1-4Glc-ceramide).

(8) The polypeptide according to (6) or (7), wherein the complex carbohydrate is a complex carbohydrate selected from a glycoprotein, a glycolipid, a proteoglycan, a glycopeptide, a lipopolysaccharide, a peptidoglycan and a glycoside in which a sugar chain is linked to a steroid compound.

(9) A sugar chain synthesizing agent which comprises the polypeptide according to any one of (1) to (8) as an active ingredient.

(10) A DNA which encodes the polypeptide according to any one of (1) to (8).

(11) A DNA which comprises the nucleotide sequence represented by SEQ ID NO:2.

(12) A DNA which comprises a nucleotide sequence of positions 135 to 1268 in the nucleotide sequence represented by SEQ ID NO:2.

(13) A DNA which comprises a nucleotide sequence of positions 249 to 1268 in the nucleotide sequence represented by SEQ ID NO:2.

(14) A DNA which hybridizes with a DNA comprising a nucleotide sequence complementary to the nucleotide sequence in the DNA according to any one of (10) to (13) under stringent conditions, and encodes a polypeptide having a β1,3-N-acetylglucosaminyltransferase activity.

(15) The DNA according to (14), wherein the β1,3-N-acetylglucosaminyltransferase activity is an activity to transfer N-acetylglucosamine via β1,3-linkage to a galactose residue present in its non-reducing terminal of a sugar chain.

(16) The DNA according to (14) or (15), wherein the β1,3-N-acetylglucosaminyltransferase activity is an activity to transfer N-acetylglucosamine via β1,3-linkage to a galactose residue present in its non-reducing terminal of a sugar chain of an acceptor selected from i) galactose, N-acetyllactosamine (Galβ1-4GlcNAc), Galβ1-3GlcNAc or lactose (Galβ1-4Glc), ii) an oligosaccharide having galactose, N-acetyllactosamine, Galβ1-3GlcNAc or lactose structure in its non-reducing terminal, and iii) a complex carbohydrate having galactose, N-acetyllactosamine, Galβ1-3GlcNAc or lactose structure in its non-reducing terminal.

(17) The DNA according to (16), wherein the complex carbohydrate having galactose, N-acetyllactosamine, Galβ1-3GlcNAc or lactose structure in its non-reducing terminal is lactosylceramide or paragloboside.

(18) The DNA according to (16) or (17), wherein the complex carbohydrate is a complex carbohydrate selected from a glycoprotein, a glycolipid, a proteoglycan, a glycopeptide, a lipopolysaccharide, a peptidoglycan and a glycoside in which a sugar chain is linked to a steroid compound.

(19) A DNA which comprises a nucleotide sequence complementary to the nucleotide sequence in the DNA according to any one of (10) to (18).

(20) A recombinant vector which is obtainable by inserting the DNA according to any one of (10) to (18) into a vector.

(21) A recombinant vector which is obtainable by inserting an RNA comprising a sequence homologous to the DNA according to any one of (10) to (18) into a vector.

(22) A transformant which comprises the recombinant vector according to (20) or (21).

(23) The transformant according to (22), wherein the transformant is a transformant selected from the group consisting of a microorganism, an animal cell, a plant cell and an insect cell.

(24) The transformant according to (23), wherein the microorganism is a microorganism belonging to the genus *Escherichia*.

(25) The transformant according to (23), wherein the animal cell is an animal cell selected from the group consisting of a mouse myeloma cell, a rat myeloma cell, a mouse hybridoma cell, a CHO cell, a BHK cell, an African green monkey kidney cell, a Namalwa cell, a Namalwa KJM-1 cell, a human fetal kidney cell and a human leukemia cell.

(26) The transformant according to (23), wherein the plant cell is a plant cell selected from the group consisting of plant cells of tobacco, potato, tomato, carrot, soybean, rape, alfalfa, rice plant, wheat, barley, rye, corn or flax.

(27) The transformant according to (23), wherein the insect cell is an insect cell selected from the group consisting of *Spodoptera frugiperda* ovarian cells, *Trichoplusia ni* ovarian cells and silkworm ovarian cells.

(28) The transformant according to (22), wherein the transformant is a non-human transgenic animal or transgenic plant.

(29) A process for producing a polypeptide, which comprises culturing the transformant according to any one of (22) to (27) in a medium to produce and accumulate the polypeptide according to any one of (1) to (8) in the culture, and recovering the polypeptide from the culture.

(30) A process for producing a polypeptide, which comprises breeding the non-human transgenic animal according to (28) to produce and accumulate the polypeptide according to any one of (1) to (8) in the animal, and recovering the polypeptide from the animal.

(31) The process according to (30), wherein the accumulation is carried out in animal milk.

(32) A process for producing a polypeptide, which comprises cultivating the transgenic plant according to (28) to produce and accumulate the polypeptide according to any one of (1) to (8) in the plant, and recovering the polypeptide from the plant.

(33) A process for producing a polypeptide, which comprises synthesizing the polypeptide according to any one of (1) to (8) by an in vitro transcription-translation system using the DNA according to any one of (10) to (18).

(34) A process for producing a sugar chain or complex carbohydrate by using the sugar chain synthesizing agent according to (9) as an enzyme source, which comprises allowing a) the enzyme source, b) an acceptor selected from i) lactosylceramide (Galβ1-4Glc-ceramide) or paragloboside (Galβ1-4GlcNAcβ1-3Galβ1-4Glc-ceramide), ii) galactose, N-acetyllactosamine (Galβ1-4GlcNAc), Galβ1-3GlcNAc or lactose (Galβ1-4Glc), iii) an oligosaccharide having galactose, N-acetyllactosamine (Galβ1-4GlcNAc), Galβ1-3GlcNAc or lactose structure in its non-reducing terminal, and iv) a complex carbohydrate having galactose, N-acetyllactosamine, Galβ1-3GlcNAc or lactose structure in its non-reducing terminal, and c) N-acetylglucosamine uridine 5'-diphosphate (UDP-Glcnac) to be present in an aqueous medium to produce and accumulate a sugar chain or complex carbohydrate in which N-acetylglucosamine is added via β1,3-linkage to a galactose residue of the acceptor in the aqueous medium, and recovering the sugar chain or complex carbohydrate from the aqueous medium.

(35) A process for producing a galactose-added sugar chain or complex carbohydrate by using the N-acetylglucosamine-added sugar chain or complex carbohydrate obtained by the process according to (34) as an acceptor, which comprises allowing a) the acceptor, b) GlcNAc β1,4-galactosyltransferase, and c) uridine 5'-diphosphate galactose (UDP-Gal) to be present in an aqueous medium to produce and accumulate a reaction product in which galactose is added via β1,4-linkage to an N-acetylglucosamine residue at the non-reducing terminal of the acceptor in the aqueous medium, and recovering the galactose-added sugar chain or complex carbohydrate from the aqueous medium.

(36) A process for producing a poly-N-acetyllactosamine sugar chain-added sugar chain or complex carbohydrate by using the sugar chain synthesizing agent according to (9) as an enzyme source, which comprises allowing a) the enzyme source, b) GlcNAc β1,4-galactosyltransferase, c) an acceptor selected from i) lactosylceramide (Galβ1-4Glc-ceramide) or paragloboside (Galβ1-4GlcNAcβ1-3Galβ1-4Glc-ceramide), ii) galactose, N-acetyllactosamine (Galβ1-4GlcNAc), Galβ1-3GlcNAc or lactose (Galβ1-4Glc), iii) an oligosaccharide having galactose, N-acetyllactosamine (Galβ1-4GlcNAc), Galβ1-3GlcNAc or lactose (Galβ1-4Glc) structure in its non-reducing terminal, iv) a complex carbohydrate having galactose, N-acetyllactosamine, Galβ1-3GlcNAc or lactose structure in its non-reducing terminal and v) a sugar chain or complex carbohydrate obtained by the process according to (34) or (35), d) uridine 5'-diphosphate N-acetylglucosamine (UDP-GlcNAc), and e) uridine 5'-diphosphate galactose (UDP-Gal) to be present in an aqueous medium to produce and accumulate a reaction product in which poly-N-acetyllactosamine sugar chain is added to the non-reducing terminal of the acceptor in the aqueous medium, and recovering the poly-N-acetyllactosamine sugar chain-added sugar chain or complex carbohydrate from the aqueous medium.

(37) A process for producing a sugar chain or complex carbohydrate, which comprises using the transformant according to any one of (22) to (27) to produce and accumulate a sugar chain comprising a saccharide selected from the group consisting of GlcNAcβ1-3Galβ1-4Glc-ceramide, a lacto-series glycolipid (a glycolipid having Galβ1-3GlcNAcβ1-3Galβ1-4Glc-ceramide as a backbone), a neolacto-series glycolipid (a glycolipid having Galβ1-4GlcNAcβ1-3Galβ1-4Glc-ceramide as a backbone), a saccharide having GlcNAcβ1-3Gal structure, a saccharide having GlcNAcβ1-3Galβ1-4GlcNAc structure, a saccharide having GlcNAcβ1-3Galβ1-3GlcNAc structure, a saccharide having GlcNAcβ1-3Galβ1-4Glc structure, a saccharide having (Galβ1-4GlcNAcβ1-3)$_n$Galβ1-4GlcNAc structure wherein n is 1 or more and a saccharide having a (Galβ1-4GlcNAcβ1-3)$_n$Galβ1-4Glc structure wherein n is 1 or more, or a complex carbohydrate containing the sugar chain, and recovering the sugar chain or complex carbohydrate from the culture.

(38) A process for producing a sugar chain or complex carbohydrate, which comprises using the non-human transgenic animal or transgenic plant according to (28) to produce and accumulate a sugar chain comprising a saccharide selected from the group consisting of GlcNAcβ1-3Galβ1-4Glc-ceramide, a lacto-series glycolipid (a glycolipid having Galβ1-3GlcNAcβ1-3Galβ1-4Glc-ceramide as a backbone), a neolacto-series glycolipid (a glycolipid having Galβ1-4GlcNAcβ1-3Galβ1-4Glc-ceramide as a backbone), a saccharide having GlcNAcβ1-3Gal structure, a saccharide having GlcNAcβ1-3Galβ1-4GlcNAc structure, a saccharide having GlcNAcβ1-3Galβ1-3GlcNAc structure, a saccharide having GlcNAcβ1-3Galβ1-4Glc structure, a saccharide having (Galβ1-4GlcNAcβ1-3)$_n$Galβ1-4GlcNAc structure wherein n is 1 or more and a saccharide having (Galβ1-4GlcNAcβ1-3)$_n$Galβ1-4Glc structure wherein n is 1 or more, or a complex carbohydrate containing the sugar chain, and recovering the sugar chain or complex carbohydrate from the individual.

(39) The process according to any one of (34) to (38), wherein the complex carbohydrate is selected from a glycoprotein, a glycolipid, a proteoglycan, a glycopeptide, a lipopolysaccharide, a peptidoglycan and a glycoside in which a sugar chain is linked to a steroid compound.

(40) The process according to (38), wherein the accumulation is carried out in an animal milk.

(41) An oligonucleotide which has a sequence identical to continuos 5 to 120 nucleotides of the nucleotide sequence in the DNA according to any one of (10) to (19), or which is a derivative of the oligonucleotide.

(42) A method for determining expression level of a gene encoding the polypeptide according to any one of (1) to (8), which comprises using the DNA according to any one of (10) to (19), a partial fragment of the DNA or the oligonucleotide according to (41) by a hybridization method.

(43) A method for determining expression level of a gene encoding the polypeptide according to any one of (1) to (8), which comprises using the oligonucleotide according to (41) by a polymerase chain reaction.

(44) A method for detecting an inflammation, cancer or tumor metastasis, which comprises using the method according to (42) or (43).

(45) An agent for detecting an inflammation, cancer or tumor metastasis, which comprises the DNA according to any one of (10) to (19), a partial fragment of the DNA or the oligonucleotide according to (41).

(46) A method for diagnosing functional abnormality of a gene, which comprises detecting mutation of the gene which encodes the polypeptide according to any one of (1) to (8).

(47) A method for detecting mutation of a gene encoding the polypeptide according to any one of (1) to (8), which comprises using the DNA according to any one of (10) to (19), a partial fragment of the DNA or the oligonucleotide according to (41) by a hybridization method.

(48) A method for detecting mutation of a gene encoding the polypeptide according to any one of (1) to (8), which comprises using the oligonucleotide according to (41) by a polymerase chain reaction.

(49) A method for inhibiting transcription of a gene encoding the polypeptide according to any one of (1) to (8) or translation of mRNA thereof, which comprises using the oligonucleotide according to (41).

(50) An antibody which recognizes the polypeptide according to any one of (1) to (8).

(51) A method for immunologically detecting the polypeptide according to any one of (1) to (8), which comprises using the antibody according to (50).

(52) A method for immunohistostaining, which comprises detecting the polypeptide according to any one of (1) to (8) by using the antibody according to (50).

(53) An immunohistostaining agent, which comprises the antibody according to (50).

(54) A medicament which comprises the polypeptide according to any one of (1) to (8).

(55) The medicament according to (54), which is a medicament for treating, preventing and/or diagnosing an inflammatory disease, cancer or tumor metastasis.

(56) A medicament which comprises the DNA according to any one of (10) to (19), a partial fragment of the DNA or the oligonucleotide according to (41).

(57) The medicament according to (56), which is a medicament for treating, preventing and/or diagnosing an inflammatory disease, cancer or tumor metastasis.

(58) A medicament which comprises the recombinant vector according to (20) or (21).

(59) The medicament according to (58), which is a medicament for treating, preventing and/or diagnosing an inflammatory disease, cancer or tumor metastasis.

(60) A medicament which comprises the antibody according to (50).

(61) The medicament according to (60), which is a medicament for treating, preventing and/or diagnosing an inflammatory disease, cancer or tumor metastasis.

(62) A method for screening a compound which changes a β1,3-N-acetylglucosaminyltransferase activity possessed by the polypeptide according to any one of (1) to (8), which measuring changes in the β1,3-N-acetylglucosaminyltransferase activity of the polypeptide caused by a sample to be tested by allowing the polypeptide to contact with the sample to be tested.

(63) The method according to (62), wherein the β1,3-N-acetylglucosaminyltransferase activity is an activity to transfer N-acetylglucosamine via β1,3-linkage to a galactose residue present in the non-reducing terminal of a sugar chain.

(64) The method according to (62) or (63), wherein the β1,3-N-acetylglucosaminyltransferase activity is an activity to transfer N-acetylglucosamine via β1,3-linkage to a galactose residue present in its non-reducing terminal of a sugar chain of an acceptor selected from i) galactose, N-acetyllactosamine (Galβ1-4GlcNAc), Galβ1-3GlcNAc or lactose (Galβ1-4Glc), ii) an oligosaccharide having galactose, N-acetyllactosamine, Galβ1-3GlcNAc or lactose structure in the non-reducing terminal, and iii) a complex carbohydrate having a galactose, N-acetyllactosamine, Galβ1-3GlcNAc or lactose structure in the non-reducing terminal.

(65) The method according to (62) or (63), wherein the complex carbohydrate having galactose, N-acetyllactosamine, Galβ1-3GlcNAc or lactose structure in the non-reducing terminal is lactosylceramide or paragloboside.

(66) The method according to (64) or (65), wherein the complex carbohydrate is a complex carbohydrate selected from a glycoprotein, a glycolipid, a proteoglycan, a glycopeptide, a lipopolysaccharide, a peptidoglycan and a glycoside in which a sugar chain is linked to a steroid compound.

(67) A method for screening a compound which changes expression of a gene encoding the polypeptide according to any one of (1) to (8), which comprises allowing the polypeptide to contact with the sample to be tested, and determining paragloboside or poly-N-acetylglucosamine sugar chain by using at least one selected from the group consisting of an antibody which recognizes paragloboside, and an antibody or lectin which recognizes poly-N-acetylglucosamine sugar chain.

(68) A method for screening a compound which changes expression of a gene encoding the polypeptide according to any one of (1) to (8), which comprises allowing a cell expressing the polypeptide to contact with a sample to be tested, and determining the polypeptide by using the antibody according to (50).

(69) A promoter DNA which controls transcription of a gene encoding the polypeptide according to any one of (1) to (8).

(70) The promoter DNA according to (69), which is a promoter functioning in a cell selected from a leukocyte cell, a nerve cell, a tracheal cell, a lung cell, a colon cell, a placental cell, a neuroblastoma cell, a glioblastoma cell, a colon cancer cell, a lung cancer cell, a pancreatic cancer cell, a stomach cancer cell and a leukemia cell.

(71) The promoter DNA according to (69) or (70), which is a human-, rat- or mouse-derived promoter DNA.

(72) A method for screening a compound which changes efficiency of transcription by the promoter DNA according to any one of (69) to (71), which comprises transforming an animal cell by using a plasmid containing the promoter DNA and a reporter gene ligated to the downstream of the promoter DNA, allowing the transformant to contact with a sample to be tested, and determining the translated product of the reporter gene.

(73) The method according to (72), wherein the reporter gene is a gene selected from a chloramphenicol acetyltransferase gene, a β-galactosidase gene, a β-lactamase gene, a luciferase gene and a green fluorescent protein gene.

(74) A compound obtainable by the method according to any one of (62) to (68), (72) and (73).

(75) A non-human knockout animal in which a deficiency or mutation is introduced into a DNA encoding the polypeptide according to (1) to (8).

(76) The knockout animal according to (75), wherein the non-human knockout animal is a mouse.

(77) A method for controlling differentiation, mutual recognition and migration of a cell, which comprises introducing the DNA according to any one of (10) to (18), an RNA comprising a sequence homologous to the DNA or the recombinant vector according to (20) or (21) into a cell to express the polypeptide according to any one of (1) to (8).

(78) The method according to (77), wherein the cell is a cell selected from any one of a blood cell, a nerve cell, a stem cell or a cancer cell.

(79) A method for accelerating differentiation of a promyelocyte into a granulocyte, which comprises introducing the DNA according to any one of (10) to (18), an RNA comprising a sequence homologous to the DNA or the recombinant vector according to (20) or (21) into a promyelocyte to express the polypeptide according to any one of (1) to (8).

The present invention is described below in detail.

(1) Preparation of a DNA Encoding the Polypeptide of the Present Invention and Production of the DNA and the Oligonucleotide The GlcNAc β1,3-galactosyltransferase disclosed in Japanese Published Unexamined Patent Application No. 181752/94 (hereinafter referred to as "β3Gal-T1"; alias WM1) is a GlcNAc β1,3-galactosyltransferase involved in the synthesis of Galβ1-3GlcNAc structure. Information on a DNA encoding the polypeptide of the present invention or nucleotide sequence of a part of the DNA can be obtained by retrieving genes having homology with this enzyme gene or genes having a possibility to encode proteins having homology with the enzyme at amino acid level from a gene data base using programs such as BLAST [*J. Mol. Biol.*, 215, 403-410 (1990)], FASTA (*Methods in Enzymology*, 183, 63-69) and FrameSearch (manufactured by Compugen). As the data bases, public data bases such as GenBank, EMBL and Geneseq (Derwent Publications) can be used, or personal data bases can also be used. These approaches reveled that the rat cDNA nucleotide sequence represented by SEQ ID NO:3 can be exemplified as nucleotide sequence of a gene having a possibility to encode a protein having homology with the β3Gal-T1 gene at amino acid level. Also, the human EST sequence of GenBank No. AI039637 can be exemplified as a human cDNA nucleotide sequence having homology with the nucleotide sequence of SEQ ID NO:3. These sequences are partial nucleotide sequences of DNAs encoding the polypeptides of the present invention.

The presence of the DNAs encoding the polypeptides of the present invention can be detected by carrying out polymerase chain reaction (hereinafter referred to as "PCR") [*Molecular Cloning, A Laboratory Manual*, Second Edition, Cold Spring Harbor Laboratory Press (1989) (hereinafter referred to as "*Molecular Cloning, Second Edition*") and *PCR Protocols*, Academic Press (1990)] using a single-stranded cDNAs or cDNA libraries prepared from various tissues or various cells as templates and primers specific for the above sequence. Also, a DNA fragment of the DNA encoding the polypeptide of the present invention can be obtained.

When the resulting DNA fragment is not a full-length, a full-length cDNA can be obtained as follows.

A tissue- or cell-derived cDNA library in which the presence of the DNA has been confirmed is screened by using the above obtained DNA fragment as a probe to thereby obtain a full-length cDNA.

Also, the 5' RACE method or the 3' RACE method is carried out by using a single-stranded cDNA or cDNA library in which the presence of the DNA has been confirmed as a template to thereby obtain 5'-terminal fragment and 3'-terminal fragment of cDNA having the sequence. A full-length cDNA can be obtained by ligating both fragments.

A single-stranded cDNA derived from various tissues or various cells can be prepared by a known method or a commercially available kit. An example is shown below.

A total RNA is prepared from various tissues or various cells according to a guanidine thiocyanate phenol-chloroform method [*Anal. Biochem.*, 162, 156-159 (1987)]. If necessary, a chromosomal DNA which may be contaminated is degradated by treatment of the total RNA with deoxyribonuclease I (manufactured by Life Technologies). A single-stranded DNA is synthesized from each of the resulting total RNA by using an oligo(dT)-primer or a random primer according to SUPERSCRIPT™ Preamplification System for First Strand cDNA System (manufactured by Life Technologies). The single-stranded cDNAs include single-stranded cDNAs prepared from human colon cancer cell line colo205 or human gastric mucosa according to the above method.

A cDNA library can be produced by a known method. The cDNA library construction method include methods described in *Molecular Cloning*, Second Edition, *Current Protocols in Molecular Biology*, John Wiley & Sons (1987-1997) (hereinafter referred to as "Current Protocols in Molecular Biology"), Supplements 1-38 and the like; methods using a commercially available kit such as SuperScript Plasmid System for cDNA Synthesis and Plasmid Cloning (manufactured by GIBCO BRL) and ZAP-cDNA Synthesis Kit (manufactured by STRATAGENE); and the like. A cDNA library derived from various tissues or various cells can be obtained by purchasing commercially available one.

Any of phage vectors, plasmid vectors and the like can be used as a cloning vector for constructing a cDNA library, so long as it can autonomously replicate in *Escherichia coli* K12. Examples include ZAP Express [manufactured by STRATAGENE, *Strategies*, 5, 58 (1992)], pBluescript SK(-) and pBluescript II SK(+) [*Nucleic Acids Research*, 17, 9494 (1989)], λZAP II (manufactured by STRATAGENE), λgt10 and λgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)], pUC18 [*Gene*, 33, 103 (1985)], pAMo [*J. Biol. Chem.*, 268, 22782-22787 (1993), alias pAMoPRC3Sc (Japanese Published Unexamined Patent Application No. 336963/93)], pGAD10 [*Gene*, 108, 193 (1991)] and the like.

Any microorganism can be used as a host microorganism, so long as it belongs to *Escherichia coli*. Examples include *Escherichia coli* XL1-Blue MRF' [manufactured by STRATAGENE, *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)], *Escherichia coli* SOLR™ Strain (manufactured by STRATAGENE), *Escherichia coli* LE392 (Molecular Cloning, Second Edition) and the like.

As a cDNA library, a cDNA library produced as follows is exemplified.

A cDNA is synthesized from a poly(A)$^+$ RNA of human gastric mucosa by using a cDNA synthesis system (cDNA Synthesis System, manufactured by GIBCO BRL), EcoRI-NotI-SalI adapter (Super Choice System for cDNA Synthesis; manufactured by GIBCO BRL) is added to both ends thereof, the cDNA is inserted into an EcoRI site of a cloning vector λZAP II (λZAP II/EcoRI/CIAP Cloning Kit, manufactured by STRATAGENE), and in vitro packaging is carried out by using Gigapack III Gold Packaging Extract (manufactured by STRATAGENE) to thereby produce a cDNA library.

Also, a commercially available cDNA library can be used by purchasing it.

Based on the nucleotide sequence of a candidate gene found by the data base search, primers specific for the gene are designed and PCR is carried out using the thus obtained single-stranded cDNAs or cDNA libraries as templates. When an amplified fragment is obtained, the fragment is subcloned into an appropriate plasmid. The subcloning can be carried out by inserting the amplified DNA fragment directly, or after treatment with restriction enzymes or DNA polymerase, into a vector in the usual way. Examples of the vectors include pBluescript SK(-) and pBluescript II SK(+) (both manufactured by STRATAGENE), pDIRECT [*Nucleic Acids Research*, 18, 6069 (1990)], pCR-Amp SK(+) [manufactured by STRATAGENE, *Strategies*, 5, 6264 (1992)], pT7Blue (manufactured by Novagen), pCR II [manufactured by Invitrogen; *Biotechnology*, 9, 657 (1991)], PCR-TRAP (manufactured by Genehunter), pNoTA$_{T7}$ (manufactured by 5'→3') and the like.

Whether or not the objective DNA fragment can be obtained is confirmed by sequencing then subcloned PCR amplified fragment. The nucleotide sequence can be determined by a generally used nucleotide sequence analyzing method such as the dideoxy method of Sanger et al. [*Proc. Natl. Acad. Sci. USA*, 74, 5463 (1997)] or using a nucleotide sequence analyzing apparatus such as 373A DNA sequencer (manufactured by Perkin Elmer).

A cDNA having a possibility to encode a protein homologous to the β3Gal-T1 at amino acid level can be obtained by colony hybridization or plaque hybridization (Molecular Cloning, Second Edition) for the cDNA libraries prepared in the above using the DNA fragment as a probe. As a probe, the DNA fragment labeled with an isotope or digoxigenin can be used.

The nucleotide sequence of the DNA obtained by the above method can be determined by inserting the DNA fragment as such or after its digestion with appropriate restriction enzymes or the like into a vector by a general method described in *Molecular Cloning*, 2nd Ed. or the like, and then analyzing it by a generally used nucleotide sequence analyzing method such as the dideoxy method of Sanger et al. [*Proc. Natl. Acad. Sci. USA,* 74, 5463 (1997)] or using a nucleotide sequence analyzing apparatus such as DNA sequencer 373A (manufactured by Perkin Elmer), DNA sequencer 377 (manufactured by Perkin Elmer) or DNA sequencer model 4000L (manufactured by LI-COR).

The DNAs obtained by this method include a DNA encoding a polypeptide which comprises the amino acid sequence represented by SEQ ID NO:1 or a polypeptide which comprises an amino acid sequence of positions 39 to 378 in the amino acid sequence represented by SEQ ID NO:1, and the like. Specific examples include a DNA which comprises the nucleotide sequence represented by SEQ ID NO:2, a DNA which comprises a nucleotide sequence of positions 135 to 1268 in the nucleotide sequence represented by SEQ ID NO:2, a DNA which comprises a nucleotide sequence of positions 249 to 1268 in the nucleotide sequence represented by SEQ ID NO:2, and the like.

Also, the nucleotide sequence represented by SEQ ID NO:2 is a nucleotide sequence derived from a cDNA encoding a polypeptide comprising the amino acid sequence represented by SEQ ID NO:1, the nucleotide sequence of positions 135 to 1268 in the nucleotide sequence represented by SEQ ID NO:2 is a nucleotide sequence corresponding to a coding region for the polypeptide, and the nucleotide sequence of positions 249 to 1268 in the nucleotide sequence represented by SEQ ID NO:2 is a nucleotide sequence encoding a region having a glycosyltransferase activity of the polypeptide.

Examples of plasmids comprising the DNA having the nucleotide sequence of positions 135 to 1268 in the nucleotide sequence represented by SEQ ID NO:2 include pAMo-G4, pCXN2-G6 and pBS-G4.

Generally, since plural codons are present for one amino acid, a DNA comprising a nucleotide sequence different from SEQ ID NO:2 is included in the DNA of the present invention, so long as it encodes the polypeptide of the present invention.

Based on the information of the nucleotide sequence in the DNAs of the present invention obtained by the above method, using a DNA comprising a 5'-terminal 15-30 bp sequence of the total nucleotide sequence of the DNA of the present invention or any region thereof, and a DNA comprising 3'-terminal 15-30 bp complementary sequence thereof as a sense primer and an antisense primer, respectively, PCR is carried out using cDNAs prepared from mRNAs of a cell expressing mRNAs complementary to the DNAs as templates to thereby prepare the DNAs of the present invention and the fragments of any region thereof. The DNAs used as primers can be synthesized by a DNA synthesizer such as 380A, 392 and 3900 manufactured by Applied Biosystems.

Furthermore, based on the amino acid sequence of the polypeptide encoded by the DNA of the present invention, the DNA of the present invention can be prepared by chemically synthesizing a DNA encoding the polypeptide. The DNA can be chemically synthesized by using a DNA synthesizer manufactured by Shimadzu Corporation according to the thiophosphate method, DNA synthesizers 380A, 392 and 3900 manufactured by Applied Biosystem according to the phosphoramidite method, and the like.

The objective DNAs encoding a polypeptide comprising an amino acid sequence in which at least one amino acid is deleted, substituted or added in the amino acid sequence represented by SEQ ID NO:1 can be obtained by selecting a DNA which hybridizes with a DNA comprising a sequence complementary to the nucleotide sequence of the DNA obtained by the above method under stringent conditions. For example, a homologue DNA and the like of other species (mouse, rat, calf, monkey or the like) can be cloned. Specifically, a rat homologue DNA represented by SEQ ID NO:3 is exemplified.

Except for the synthesis method using a DNA synthesizer, the DNAs encoding the polypeptide of the present invention are obtained as double-stranded DNAs consisting of a sense DNA encoding the polypeptide of the present invention and a DNA comprising a sequence complementary to the nucleotide sequence of the DNA. Both the DNAs can be separated by heating at 100° C. for 5 minutes, followed by rapid cooling on ice. The DNA comprising a sequence complementary to the nucleotide sequence of the DNA encoding the polypeptide of the present invention can by synthesized by a DNA polymerase reaction in the presence of dNTP using the above separated sense DNA encoding the polypeptide of the present invention as a template and a DNA comprising a sequence complementary to 3'-terminal 5-30 bp sequence of the sense DNA as a primer.

A DNA which is hybridizable under stringent conditions is a DNA obtained by carrying out colony hybridization, plaque hybridization, Southern hybridization or the like using the DNA obtained in the above as a probe. Examples include a DNA which can be identified by hybridization at 65° C. in the presence of 0.7 to 1.0 M sodium chloride using a filter to which colony- or plaque-derived DNA samples are immobilized and then washing the filter at 65° C. with 0.1 to 2 times concentration of SSC solution (composition of the original concentration SSC containing 150 mmol/l sodium chloride and 15 mmol/l sodium citrate).

The hybridization can be carried out according to the method described in *Molecular Cloning,* Second Edition, *Current Protocols in Molecular Biology, DNA Cloning 1: Core Techniques, A Practical Approach,* Second Edition., Oxford University (1995) or the like. The hybridizable DNA includes a DNA having a homology of 60% or more, preferably 70% or more, more preferably 80% or more, still more preferably 90% or more, particularly preferably 95% or more, and most preferably 97% or more, with the DNA obtained above, when calculated using a default (initial establishment) parameter with an analysis software such as BLAST [*J. Mol. Biol.,* 215, 403 (1990)] or FASTA [*Methods in Enzymology,* 183, 63-98 (1990)].

Oligonucleotides, such as a sense oligonucleotide having a partial sequence of the DNA of the present invention and an antisense oligonucleotide having a partial sequence of a nucleotide sequence complementary to the nucleotide sequence of the DNA of the present invention can be prepared using the DNA and DNA fragments of the present invention obtained by the above method, in a conventional manner described in *Molecular Cloning,* Second Edition or the like or using a DNA synthesizer based on the nucleotide sequence information of the DNA.

The oligonucleotide includes a DNA comprising a sequence identical to continuous 5 to 120 nucleotides, preferably continuos 5 to 60 nucleotides, is the nucleotide sequence in the DNA of the present invention or a nucleotide sequence complementary to the nucleotide sequence. Examples include a DNA comprising a sequence identical to continuous 5 to 120 nucleotides in the nucleotide sequence represented by SEQ ID NO:2 or a DNA comprising the same sequence as continuos 5 to 120 nucleotides in a sequence complementary to the nucleotide sequence represented by SEQ ID NO:2. When used as a forward primer and a reverse primer, the above oligonucleotides in which the melting temperatures (Tm) and the number of nucleotides therebetween are not significantly different are preferred. Examples include oligonucleotides comprising the nucleotide sequence represented by SEQ ID NO:25 or 28 and the like.

Moreover, derivatives of these oligonucleotides (hereinafter referred to as "oligonucleotide derivatives") can also be used as the oligonucleotides of the present invention.

Examples of the oligonucleotide derivatives include oligonucleotide derivatives in which a phosphodiester bond in the oligonucleotide is converted into a phosphorothioate bond, oligonucleotides derivative in which a phosphodiester bond in the oligonucleotide is converted into an N3'-P5' phosphoamidate bond, oligonucleotide derivatives in which ribose and a phosphodiester bond in the oligonucleotide are converted into a peptide-nucleic acid bond, oligonucleotide derivatives in which uracil in the oligonucleotide is substituted with C-5 propynyluracil, oligonucleotide derivatives in which uracil in the oligonucleotide is substituted with C-5 thiazoleuracil, oligonucleotide derivatives in which cytosine in the oligonucleotide is substituted with C-5 propynylcytosine, oligonucleotide derivatives in which cytosine in the oligonucleotide is substituted with phenoxazine-modified cytosine, oligonucleotide derivatives in which ribose in the oligonucleotide is substituted with 2'-propylribose, oligonucleotide derivatives in which ribose in the oligonucleotide is substituted with 2'-methoxyethoxyribose, and the like [*Cell Technology*, 16, 1463 (1997)].

The polypeptide of the present invention encoded by the thus obtained DNA of the present invention includes a polypeptide which comprises the amino acid sequence represented by SEQ ID NO:1; a polypeptide which comprises an amino acid sequence of positions 39 to 378 in the amino acid sequence represented by SEQ ID NO:1; a polypeptide which comprises an amino acid sequence in which at least one amino acid in the amino acid sequence in the above polypeptide is deleted, substituted or added, and has a β1,3-N-acetylglucosaminyltransferase activity; a polypeptide which comprises an amino acid sequence having 60% or more of homology with the amino acid sequence in the above polypeptide, and has a lactosylceramide β1,3-N-acetylglucosaminyltransferase activity and a paragloboside β1,3-N-acetylglucosaminyltransferase activity; and the like.

A protein comprising an amino acid sequence in which at least one amino acid is deleted, substituted and/or added in the polypeptide having the above amino acid sequence can be obtained, for example, by introducing site-directed mutation into the DNA encoding the polypeptide comprising the amino acid sequence represented by SEQ ID NO:1 according to the site-directed mutagenesis method described in *Molecular Cloning, A Laboratory Manual*, Second Edition, Cold Spring Harbor Laboratory (1989) (hereinafter referred to as "*Molecular Cloning*, Second Edition"), *Current Protocols in Molecular Biology*, John Wiley & Sons (1987-1997) (hereinafter referred to as "Current Protocols in Molecular Biology"), *Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl. Acad. Sci. USA*, 82, 488 (1985) or the like. The number of amino acids which have been deleted, substituted or added is not particularly limited; however, they are 1 to tens, preferably 1 to 20, more preferably 1 to 10 and most preferably 1 to 5 amino acids.

Also, the polypeptide of the present invention includes an amino acid sequence having a homology of 60% or more with the amino acid sequence represented by SEQ ID NO:1. The homology with the amino acid sequence represented by SEQ ID NO:1 is 60% or more, preferably 70% or more, more preferably 80% or more, still more preferably 90% or more, particularly preferably 95% or more, and most preferably 97% or more, when calculated using a default (initial establishment) parameter with an analysis software such as BLAST [*J. Mol. Biol.*, 215, 403 (1990)] or FASTA [*Methods in Enzymology*, 183, 63-69 (1990)]. For example, a homologue polypeptide of other species (mouse, rat, calf, monkey or the like) is exemplified. Specifically, the rat polypeptide represented by SEQ ID NO:3 is exemplified.

According to the method described in the following (3), it can be confirmed that the polypeptide of the present invention has a β1,3-N-acetylglucosaminyltransferase activity.

(2) Production of the Polypeptide of the Present Invention

In order to express the DNA of the present invention obtained by the above method in a host and produce the polypeptide of the present invention, methods described in *Molecular Cloning*, Second Edition, *Current Protocols in Molecular Biology*, Supplements 1 to 38 and the like can be used.

Specifically, a recombinant vector to which the DNA of the present invention has been inserted into the downstream of the promoter of a suitable expression vector is constructed, a transformant expressing the polypeptide of the present invention is obtained by introducing the vector into a host cell, and the transformant is cultured to produce the polypeptide of the present invention.

Any of bacteria, yeast, animal cells, insect cells, plant cells and the like can be used as the host cell, so long as it can express the objective gene.

The expression vector includes those which can autonomously replicate in the above host cell or which can be integrated into a chromosome and have a promoter at such an operative position that the DNA of the present invention can be transcribed.

When prokaryote, such as a bacterium, is used as a host cell, it is preferred that the expression vector for the polypeptide gene of the present invention can autonomously replicate in the prokaryote and is a recombinant vector constructed with a promoter, a ribosome binding sequence, the DNA of the present invention and a transcription termination sequence. A promoter-controlling gene can also be utilized.

The expression vector includes pBTrp2, pBTac1 and pBTac2 (all available from Boehringer Mannheim), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBlue II SK(−) (manufactured by STRATAGENE), pTrs30 (FERM BP-5407), pTrs32 (FERM BP-5408), pGHA2 (FERM BP-400), pGKA2 (FERM B-6798), pTerm2 (Japanese Published Unexamined Patent Application No. 22979/91, U.S. Pat. No. 4,686,191, U.S. Pat. No. 4,939,094, U.S. Pat. No. 5,160,735), pKK233-2 (manufactured by Pharmacia), pGEX (manufactured by Pharmacia), pET (manufactured by Novagen), pSupex, pUB110, pTP5, pC194, pTrxFus (manufactured by Invitrogen), pMAL-c2 (manufactured by New England Biolabs) and the like.

Any promoter can be used, so long as it can work for expression in a host cell such as *Escherichia coli*. Examples include promoters derived from *Escherichia coli*, phage and the like, such as trp promoter (Ptrp), lac promoter (Plac), $P_L$ promoter and $P_R$ promoter, SPO1 promoter, SPO2 promoter and penp promoter. Also, artificially designed and modified promoters, such as a promoter in which two Ptrp are linked in series (Ptrp×2), tac promoter, lacT7 promoter and letI promoter, can be used.

As the ribosome binding sequence, it is preferred to use a plasmid in which the space between Shine-Dalgarno sequence and the initiation codon is adjusted to a suitable distance (for example, 6 to 18 nucleotides).

The transcription termination sequence is not required for the expression of the DNA of the present invention. However, the transcription terminating sequence is preferably arranged at just downstream of the structural gene.

The host cell includes microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas* and the like, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia Coli* No. 49, *Escherichia coli* W3110, *Escherichia coli* NY49, *Escherichia coli* BL21(DE3), *Escherichia coli* BL21(DE3) pLysS, *Escherichia coli* HMS174(DE3), *Escherichia coli* HMS174(DE3)pLysS, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC 14068, *Brevibacterium saccharolyticum* ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354 and *Pseudomonas* sp. D-0110.

Any method can be used in the method for introducing the recombinant vector, so long as it is a method for introducing a DNA into the above host cell, such as an electroporation method [*Nucleic Acids Res.*, 16, 6127 (1988)], a method using a calcium ion [*Proc. Natl. Acad. Sci. USA*, 69, 2110 (1972)], a protoplast method (Japanese Published Unexamined Patent Application No. 248394/88) and methods described in *Gene*, 17, 107 (1982) and *Molecular & General Genetics*, 168, 111 (1979).

When yeast is used as the host cell, the expression vector includes YEp13 (ATCC 37115), YEp24 (ATCC 37051), YCp50 (ATCC 37419), pHS19, pHS15 and the like.

Any promoter can be used, so long as it can be expressed in yeast. Examples include PHO5 promoter, PGK promoter, GAP promoter, ADH promoter, gal 1 promoter, gal 10 promoter, a heat shock polypeptide promoter, MFα1 promoter, CUP 1 promoter, and the like.

Examples of the host cell include yeast strains belonging to the genus *Saccharomyces*, the genus *Schizosaccharomyces*, the genus *Kluyveromyces*, the genus *Trichosporon*, the genus *Schwanniomyces* and the like, such as *Saccharomyces cerevisiae*, *Schizosaccharomyces pombe*, *Kluyveromyces lactis*, *Trichosporon pullulans* and *Schwanniomyces alluvius*.

Any method can be used as the method for introducing the recombinant vector, so long as it is a method for introducing a DNA into yeast. Examples include an electroporation method [*Methods. Enzymol.*, 194, 182 (1990)], a spheroplast method [*Proc. Natl. Acad. Sci. USA*, 84, 1929 (1978)], a lithium acetate method [*J. Bacteriol.*, 153, 163 (1983)], the method described in *Proc. Natl. Acad. Sci. USA*, 75, 1929 (1978) and the like.

When an animal cell is used as the host, the expression vector includes pcDNAI/Amp (manufactured by Invitrogen), pcDNAI (manufactured by Funakoshi), pcDM8 [*Nature*, 329, 840 (1987), manufactured by Funakoshi], pAGE107 [Japanese Published Unexamined Patent Application No. 22979/91; *Cytotechnology*, 3, 133 (1990)], pREP4 (manufactured by Invitrogen), pAGE103 [*J. Biochemistry*, 101, 1307 (1987)], pAMo [*J. Biol. Chem.*, 268, 22782 (1993)], pAMoA [*J. Biol. Chem.*, 268, 22782 (1993)], pAS3-3 (Japanese Published Unexamined Patent Application No. 227075/90) and the like.

Any promoter can be used as the method for introducing the recombinant vector, so long as it can work for expression in the animal cell. Examples include a promoter of IE (immediate early) gene of cytomegalovirus (human CMV), an early promoter of SV40, a long terminal repeat promoter of moloney murine leukemia virus, a promoter of retrovirus, a heat shock promoter, SRα promoter, a promoter of metallothionein and the like. Also, the enhancer of the IE gene of human CMV can be used together with the promoter.

As the host cell, any cell can be used, so long as it is an animal cell into which a DNA can be introduced. For example, as cells of mammals such as human, monkey, mouse, rat, guinea pig and mink can be used. Examples include mouse myeloma cell, rat myeloma cell, mouse hybridoma cell, Chinese hamster CHO cell (ATCC CRL-9096, ATCC CCL-61), BHK cell, African green monkey kidney cell, human Namalwa cell (ATCC CRL-1432), human Namalwa KJM-1 cell, human fetal kidney cell, human leukemic cell, HBT5637 (Japanese Published Unexamined Patent Application No. 299/88), human colon cancer cell line and the like.

The mouse myeloma cell includes SP2/0, NS0 and the like. The rat myeloma cell includes YB2/0 and the like. The human fetal kidney cell includes BALL-1 and the like. The African green monkey kidney cell includes COS-1 (ATCC CRL-1650), COS-7 (ATCC CRL-1651) and the like. The human colon cancer cell line includes HCT-15 and the like.

When an object is to produce proteinous medicaments for treatment, cells of mammals, particularly CHO cell, is preferably used as the host.

Any method can be used as the method for introducing the recombinant vector into an animal cell, so long as it is a method for introducing a DNA into an animal cell. Examples include an electroporation method [*Cytotechnology*, 3, 133 (1990)], a calcium phosphate method (Japanese Published Unexamined Patent Application No. 227075/90), a DEAE dextran method (Yodosha, Bio Manual Series 4, 16), a lipofection method [*Proc. Natl. Acad. Sci. USA*, 84, 7413 (1987)], a microinjection method (Yodosha, Bio Manual Series 4, 36), an adenovirus method (Yodosha, Bio Manual Series 4, 43), a vaccinia virus method (Yodosha, Bio Manual Series 4, 59), a retrovirus method (Yodosha, Bio Manual Series 4, 74) and the like.

When an insect cell is used as the host, the polypeptide can be expressed by a known method described in, for example, *Bacurovirus Expression Vectors, A Laboratory Manual*, W.H. Freeman and Company, New York (1992), *Molecular Biology, A Laboratory Manual, Current Protocols in Molecular Biology, Supplements* 1 to 38, Bio/Technology, 6, 47 (1988) or the like.

Specifically, a recombinant gene transfer vector and baculovirus are co-transfected into an insect cell to obtain a recombinant virus in an insect cell culture supernatant, and then the insect cell is infected with the resulting recombinant virus to express of the polypeptide.

The gene transfer vector used in the method includes pVL1392 (manufactured by Pharmingen), pVL1393 (manufactured by Pharmingen), pBlueBacIII (manufactured by Invitrogen) and the like.

The bacurovirus includes *Autographa californica* nuclear polyhedrosis virus which infects insects of the family Noctuidae, and the like.

The insect cell includes *Spodoptera frugiperda* ovary cell, *Trichoplusia ni* ovary cell, *Bombyx mori* ovary-derived cultured cell and the like. The *Spodoptera frugiperda* ovary cell includes Sf9 and Sf21 (*Bacurovirus Expression Vectors, A Laboratory Manual*) and the like. The *Trichoplusia ni* ovary cell includes High 5 (alias BTI-TN-5Bl-4, manufactured by Invitrogen) and the like. The *Bombyx mori* ovary-derived cultured cell includes *Bombyx mori* N4 and the like.

The method for co-transfecting the above recombinant gene transfer vector and the above bacurovirus for the preparation of the recombinant virus include a calcium phosphate method (Japanese Published Unexamined Patent Application No. 227075/90), a lipofection method [*Proc. Natl. Acad. Sci. USA*, 84, 7413 (1987)] and the like. Furthermore, the DNA can be introduced into an insect cell by using a method similar to the method for introducing a DNA into an animal cell. Examples include an electroporation method [*Cytotechnology*, 3, 133 (1990)], a calcium phosphate method (Japanese Published Unexamined Patent Application No. 227075/90), a lipofection method [*Proc. Natl. Acad. Sci. USA*, 84, 7413 (1987)] and the like.

When a plant cell or a plant is used as the host, the polypeptide can be produced according to a known method [*Tissue Culture*, 20 (1994), *Tissue Culture* 21 (1995), *Trends in Biotechnology*, 15, 45 (1997)].

As the promoter used in the gene expression, any promoter can be used, so long as it can function in plant cells. Examples include cauliflower mosaic virus (CaMV) 35S promoter, rice actin 1 promoter and the like. Also, the gene expression efficiency can be improved by inserting intron 1 of corn alcohol dehydrogenase gene or the like between the promoter and the gene to be expressed.

The host cell includes plant cells such as potato, tobacco, corn, rice, rape, soybean, tomato, wheat, barley, rye, alfalfa and flax. As the method for introducing a recombinant vector, any method for introducing a DNA into a plant cell can be used. Examples include a method using *Agrobacterium* (Japanese Published Unexamined Patent Application No. 140885/84, Japanese Published Unexamined Patent Application No. 70080/85, WO 94/00977), an electroporation method [*Cytotechnology*, 3, 133 (1990), Japanese Published Unexamined Patent Application No. 251887/85], a method using a particle gun (gene gun) (Japanese Patent No. 2606856, Japanese Patent No. 2517813) and the like.

A cell or organ of the gene-introduced plant can be cultured in a large amount using a jar fermentor. Also, a gene-introduced plant (transgenic plant) can be constructed by re-differentiating the gene-introduced plant cell.

The polypeptide of the present invention can also be produced using an animal. For example, the polypeptide of the present invention can be produced in a gene-introduced animal according to known methods [*American Journal of Clinical Nutrition*, 63, 639S (1996), *American Journal of Clinical Nutrition*, 63, 627S (1996), *Bio/Technology*, 9, 830 (1991)].

Any promoter which can be expressed in an animal can be used and, for example, mammary gland cell-specific promoters such as α-casein promoter, β-lactoglobulin promoter and whey acidic protein promoter are suitably used.

The polypeptide of the present invention can be produced by culturing a transformant derived from a microorganism, animal cell or plant cell having a recombinant vector into which DNA encoding the polypeptide is inserted, according to a general culturing method, to thereby produce and accumulate the polypeptide, and then recovering the polypeptide from the resulting culture mixture.

When the transformant is an animal or plant, the polypeptide can be produced by breeding or cultivating it according to a general breeding or cultivating method to thereby produce and accumulate the polypeptide, and then recovering the polypeptide from the animal or plant.

That is, in an animal, the polypeptide of the present invention can be obtained by, for example, breeding a non-human transgenic animal having the DNA of the present invention to produce and accumulate the polypeptide of the present invention encoded by the recombinant DNA in the animal, and then recovering the polypeptide from the animal. Examples of the production and accumulation part in the animal include milk (Japanese Published Unexamined Patent Application No. 309192/86), eggs and the like.

In a plant, the polypeptide of the present invention can be obtained by, for example, cultivating a transgenic plant having the DNA of the present invention to produce and accumulate the polypeptide of the present invention encoded by the recombinant DNA in the plant, and then recovering the polypeptide from the plant.

When the transformant for use in the production of the polypeptide of the present invention is prokaryote such as *Escherichia coli* or eukaryote such as yeast, the medium for culturing such an organism may be either a natural medium or a synthetic medium, so long as it contains carbon sources, nitrogen sources, inorganic salts and the like which can be assimilated by the organism and can efficiently culture the transformant.

The carbon sources include those which can be assimilated by the transformant. Examples include carbohydrates such as glucose, fructose, sucrose, molasses containing them, starch and starch hydrolysate; organic acids such as acetic acid and propionic acid; alcohols such as ethanol and propanol; and the like.

The nitrogen sources includes ammonia, various ammonium salts of inorganic acids and organic acids such as ammonium chloride, ammonium sulfate, ammonium acetate and ammonium phosphate; other nitrogen-containing compounds, as well as peptone, meat extract, yeast extract, corn steep liquor, casein hydrolysate, soybean meal and soybean meal hydrolysate and various fermented cells and hydrolysates thereof.

The inorganic materials include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is carried out under aerobic conditions such as shaking culture and submerged agitation aeration culture. The culturing temperature is preferably from 15 to 40° C., and the culturing time is generally from 16 to 96 hours. During culturing, the pH is controlled at 3.0 to 9.0. The pH is adjusted using an inorganic or organic acid, an alkali solution, urea, calcium carbonate, ammonia or the like.

If necessary, antibiotics such as ampicillin and tetracycline may be added to the medium during culturing.

When a microorganism transformed with an expression vector obtained using an inducible promoter as the promoter is cultured, an inducer may be added to the medium, if necessary. For example, isopropyl-β-D-thiogalactopyranoside (IPTG) or the like may be added to the medium when a microorganism transformed with an expression vector obtained using lac promoter is cultured, or indoleacrylic acid (IAA) or the like may be added to the medium when a microorganism transformed with an expression vector obtained using trp promoter is cultured.

When the transformant for the production of the polypeptide of the present invention is an animal cell, generally used RPMI 1640 medium [*The Journal of the American Medical Association*, 199, 519 (1967)], Eagle's MEM [*Science*, 122, 501 (1952)], DMEM [*Virology*, 8, 396 (1959)], 199 Medium [*Proceeding of the Society for the Biological Medicine*, 73, 1 (1950)] or any one of these media further supplemented with fetal calf serum or the like can be used.

Culturing is carried out generally at pH 6 to 8 and at 30 to 40° C. in the presence of 5% $CO_2$ for 1 to 7 days.

If necessary, antibiotics such as kanamycin and penicillin may be added to the medium during culturing.

As the medium for use in culturing of a transformant obtained using an insect cell as the host, usually used TNM-FH medium (manufactured by PharMingen), Sf-900 II SFM medium (manufactured by GIBCO BRL), ExCell 400 or ExCell 405 (both manufactured by JRH Biosciences), Grace's Insect Medium [*Nature*, 195, 788 (1962)] or the like can be used. Culturing is carried out at pH 6 to 7 and at 25 to 30° C. for 1 to 5 days. Also, if necessary, antibiotics such as gentamicin may be added to the medium during culturing.

A transformant obtained using a plant cell as the host cell can be used as the cell or after differentiating to a plant cell or organ. Examples of the medium used in culturing of the transformant include Murashige and Skoog (MS) medium, White medium, media to which a plant hormone such as auxin or cytokinine has been added, and the like. Culturing is carried out generally at a pH 5 to 9 and at 20 to 40° C. for 3 to 60 days. Also, if necessary, antibiotics such as kanamycin and hygromycin can be added to the medium during culturing.

Regarding the gene expression method, it can also be expressed as a partial polypeptide containing a region having a β1,3-N-acetylglucosaminyltransferase activity, in addition to the case of expressing a full-length polypeptide. In general, a glycosyltransferase has the topology of type II membrane protein and comprises an N-terminal cytoplasmic tail region containing several to several dozen amino acids, a membrane-binding region having a highly hydrophobic amino acid sequence, a stem region containing several to several dozen amino acids and the remaining most part of C-terminal moiety containing a catalytic region. It is considered that the stem region and the remaining most part of C-terminal moiety containing the catalytic region are exposed to the Golgi body cavity. Boundary between the stem region and catalytic region can be experimentally obtained by preparing N-terminal-deleted polypeptides and examining degree of the deletion by which the activity disappears. On the other hand, the stem region and catalytic region can be estimated by comparing the amino acid sequence with that of similar glycosyltransferase having information on the stem region and catalytic region.

It is expected that the polypeptide of the present invention represented by SEQ ID NO:1 comprises an N-terminal cytoplasmic tail region containing 14 amino acids, a subsequent membrane-binding region rich in hydrophobic nature containing 18 amino acids, a stem region containing at least 12 amino acids, and the remaining most part of C-terminal moiety containing a catalytic region. Accordingly, a polypeptide comprising the amino acid sequence of positions 45 to 378 is considered to comprise a catalytic region.

The stem region was estimated based on the comparison of the homology of the amino acid sequence with those of other β1,3-N-acetylglucosaminyltransferase and β1,3-galactosyltransferase and information on the stem regions of other β1,3-N-acetylglucosaminyltransferases and β1,3-galactosyltransferases. Specifically, the stem region can be estimated based on the information disclosed in Example 4 of this specification, and in Japanese Published Unexamined Patent Application No. 181759/94. For example, a secreted polypeptide comprising amino acids of positions 36 to 378 in SEQ ID NO:1 and a secreted polypeptide comprising amino acids of positions 39 to 378 in SEQ ID NO:1 have β1,3-N-acetylglucosaminyltransferase activities.

In addition to its direct expression, the above full-length polypeptide or partial polypeptides containing a region having a β1,3-N-acetylglucosaminyltransferase activity (catalytic region) can also be expressed as a secreted protein or a fusion protein according to a method described in *Molecular Cloning,* 2nd Ed. or the like. Examples of proteins to be fused include β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA binding protein domain, Tac antigen, thioredoxin, green fluorescent protein, FLAG peptide, epitopes of antibodies of interest and the like [Akio Yamakawa, *Jikken Igaku,* 13, 469-474 (1995)].

A process to produce the polypeptide of the present invention includes a process to produce it inside of a host cell, a process to secrete it extracellularly from a host cell, and a process to produce it on the outermembrane of a host cell. The process is selected depending on a host cell to use or the structure of the polypeptide to produce.

When the polypeptide of the present invention is produced inside of a host cell or on the outer membrane of a host cell, the polypeptide can be positively secreted extracellularly from the host cell according to the method of Paulson et al. [*J. Biol. Chem.,* 264, 17619 (1989)], the method of Lowe et al. [*Proc. Natl. Acad. Sci. USA,* 86, 8227 (1989), *Genes Develop.,* 4, 1288 (1990)], or the methods described in Japanese Published Unexamined Patent Application No. 336963/93, WO 94/23021 and the like.

That is, the polypeptide of the present invention can be positively secreted extracellularly from a host cell by expressing it in a form in which a signal peptide is added to the upstream of a polypeptide containing active region of the polypeptide of the present invention, using gene recombination techniques.

Specifically, it is considered that the polypeptide of the present invention can be positively secreted extracellularly from a host cell by adding a signal peptide to the upstream of a polypeptide having an amino acid sequence presumably containing a catalytic region and expressing the product. In addition, a tag for the purification and detection can be added between the signal peptide and the catalytic region or to the C-terminal of a polypeptide containing the catalytic region.

Examples of the tag for the purification and detection include β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA binding protein domain, Tac antigen, thioredoxin, green fluorescent protein, FLAG peptide, epitopes of antibodies of interest and the like [Akio Yamakawa, *Jikken Igaku,* 13, 469-474 (1995)].

Moreover, its production can be increased according to the method described in Japanese Published Unexamined Patent Application No. 227075/90 using a gene amplification system in which a dihydrofolate reductase gene or the like is used.

As other methods for producing the polypeptide of the present invention, a production method by a in vitro transcription-translation system using the DNA of the present invention is exemplified. The in vitro transcription-translation system means a system in which a polypeptide is produced by transcribing from DNA to mRNA and translating from the mRNA to a protein using a cell-free system. Any system can be used, so long as it is a cell-free system in which an objective polypeptide can be produced from an objective DNA or an objective mRNA. Typical cell-free translation systems include a system using rabbit reticulocyte lysate or wheat germ lysate, and the like. The in vitro transcription-translation system is commercially available as a kit from various manufactures, and a polypeptide can be relatively easily produced by using the commercially available kits. The commercially available kits include In Vitro Express™ Translation Kit (manufactured by STRATAGENE). Furthermore, the polypeptide of the present invention can also be produced by using an in vitro transcription-translation system according to the known method [*J. Biomolecular NMR*, 6, 129-134, *Science*, 242, 1162-1164, *J. Biochem.*, 110, 166-168 (1991)].

General enzyme isolation purification methods can be used for isolating and purifying the polypeptides of the present invention from a culture of a transformant for producing the polypeptide of the present invention. For example, when the polypeptide of the present invention is accumulated in a soluble state inside the cells of the transformant for producing the polypeptide of the present invention, the cells in the culture are collected by centrifugation, the cells are washed and then the cells are disrupted using a sonicator, French press, Manton Gaulin homogenizer, dynomill or the like to obtain a cell-free extract.

A purified product can be obtained from a supernatant prepared by centrifuging the cell-free extract, by employing techniques, such as solvent extraction, salting out and desalting with ammonium sulfate or the like, precipitation with organic solvents, anion exchange chromatography using a resin such as diethylaminoethyl (DEAE)-Sepharose or DIAION HPA-75 (manufactured by Mitsubishi Chemical), cation exchange chromatography using a resin such as S-Sepharose FF (manufactured by Pharmacia), hydrophobic chromatography using a resin such as butyl-Sepharose or phenyl-Sepharose, gel filtration using a molecular sieve, affinity chromatography, chromatofocusing and electrophoresis such as isoelectric focusing.

Also, when the polypeptide is expressed inside the cells in the form of an insoluble body, the cells are recovered, disrupted and centrifuged in the same manner, the polypeptide is recovered from the thus obtained precipitated fraction in the usual way and then the insoluble bodies of the polypeptide are solubilized using a protein denaturing agent. The polypeptide is refolded into normal stereostructure by diluting or dialyzing the solubilized solution to or against a solution which does not contain the protein denaturing agent or contains the protein denaturing agent but in such a low concentration that the protein is not denatured, and then its purified product is obtained by the above isolation purification method.

When the polypeptide is secreted extracellularly, the culture is treated by centrifugation or the like means to obtain a soluble fraction. A purified preparation of the polypeptide can be obtained from the soluble fraction by a method similar to the above method for its isolation and purification from a cell-free extract supernatant.

Also, it can be purified according to the purification method of general glycosyltransferase [*Methods in Enzymology*, 83, 458].

Furthermore, the polypeptide of the present invention can be purified by producing it as a fusion protein with other protein and then treating the product with affinity chromatography in which a substance having affinity for the fused protein is used [Akio Yamakawa, *Jikken Igaku*, 13, 469-474 (1995)]. For example, the polypeptide of the present invention can be purified by producing it as a fusion protein with protein A and then treating the fusion protein with affinity chromatography in which immunoglobulin G is used, according to the method of Lowe et al. [*Proc. Natl. Acad. Sci. USA*, 86, 8227 (1989), *Genes Dev.*, 4, 1288 (1990)] or the method described in Japanese Published Unexamined Patent Application No. 336963/93 or WO 94/23021. Also, the polypeptide of the present invention can be purified by producing it as a fusion protein with FLAG peptide and then treating the product with an affinity chromatography in which an anti-FLAG antibody is used [*Proc. Natl. Acad. Sci. USA*, 86, 8227 (1989), *Genes Develop.*, 4, 1288 (1990)].

Furthermore, it can also be purified by affinity chromatography in which an antibody for the polypeptide itself is used.

Moreover, the polypeptide of the present invention can also be produced by a chemical synthesis method such as Fmoc method (fluorenylmethyloxycarbonyl method) or tBoc method (t-butyloxycarbonyl method). Also, it can be chemically synthesized by use of a peptide synthesizer manufactured, e.g., by Advanced ChemTech, PERKIN ELMER, Pharmacia Biotech, Protein Technology Instrument, Synthecell-Vega, PerSeptive, Shimadzu or the like.

The purified polypeptide of the present invention can be structurally analyzed by a method generally used in protein chemistry, such as the method described in *Protein Structure Analysis for Gene Cloning* (*Idenshi Cloning No Tameno Tanpakushitsu Kozo Kaiseki*) (edited by H. Hirano, published by Tokyo Kagaku Dojin, 1993).

(3) Activity Measurement and Application of the Polypeptide of the Present Invention The β1,3-N-acetylglucosaminyltransferase activity of the polypeptide of the present invention can be measured using a cell extract prepared from a transformant carrying an expression vector for the polypeptide of the present invention or the polypeptide of the present invention isolated and purified from the transformant or a cultured product thereof as the enzyme sample, based on a known measuring method [*J. Biol. Chem.*, 268, 27118 (1993), *J. Biol. Chem.*, 267, 23507 (1992), *J. Biol. Chem.*, 267, 2994 (1992), *J. Biol. Chem.*, 263, 12461 (1988), *Jpn. J. Med. Sci. Biol.*, 42, 77 (1989), *FEBS Lett.*, 462, 289 (4999), *J. Biol. Chem.*, 269, 14730-14737 (1994), *J. Biol. Chem.*, 267, 2994 (1992), *Anal. Biochem.*, 189, 151-162 (1990), *J. Biol. Chem.*, 273, 433-440 (1998)]. Also, acceptor specificity of the polypeptide of the present invention can be examined by measurement using various acceptors.

When a cell extract is used as an enzyme sample, in order to eliminate influence of the glycosyltransferase activities possessed by the host cell itself, a cell extract of a transformant transfected with a control vector which does not contain a DNA encoding the polypeptide of the present invention is used as a control and its β1,3-N-acetylglucosaminyltransferase activity is compared. When β1,3-N-acetylglucosaminyltransferase activity is increased in comparison with the control, it can be said that the polypeptide encoded by the DNA of the present invention carried by the transformant has a β1,3-N-acetylglucosaminyltransferase activity.

In the case of a cell or tissue expressing two or more Gal β1,3-N-acetylglucosaminyltransferases, each of the Gal β1,3-N-acetylglucosaminyltransferases cannot be specified and enzymological characteristics of each of these Gal β1,3-N-acetylglucosaminyltransferases cannot be elucidated by enzymological analysis using a cell or tissue extract. By purifying the polypeptide of the present invention by the method described in (2), enzymological characteristics of the Gal β1,3-N-acetylglucosaminyltransferase possessed by the polypeptide can be found.

Examples of the measuring method are shown below.

(i) Method Using a Fluorescently-Labeled Oligosaccharide as the Acceptor

The reaction is carried out using an oligosaccharide fluorescently-labeled by 2-aminobenzamide-labeling or pyridylamination as an acceptor and UDP-GlcNAc as a saccharide donor, and the reaction solution is analyzed by high performance liquid chromatography (HPLC). The 2-aminobenzamide-labeled sugar chain substrate can be prepared using SIGMA 2AB glycan labeling kit (manufactured by Oxford Glycoscience) according to the manufacture's instructions attached to the kit. The fluorescence-labeling by pyridylamination can be carried out in a conventional manner [*Agric. Biol. Chem.*, 54, 2169 (1990)]. A peak which increases when the saccharide donor UDP-GlcNAc is added, in comparison with the case of no addition, is considered as a peak of a product. The amount of the product is determined based on its fluorescence intensity, and a ratio of the product to the added acceptor is used as a β1,3-N-acetylglucosaminyltransferase activity. The product can be identified by coincidence of the HPLC retention time of the product with the retention time of a standard (a labeled oligosaccharide having structure in which N-acetylglucosamine is added via β1,3-linkage to the reducing terminal of the acceptor oligosaccharide used in the reaction) as the index.

(ii) Method Using an Unlabeled Oligosaccharide as the Acceptor

A reaction is carried out using an unlabeled oligosaccharide as an acceptor in the same manner as in (i) and the reaction solution is analyzed by a high speed anion exchange chromatography instead of HPLC. Using a peak with the increase amount when the saccharide donor UDP-GlcNAc is added, in comparison with the case of no addition, as a peak of a product, an amount of the product is measured, and a ratio of the product to the added acceptor is used as a β1,3-N-acetylglucosaminyltransferase activity. The formed product can be identified by coincidence of the elution time of the formed product by the high speed anion exchange chromatography with the elution time of a standard (an oligosaccharide having structure in which N-acetylglucosamine is added via β1,3-linkage to the reducing terminal of the acceptor oligosaccharide used in the reaction) as the index.

(iii) Method Using a Glycolipid as the Acceptor

A reaction is carried out using a glycolipid as an acceptor and UDP—[$^{14}$C]GlcNAc as a saccharide donor. Glycolipids are extracted from the reaction solution by a reverse phase chromatography and developed using a silica gel thin layer chromatography (TLC). The product is detected and quantified by measuring radioactivity on the plate. A ratio of the product to the added acceptor is used as a β1,3-N-acetylglucosaminyltransferase activity. The formed product can be identified by coincidence of the Rf value of the product with the Rf value of a standard (a glycolipid having structure in which N-acetylglucosamine is added via β1,3-linkage to the reducing terminal of the glycolipid used as the acceptor) as the index.

Also, whether or not the polypeptide of the present invention is involved in the in vivo sugar chain synthesis can be analyzed as follows. Based on the description in (2), cells of a transformant prepared by introducing an expression vector containing the DNA of the present invention into animal cells are cultured to express the polypeptide of the present invention. The transformant cells are subjected to a fluorescent staining using antibodies or lectins capable of binding specifically to various sugar chains (poly-N-acetyllactosamine sugar chain, sialyl Lewis a sugar chain and sialyl Lewis c sugar chain), and then amounts of sugar chains to which the antibodies or lectins bind are measured using a fluorescence activated cell sorter (hereinafter referred to as "FACS").

For example, as a result of confirming increase of the amount of poly-N-acetyllactosamine sugar chain in comparison with a transformant cell transfected with a control vector which does not contain a DNA encoding the polypeptide of the present invention, it can be found that the polypeptide encoded by the DNA of the present invention has a β1,3-N-acetylglucosaminyltransferase activity involved in the synthesis of a poly-N-acetyllactosamine sugar chain.

As antibodies or lectins which recognize a poly-N-acetyllactosamine sugar chain, any antibody or lectin can be used, so long as it recognizes a poly-N-acetyllactosamine sugar chain. For example, an anti-i antibody which specifically recognizes a linear poly-N-acetyllactosamine sugar chain (i antigen) and an anti-I antibody which specifically recognizes a branched poly-N-acetyllactosamine sugar chain (I antigen) [*J. Biol. Chem.*, 254, 3221 (1979)] can be used as antibodies which specifically recognize a poly-N-acetyllactosamine sugar chain, and pokeweed mitogen (hereinafter referred to as "PWM"), *Lycopersicon esculentum* agglutinin (hereinafter referred to as "LEA") and *Datura stramonium* agglutinin (hereinafter referred to as "DSA") can be used as lectins which specifically recognize a poly-N-acetyllactosamine sugar chain [*J. Biol. Chem.*, 282, 8179-8189 (1987), *J. Biol. Chem.*, 259, 6253-6260 (1984), *J. Biol. Chem.*, 262, 1602-1607 (1987), *Carbohydr. Res.*, 120, 187-195 (1983), *Carbohydr. Res.*, 120, 283-292 (1983), *Glycoconjugate J.*, 7, 323-334 (1990)].

Involvement of the polypeptide of the present invention in the in vivo synthesis of sugar chains of complex carbohydrates such as glycoproteins and glycolipids can be confirmed by adding a sugar chain synthesis inhibitor specific for the sugar chain of respective complex carbohydrates at the time of the culturing of the transformant cells in the above method, and then subjecting the cells in which synthesis of the sugar chain was inhibited to FACS analysis. For example, it can be found that the polypeptide of the present invention is involved in the synthesis of a poly-N-acetyllactosamine sugar chain in O-linked sugar chains of glycoprotein, if the amount of poly-N-acetyllactosamine sugar chain is reduced when transformant cells are fluorescently-stained using an antibody which recognizes a poly-N-acetyllactosamine sugar chain and then analyzed by FACS, after culturing of the transformant cells in the presence of an inhibitor specific for the synthesis of O-linked sugar chains of glycoprotein.

Examples of the sugar chain synthesis inhibitor specific for the sugar chains of complex carbohydrates include Benzyl-α-GalNAc which is a synthesis inhibitor of glycoprotein O-linked sugar chains, a mannosidase II inhibitor swainsonine which acts as a synthesis inhibitor of glycoprotein N-linked sugar chains, and a glucosylceramide synthase inhibitor D-PDMP (D-threo-1-phenyl-2-decanoylamino-3-morpholino-1-propanol) which acts as a synthesis inhibitor of glycolipid sugar chains.

Also, involvement of the polypeptide of the present invention in the synthesis of glycolipid sugar chains can be confirmed by extracting glycolipids from a transformant cell prepared by introducing an expression vector for the polypeptide of the present invention into an animal cell and from a transformant cell prepared by introducing a control vector which does not contain a DNA encoding the polypeptide of the present invention, and analyzing and comparing compositions of both glycolipids using a TLC plate. Extraction of glycolipids and analysis of compositions can be carried out according to a known method [Shujunsha, *Cell Technology (Saibo Kogaku)*, Supplement, "Glycobiology Experiment Protocol (Glycobiology Jikken Protocol)"; *Anal. Biochem.*, 223, 232 (1994)]. The glycolipid developed on a TLC plate is detected and quantified by orcinol staining or immunostaining which involves use of an antibody capable of binding to specific sugar chain structure and identified by comparing with the Rf value of a standard glycolipid. For example, it can be found that the polypeptide of the present invention is involved in the synthesis of paragloboside (Galβ1-4GlcNAcβ1-3Galβ1-4Glc-ceramide) and neolactohexaosylceramide (Galβ1-4GlcNAcβ1-3Galβ1-4GlcNAcβ1-3Galβ1-4Glc-ceramide), if the amounts of paragloboside and neolactohexaosylceramide are increased in a transformant cell in which the polypeptide of the present invention is expressed, in comparison with a control transformant cell, when paragloboside and neolactohexaosylceramide are detected by immunostaining involving use of an antibody which recognizes the N-acetyllactosamine structure.

The polypeptide of the present invention can be used as medicaments for treating, preventing and/or diagnosing diseases which accompany changes in the expression of the polypeptide of the present invention such as inflammatory disease, cancer and tumor metastasis.

Although the medicament comprising the polypeptide of the present invention can be used directly as a therapeutic agent, generally, it is preferred to use it as a pharmaceutical preparation produced by a well-known method in the technical field of pharmaceutics by mixing it with at least one pharmaceutically acceptable carrier. As the administration method of the therapeutic agent, it is preferred to use the most effective method in carrying out the treatment, and methods by oral administration or by parenteral administration such as buccal, airway, rectal, subcutaneous, intramuscular or intravenous can be used. A dosage form of the therapeutic drug include ointments, sprays, capsules, tablets, granules, syrups, emulsions, suppositories injections, tapes and the like.

The preparations suitable for oral administration include emulsions, syrups, capsules, tablets, powders, granules and the like. For example, liquid preparations such as emulsions and syrups can be produced using, as additives, water; saccharides such as sucrose, sorbitol and fructose; glycols such as polyethylene glycol and propylene glycol; oils such as sesame oil, olive oil and soybean oil; antiseptics such as p-hydroxybenzoates; flavors such as strawberry flavor and peppermint; and the like. Capsules, tablets, powders, granules and the like can be produced using, as additives, fillers such as lactose, glucose, sucrose and mannitol; disintegrants such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The preparations suitable for parenteral administration include injections, suppositories, sprays and the like. For example, injections can be prepared using, for example, a carrier comprising a salt solution, a glucose solution, or a mixture of both or the like. Suppositories can be produced using, for example, a carrier such as cacao butter, hydrogenated fat or carboxylic acid. Also, sprays can be prepared from the protein itself or using a carrier or the like which does not stimulate oral and airway mucous membranes of patients and can facilitate absorption of the protein by dispersing it as minute particles. The carrier includes lactose, glycerol and the like. Depending on the properties of the protein and the carrier, it is possible to prepare pharmaceutical preparations such as aerosols and dry powders. The components exemplified as additives of oral preparations can also be added to these parenteral preparations.

The dose or frequency of administration varies depending on the intended therapeutic effect, administration method, treating period, age, body weight and the like, but is generally from 1 μg/kg to 100 mg/kg per day and per adult.

Furthermore, now that a polypeptide of the present invention having a lactosylceramide β1,3-N-acetylglucosaminyltransferase activity and a DNA encoding the polypeptide have been obtained, functional analyses and applications as shown below become possible.

(i) Functional analysis of the polypeptide of the present invention by molecular biological techniques or using a knockout mouse, a transgenic mouse or the like.

(ii) Expression distribution analysis of the polypeptide of the present invention and DNA encoding the polypeptide.

(iii) Analysis of relationship of expression of the polypeptide of the present invention and DNA encoding the polypeptide with various diseases.

(iv) Diagnosis of diseases using expression of the polypeptide of the present invention and DNA encoding the polypeptide as the marker.

(v) Identification of type and differentiation stage of cells using expression of the polypeptide of the present invention and DNA encoding the polypeptide as a marker.

(vi) Screening of a compound which increases or inhibits expression of the polypeptide of the present invention and DNA encoding the polypeptide or enzyme activity possessed by the polypeptide of the present invention.

(vii) Synthesis of useful sugar chains using the polypeptide of the present invention.

Examples of the use of the polypeptide of the present invention and DNA encoding the polypeptide are specifically described as follows.

(4) Production and Application of a Sugar Chain Having Structure in which N-acetylglucosamine is Added to Galactose Residue via β1,3-linkage and Complex Carbohydrate Containing the Sugar Chain The polypeptide of the present invention has an activity to transfer N-acetylglucosamine via β1,3-linkage to galactose residue present in the non-reducing terminal of an acceptor sugar chain, namely β1,3-N-acetylglucosaminyltransferase activity. Accordingly, the polypeptide of the present invention can be used as a sugar chain synthesizing agent. Examples of acceptors include i) galactose, N-acetyllactosamine (Galβ1-4GlcNAc), Galβ1-3GlcNAc or lactose (Galβ1-4Glc), ii) an oligosaccharide having galactose, N-acetyllactosamine, Galβ1-3GlcNAc or lactose structure in the non-reducing terminal, and iii) a complex carbohydrate having galactose, N-acetyllactosamine, Galβ1-3GlcNAc or lactose structure in the non-reducing terminal. The polypeptide of the present invention has an enzyme activity to transfer N-acetylglucosamine via β1,3-linkage to galactose residue present in the non-reducing terminal of an acceptor sugar chain selected from the above i) to iii). The complex carbohydrate includes a complex carbohydrate selected from a glycoprotein, a glycolipid, a proteoglycan, a glycopeptide, a lipopolysaccharide, a peptidoglycan, a glycoside in which a sugar chain is linked to a steroid compound and the like. Examples of the complex carbohydrate having galactose, N-acetyllactosamine, Galβ1-3GlcNAc or lactose structure in the non-reducing terminal include lactosylceramide, paragloboside and the like.

Examples of the structure in which N-acetylglucosamine is added to a galactose residue via β1,3-linkage include GlcNAcβ1-3Gal structure, GlcNAcβ1-3Galβ1-4GlcNAc structure, GlcNAcβ1-3Galβ1-3GlcNAc structure, GlcNAcβ1-3Galβ1-4Glc structure, (Galβ1-4GlcNAcβ1-3)$_n$ Galβ1-4GlcNAc structure (n is an integer of 1 or more), (Galβ1-4GlcNAcβ1-3)$_n$Galβ1-4Glc structure (n is an integer of 1 or more) and the like.

The details are shown as follows.

(i) Process for Producing a Sugar Chain Using Transformant Transfected with DNA Encoding the Polypeptide of the Present Invention A sugar chain having structure in which N-acetylglucosamine is added to a galactose residue via β1,3-linkage, specifically a sugar chain comprising a saccharide selected from the group consisting of GlcNAcβ1-3Galβ1-4Glc-ceramide, a lacto-series glycolipid (a glycolipid having Galβ1-3GlcNAcβ1-3Galβ1-4Glc-ceramide as a backbone), a neolacto-series glycolipid (a glycolipid having Galβ1-4GlcNAcβ1-3Galβ1-4Glc-ceramide as a backbone), a saccharide having a GlcNAcβ1-3Gal structure, a saccharide having GlcNAcβ1-3Galβ1-4GlcNAc structure, a saccharide having GlcNAcβ1-3Galβ1-3GlcNAc structure, a saccharide having GlcNAcβ1-3Galβ1-4Glc structure, a saccharide having (Galβ1-4GlcNAcβ1-3)$_n$Galβ1-4GlcNAc structure wherein n is 1 or more and a saccharide having (Galβ1-4GlcNAcβ1-3)$_n$Galβ1-4Glc structure wherein n is 1 or more, or a complex carbohydrate containing the above sugar chain, can be produced by culturing a transformant selected from transformants obtained in the above (3) from microorganisms, animal cells, plant cells and insect cells, in a culture medium to produce and accumulate the sugar chain or complex carbohydrate, and then recovering the sugar chain or complex carbohydrate from the culture mixture.

The culturing can be carried out according to the above (3). A sugar chain having structure in which N-acetylglucosamine is added to a galactose residue via β1,3-linkage can be added to the recombinant glycoprotein by simultaneously producing the polypeptide of the present invention and a recombinant glycoprotein of interest (e.g., a recombinant glycoprotein for medicament) in a transformant capable of synthesizing sugar chains among the above transformants.

(ii) Process for Producing a Sugar Chain Using an Animal or Plant into which DNA Encoding the Polypeptide of the Present Invention is Introduced Using an animal or plant obtained in the above (3), a sugar chain having structure in which N-acetylglucosamine is added to a galactose residue via β1,3-linkage or a complex carbohydrate to which the sugar chain is added can be produced according to the process of above (3).

That is, a sugar chain having structure in which N-acetylglucosamine is added to a galactose residue via β1,3-linkage or a complex carbohydrate to which the sugar chain is added, specifically GlcNAcβ1-3Galβ1-4Glc-ceramide, a lacto-series glycolipid (a glycolipid having Galβ1-3GlcNAcβ1-3Galβ1-4Glc-ceramide as a backbone), a neolacto-series glycolipid (a glycolipid having Galβ1-4GlcNAcβ1-3Galβ1-4Glc-ceramide as a backbone), a sugar chain comprising a saccharide selected from the group consisting of a saccharide having GlcNAcβ1-3Gal structure, a saccharide having GlcNAcβ1-3Galβ1-4GlcNAc structure, a saccharide having GlcNAcβ1-3Galβ1-3GlcNAc structure, a saccharide having GlcNAcβ1-3Galβ1-4Glc structure, a saccharide having (Galβ1-4GlcNAcβ1-3)$_n$Galβ1-4GlcNAc structure wherein n is 1 or more and a saccharide having (Galβ1-4GlcNAcβ1-3)$_n$Galβ1-4Glc structure wherein n is 1 or more, or a complex carbohydrate containing the above sugar chain, can be produced by breeding a non-human transgenic animal carrying the DNA of the present invention to produce and accumulate the sugar chain or complex carbohydrate containing the sugar chain, and then recovering the product from the animal.

The sugar chain or complex carbohydrate can be produced and accumulated, for example, in milk, egg and the like of the animal.

In the case of a plant, a sugar chain having structure in which N-acetylglucosamine is added to a galactose residue via β1,3-linkage or a complex carbohydrate to which the sugar chain is added can be produced, for example, by cultivating a transgenic plant comprising the DNA of the present invention to produce and accumulate the sugar chain having structure in which N-acetylglucosamine is added to a galactose residue via β1,3-linkage or complex carbohydrate to which the sugar chain is added, and then recovering the product from the plant.

(iii) Process for Producing a Sugar Chain Using the Polypeptide of the Present Invention Using the polypeptide of the present invention obtained by the process described in the above (3) as an enzyme source, and galactose, an oligosaccharide having a galactose residue in the non-reducing terminal or a complex carbohydrate having a galactose residue in the non-reducing terminal of its sugar chain as an acceptor, a reaction product in which N-acetylglucosamine is added via β1,3-linkage to galactose or a galactose residue present in the non-reducing terminal of the sugar chain can be produced in an aqueous medium by the following process.

That is, a reaction product in which N-acetylglucosamine is added via β1,3-linkage to galactose or a galactose residue of an acceptor can be produced by using at least one species selected from the group consisting of i) lactosylceramide (Galβ1-4Glc-ceramide) or paragloboside (Galβ1-4GlcNAcβ1-3Galβ1-4Glc-ceramide), ii) galactose, N-acetyllactosamine (Galβ1-4GlcNAc), Galβ1-3GlcNAc, Galβ1-3GalNAc or lactose (Galβ1-4Glc), iii) an oligosaccharide having galactose, N-acetyllactosamine (Galβ1-4GlcNAc), Galβ1-3GlcNAc or lactose (Galβ1-4Glc) structure in the non-reducing terminal, and iv) a complex carbohydrate having galactose, N-acetyllactosamine, Galβ1-3GlcNAc or lactose structure in the non-reducing terminal, as an acceptor, and the polypeptide of the present invention obtained by the process described in the above (3) as an enzyme source, allowing the acceptor, the enzyme source and N-acetylglucosamine uridine 5'-diphosphate (to be referred to as UDP-GlcNAc hereinafter) to be present in an aqueous medium to produce and accumulate the reaction product, and then recovering the reaction product from the aqueous medium.

The enzyme source is used at a concentration of 0.1 mU/l to 10,000 U/l, preferably 1 mU/l to 1,000 U/l, by defining the activity capable of forming 1 μmol of GlcNAcβ1-3Galβ1-4GlcNAcβ1-3Galβ1-4Glc in 1 minute at 37° C. as 1 unit (U) when lacto-N-neotetraose (Galβ1-4GlcNAcβ1-3Galβ1-4Glc) is used as the substrate.

Examples of the aqueous media include water, buffer solutions such as phosphate buffer, carbonate buffer, acetate buffer, borate buffer, citrate buffer and tris buffer, alcohols such as methanol and ethanol, esters such as ethyl acetate, ketones such as acetone, amides such as acetamide, and the like. A culture medium of a microorganism used as an enzyme source can also be used as the aqueous medium. In addition, the culture medium of a transformant obtained by the culturing described in the above (2) or the milk obtained from a non-human transgenic animal described in the above (2) can also be used as the aqueous medium. If necessary, a surfactant or an organic solvent may be added to the aqueous medium.

The surfactant may be any agent that can accelerate production of a sugar chain having structure in which N-acetylglucosamine is added to a galactose residue via β1,3-linkage or a complex carbohydrate to which the sugar chain is added. Examples include nonionic surfactants such as polyoxyethylene octadecylamine (e.g., Nymeen S-215, manufactured by NIPPON OIL & FATS), cationic surfactants such as cetyltrimethylammonium bromide and alkyldimethyl benzylammonium chloride (e.g., Cation F2-40E, manufactured by NIPPON OIL & FATS), anionic surfactants such as lauryl sarcosinate, tertiary amines such as alkyl dimethylamine (e.g., Tertiary Amine FB, manufactured by NIPPON OIL & FATS), and the like, which may be used alone or as a mixture of two or more thereof. The surfactant is generally used at a concentration of 0.1 to 50 g/l.

The organic solvent includes xylene, toluene, an aliphatic alcohol, acetone, ethyl acetate and the like, and it is generally used at a concentration of 0.1 to 50 ml/l. As the UDP-GlcNAc, a reaction solution produced by using activity of a microorganism or the like or a product purified from the reaction solution can be used, in addition to commercially available products. The UDP-GlcNAc is used at a concentration of 0.1 to 500 mmol/l.

Examples of the oligosaccharides having galactose, N-acetyllactosamine (Galβ1-4GlcNAc), Galβ1-3GlcNAc or lactose (Galβ1-4Glc) structure in the non-reducing terminal, other than those described above, include Galβ1-3GalNAc, Galβ1-4GlcNAcβ1-3Galβ1-4Glc, Galβ1-4GlcNAcβ1-3Galβ1-4GlcNAc, Galβ1-4(Fucα1-3)GlcNAcβ1-3Galβ1-4Glc, Galβ1-4(Fucα1-3)GlcNAcβ1-3Galβ1-4GlcNac, Galβ1-4GlcNAcβ1-3Galβ1-4(Fucα1-3)Glc, Galβ1-4GlcNAcβ1-3Galβ1-4(Fucα1-3)GlcNAc, Galβ1-3GlcNAcβ1-3Galβ1-4Glc, Galβ1-3GlcNAcβ1-3Galβ1-4GlcNAc, Galβ1-3GlcNAcβ1-3Galβ1-4(Fucα1-3)Glc, Galβ1-3GlcNAcβ1-3Galβ1-4(Fucα1-3)GlcNAc, Galβ1-4GlcNAcβ1-3(GlcNAcβ1-6)Galβ1-4Glc, Galβ1-4GlcNAcβ1-3(GlcNAcβ1-6)Galβ1-4GlcNAc, Galβ1-4GlcNAcβ1-3(Galβ1-4GlcNAcβ1-6)Galβ1-4Glc, Galβ1-4GlcNAcβ1-3(Galβ1-4GlcNAcβ1-6)Galβ1-4GlcNAc, Galβ1-3GlcNAcβ1-3(GlcNAcβ1-6)Galβ1-4Glc, Galβ1-3GlcNAcβ1-3(GlcNAcβ1-6)Galβ1-4GlcNAc, Galβ1-3GlcNAcβ1-3(Galβ1-4GlcNAcβ1-6)Galβ1-4Glc and Galβ1-3GlcNAcβ1-3(Galβ1-4GlcNAcβ1-6)Galβ1-4GlcNAc, or an oligosaccharide having structure of any one of these oligosaccharide structures in the non-reducing terminal of the sugar chain. The complex carbohydrates having a galactose residue in the non-reducing terminal of its sugar chain include a complex carbohydrate containing a sugar chain having structure of any one the above oligosaccharide structure in the non-reducing terminal of the sugar chain, a complex carbohydrate containing an asialo complex N-linked sugar chain and the like. Specific examples include glycolipids such as lactosylceramide (Galβ1-4Glc-ceramide) and paragloboside (Galβ1-4GlcNAcβ1-3Galβ1-4Glc-ceramide).

The acceptor can be used at a concentration of 0.01 to 500 mmol/l.

In the production reaction, inorganic salts such as $MnCl_2$, β-mercaptoethanol, polyethylene glycol and the like can be added as the occasion demands. The production reaction is carried out in an aqueous medium at pH 5 to 10, preferably pH 6 to 8, and at 20 to 50° C. for 1 to 96 hours.

A part of a sugar chain can be cut out from the sugar chain or complex carbohydrate produced by the above process by known enzymatic techniques or chemical techniques [*Second Biochemical Experimentation Series* (Zoku Seikagaku Jikken Koza), Vol. 4, "Method for Studying Complex Carbohydrates (Fukugo Toshitsu Kenkyu-ho)" I, II, edited by Japanese Biochemical Society, Tokyo Kagaku Dojin (1986), *Glycobiology Experimentation Protocol* (Glycobiology Jikken Protocol), edited by Naoyuki Taniguchi, Akemi Suzuki, Kiyoshi Furukawa and Kazuyuki Sugawara, Shujun-sha, (1996)].

A galactose-added sugar chain or complex carbohydrate can be produced using the N-acetylglucosamine-added sugar chain or complex carbohydrate obtained by the above process as an acceptor and by allowing a) the acceptor, b) GlcNAc β1,4-galactosyltransferase and c) uridine 5'-diphosphate galactose (hereinafter referred to as "UDP-Gal") to be present in an aqueous medium to produce and accumulate a reaction product in which the galactose is added via β1,4-linkage to the N-acetylglucosamine residue at the non-reducing terminal of the acceptor in the aqueous medium, and recovering the galactose-added sugar chain or complex carbohydrate from the aqueous medium.

In addition, it is known that a poly-N-acetyllactosamine sugar chain [a sugar chain constructed by two or more repetition of (Galβ1-4GlcNAcβ1-3) structure] is synthesized by repetitive action of a GlcNAc β1,4-galactosyltransferase and a Gal β1,3-N-acetylglucosaminyltransferase. Thus, the poly-N-acetyllactosamine sugar chain can be synthesized in vitro using GlcNAc β1,4-galactosyltransferase and the polypeptide of the present invention having a Gal β1,3-N-acetylglucosaminyltransferase activity.

That is, a poly-N-acetyllactosamine sugar chain-added sugar chain or complex carbohydrate can be produced using the polypeptide of the present invention as an enzyme source, by allowing (a) GlcNAc β1,4-galactosyltransferase, (b) an acceptor selected from i) lactosylceramide (Galβ1-4Glc-ceramide) or paragloboside (Galβ1-4GlcNAcβ1-3Galβ1-4Glc-ceramide), ii) galactose, N-acetyllactosamine (Galβ1-4GlcNAc), Galβ1-3GlcNAc or lactose (Galβ1-4Glc), iii) an oligosaccharide having galactose, N-acetyllactosamine (Galβ1-4GlcNAc), Galβ1-3GlcNAc or lactose (Galβ1-4Glc) structure in the non-reducing terminal, iv) a complex carbohydrate having galactose, N-acetyllactosamine, Galβ1-3GlcNAc or lactose structure in the non-reducing terminal and v) a sugar chain or complex carbohydrate obtained by the process described above, (c) uridine 5'-diphosphate N-acetylglucosamine (UDP-GlcNAc), and (d) uridine 5'-diphosphate galactose (UDP-Gal) to be present in an aqueous medium to produce and accumulate a reaction product in which a poly-N-acetyllactosamine sugar chain is added to the non-reducing terminal of the acceptor in the aqueous medium, and recovering the poly-N-acetyllactosamine sugar chain-added sugar chain or complex carbohydrate from the aqueous medium.

Furthermore, a poly-N-acetyllactosamine sugar chain or a complex carbohydrate to which the sugar chain is added can be produced by co-expressing a GlcNAc β1,4-galactosyltransferase and a DNA encoding the polypeptide of the present invention having a Gal β1,3-N-acetylglucosaminyltransferase activity in a cell. Since GlcNAc β1,4-galactosyltransferase is expressed in almost all cells, a poly-N-acetyllactosamine sugar chain or a complex carbohydrate to which the sugar chain is added can also be produced by expressing the DNA encoding the polypeptide of the present invention having a Gal β1,3-N-acetylglucosaminyltransferase activity alone in a cell.

(iv) Applications of Various Sugar Chains or Complex Carbohydrates

For example, the following applications can be considered as applications of the thus produced various sugar chains or complex carbohydrates.

It is known that lacto-N-neotetraose (Galβ1-4GlcNAcβ1-3Galβ1-4Glc) and lacto-N-tetraose (Galβ1-3GlcNAcβ1-3Galβ1-4Glc) or various oligosaccharides having them as a backbone are present in human milk [*Acta Paediatrica*, 82, 903 (1993)]. The oligosaccharides have GlcNAcβ1-3Gal structure in common. Also, oligosaccharides having a poly-N-acetyllactosamine sugar chain are included in the oligosaccharides. It is considered that these oligosaccharides function to prevent babies from infection with viruses and microorganisms or to neutralize toxins. In addition, their activity to accelerate growth of *Lactobacillus bifidus* which is a beneficial enteric bacterium is also known. On the other hand, types of oligosaccharides existing in the milk of animals such as cows and mice are few and are mostly lactose, and the above oligosaccharides existing in human milk are hardly present therein.

It may be industrially markedly useful if the above oligosaccharides contained in human milk or a milk containing them can be produced efficiently. Since there is a possibility that the polypeptide of the present invention having a lactosylceramide β1,3-N-acetylglucosaminyltransferase activity is involved in the synthesis of the above oligosaccharides contained in human milk at mammary gland, there is a possibility that it can be used in the production of oligosaccharides effective in treating infectious diseases and accelerating growth of the beneficial *Lactobacillus bifidus*.

Since a poly-N-acetyllactosamine sugar chain contributes to the stabilization of proteins, any protein can be stabilized by artificially adding a poly-N-acetyllactosamine sugar chain to the protein. Also, since the clearance rate of a blood protein from the kidney becomes slow as the effective molecular weight of the protein increases, stability of any protein in blood can be increased through its reduced clearance rate from the kidney by increasing its effective molecular weight by artificially adding a poly-N-acetyllactosamine sugar chain to the protein. Also, targeting of any protein of interest into a specified cell can be carried out by adding a poly-N-acetyllactosamine sugar chain.

(5) Application of the DNA or Oligonucleotide of the Present Invention

Applications using the DNA or oligonucleotide of the present invention or derivatives thereof are described below in detail.

(i) Determination of the Expression Level of a DNA Encoding the Polypeptide of the Present Invention Determination of the expression level of a gene encoding the polypeptide of the present invention or detection of structural change of the gene can be carried out by using the DNA of the present invention or the above oligonucleotide prepared from the DNA.

The method for determining expression level of mRNA encoding the polypeptide of the present invention or detecting structural changes of DNA and mRNA encoding the polypeptide of the present invention includes (a) Northern blotting, (b) in situ hybridization, (c) quantitative PCR/real time PCR, (d) differential hybridization, (e) DNA micro-array/DNA tip, (f) RNase protection assay and the like.

As the samples to be analyzed by the above methods, DNA, mRNA or total RNA obtained from cultured cells, various tissues, biological samples such as sera and saliva, or the transformants described in (3) are used. Hereinafter, the mRNA and total RNA are called sample-derived RNA. In addition, samples isolated as paraffin or cryostat sections from tissues obtained from biological samples can also be used.

In the Northern blotting, the expression level of an mRNA and its structural change can be detected by detecting a band specifically binding to the mRNA encoding the polypeptide of the present invention, by separating sample-derived RNA by gel electrophoresis, transferring the sample onto a support such as a nylon filter, and then carrying out hybridization using a labeled probe prepared from the DNA of the present invention and washing. In the hybridization, incubation is performed under such conditions that the mRNA in the sample-derived RNA forms a stable hybrid with the probe. In order to prevent false positive, it is preferred to carry out the hybridization and washing under highly stringent conditions. The conditions are determined by a large number of factors such as temperature, ionic strength, base composition, length of the probe and concentration of formamide. The factors are described, for example, in *Molecular Cloning*, Second Edition.

A labeled probe used in the Northern blotting can be prepared, for example, by incorporating a radioisotope, biotin, a fluorescence group, a chemiluminescence group or the like into a DNA having a nucleotide sequence complementary to the nucleotide sequence of the DNA of the present invention, a partial fragment of 100 nucleotides or more of the DNA, or an oligonucleotide designed from the sequence of the DNA, using a known method (nick translation, random priming or kinasing). Since the amount of the bound labeled probe reflects the expression level of the mRNA, the expression level of the mRNA can be determined by determining the amount of the bound labeled probe. Also, structural changes in the mRNA can be known by analyzing the labeled probe binding site.

The expression level of the mRNA can be detected by the in situ hybridization in which hybridization and washing are carried out using the above labeled probe and a sample isolated as a paraffin or cryostat section from a tissue obtained from a living body. In order to prevent false positive in the in situ hybridization method, it is preferred to carry out the hybridization and washing under highly stringent conditions. The conditions are determined by a large number of factors such as temperature, ionic strength, base composition, length of the probe and concentration of formamide. These factors are described, for example, in *Molecular Cloning*, Second Edition.

The mRNA can be detected according to a quantitative PCR, a differential hybridization method, a DNA micro-array/DNA tip or the like by using a sample-derived RNA or a cDNA synthesized from the RNA using a reverse transcriptase. Hereinafter, the cDNA is called sample-derived cDNA. A random primer or oligo(dT) primer can be used in the synthesis of cDNA.

In the quantitative PCR, a DNA fragment derived from mRNA encoding the polypeptide of the present invention is amplified by PCR using the sample-derived cDNA as the template and primers (comprising a pair of oligonucleotides of a DNA having a sequence identical to continues 5 to 120 nucleotides of the nucleotide sequence in the DNA of the present invention and a DNA having a sequence identical to continues 5 to 120 nucleotides of a nucleotide sequence complementary to the nucleotide sequence in the DNA of the present invention) designed based on the nucleotide sequence in the DNA of the present invention. Since the amount of the amplified DNA fragment reflects the expression level of the mRNA, it is possible to determine the amount of the mRNA by using a DNA encoding actin, glyceraldehyde-3-phosphate dehydrogenase (hereinafter referred to as "G3PDH") or the like as the internal control. Also, changes in the structure of the mRNA can be detected by separating the amplified DNA fragment by gel electrophoresis. In this detection method, it is preferred to use appropriate primers which amplify the target sequence specifically and efficiently. Such appropriate primers can be designed based on such conditions that, e.g., hybridization between the primers and intramolecular hybridization of a primer are not caused, that they specifically hybridize to the target cDNA at the annealing temperature and are removed from the target cDNA under denaturing conditions. It is necessary to quantify the amplified DNA fragment during the PCR when the amplified product is increasing by exponential function. Such PCRs can be detected by recovering the amplified DNA fragment produced by each reaction and quantitatively analyzing it by gel electrophoresis.

The principle of the real time PCR [Junko Stevens, *Experimental Medicine (Jikken Igaku)*, Supplement, 15, 46-51 (1997)] is identical to the above quantitative PCR, and the amount of amplified DNA fragment can be detected in real time as released fluorescence quantity by PCR using the TaqMan probe and a forward primer and a reverse primer labeled with two fluorescence dyes, respectively.

Changes in the expression level of mRNA encoding the polypeptide of the present invention can be detected by carrying out hybridization and washing on a filter or a basement such as a slide glass or silicon to which the DNA of the present invention is immobilized, using a sample-derived cDNA. Methods based on such a principle include so-called differential hybridization [*Trends in Genetics*, 1, 314-317 (1991)] and DNA micro array/DNA tip [*Genome Research*, 6, 639-645 (1996)]. In each method, difference in the expression level of the mRNA between a control sample and a target sample can be accurately detected by immobilizing an internal control such as actin or G3PDH on a filter or a basement. Also, the expression level of the mRNA can be accurately determined by synthesizing labeled cDNA molecules using respectively different labeled dNTP based on control sample- and target sample-derived RNAs, and simultaneously hybridizing two labeled cDNA probes on one filter or one basement.

In the RNase protection assay, a labeled antisense RNA is synthesized by firstly ligating a promoter sequence such as T7 promoter or SP6 promoter to the 3'-terminal of the DNA of the present invention, and then carrying out in vitro transcription using an RNA polymerase in the presence of labeled rNTP. The labeled antisense RNA is hybridized to a sample-derived RNA to form an RNA-RNA hybrid, and then the hybrid is digested with an RNase and the RNA fragment protected from the digestion is detected by forming a band by gel electrophoresis. The expression level of mRNA encoding the polypeptide of the present invention can be determined by quantifying the thus obtained band.

The detection method described in the above can be used in detecting or diagnosing diseases which accompany changes in the expression level of a gene encoding the polypeptide of the present invention. When such a detection or diagnosis is carried out, DNA, mRNA or total RNA obtained from a patient having inflammatory disease, cancer or tumor metastasis, a patient having diseases which accompanies changes in the expression level of a DNA encoding the polypeptide of the present invention or a healthy person is used as the sample. The DNA, mRNA or total RNA can be obtained from biological samples such as various tissues, sera and saliva of a patient or healthy person or from primary culture cells obtained by preparing cells from the biological samples and culturing them in an appropriate medium in test tubes. The range of the expression levels of the gene of the patients and healthy persons is determined by measuring and comparing the expression level of the gene encoding the polypeptide of the present invention in samples of two or more patients and healthy persons by the above detection methods. Detection or diagnosis of diseases which accompany changes in the expression of the gene can be carried out by comparing the expression level of the gene in a sample of a test person with the expression level in healthy persons.

Also, two types of Gal β1,3-N-acetylglucosaminyltransferases have already been cloned other than the polypeptide of the present invention, and it is necessary to use a detection method based on the nucleotide sequence of a gene (e.g., Northern hybridization or PCR) in order to detect expression of a specific Gal β1,3-N-acetylglucosaminyltransferase. Using the DNA of the present invention, its expression can be accurately examined by discriminating it from the already cloned two enzymes.

The determination of the expression level is specifically described below.

Since it is considered that differentiation of blood cells and mutual recognition and migration of nerve cells are controlled by the expression of lactosylceramide β1,3-N-acetylglucosaminyltransferase, there is a possibility that various diseases are induced by abnormal expression of this enzyme or decrease or increase in the activity of this enzyme by mutation, therefore the various diseases can be diagnosed by determining the expression level of the DNA encoding the polypeptide of the present invention.

For example, since treatments of myelogenous leukemia and lymphocytic leukemia are different, it is considered that it is clinically very useful if there is a method for accurately discriminating the two leukemia diseases. While lactosylceramide β1,3-N-acetylglucosaminyltransferase activity is detected in myeloid cell lines, the activity is not detected in lymphocyte cell lines, so that it is considered that the gene encoding the polypeptide of the present invention is expressed in myelogenous leukemia cells but the gene encoding the polypeptide of the present invention is not expressed in lymphocytic leukemia cells. Myelogenous leukemia and lymphocytic leukemia can be discriminated by determining the expression level of the gene encoding the polypeptide of the present invention by the Northern hybridization or PCR, by preparing mRNA, total RNA or cDNA from leukemia cells collected from a patient and using a DNA having a nucleotide sequence complementary to the nucleotide sequence in the DNA of the present invention, a partial fragment of 100 bp or more of the DNA, or an oligonucleotide designed from the nucleotide sequence in the DNA of the present invention.

(ii) Preparation and Identification of a Promoter Region and a Transcription Controlling Region of the DNA of the Present Invention It is possible to prepare and identify a promoter region and a transcription controlling region of the DNA by using the DNA of the present invention as a probe according to a known method [*New Cell Technology Experimentation Protocol (Shin Saibo Kogaku Jikken Protocol)*, edited by Antitumor Research Group, Institute of Medical Science, The University of Tokyo, published by Shujun-sha (1993)].

Screening of a genomic DNA library prepared using a chromosomal DNA isolated from mouse, rat, or human cells or tissues by a method such as plaque hybridization is carried out using the DNA or oligonucleotide (particularly a 5' side region of cDNA) of the present invention as the probe, so that a promoter region and a transcription controlling region of the mouse, rat, or human genomic DNA of the DNA of the present invention can be obtained. Also, the exon/intron structure of the DNA can be found by comparing nucleotide sequence of the thus obtained genomic DNA and nucleotide sequence of cDNA. Also, a promoter region and a transcription controlling region of the DNA can also be obtained from other non-human mammals using the same method.

Currently, sequences of a large number of human chromosomal genes whose functions are unknown are registered in data bases. Thus, a human chromosomal gene encoding the polypeptide of the present invention can be identified and its structure can be found by comparing the sequence of human cDNA encoding the polypeptide of the present invention with sequences of the human chromosomal genes registered in data bases. When a chromosomal gene sequence which corresponds to the sequence of cDNA is registered, a promoter region and exon and intron structure of a chromosomal gene encoding the polypeptide of the present invention can be determined by comparing the sequence of the cDNA with the sequence of the chromosomal gene.

The promoter regions include all promoter regions and transcription controlling regions involved in the transcription of genes encoding the polypeptide of the present invention in mammal cells. The transcription controlling regions include regions containing an enhancer sequence which enhances basal transcription of a gene encoding the polypeptide of the present invention, a silencer sequence that attenuates it and the like. Examples include a promoter region and a transcription controlling region functioning in cells selected from leukocytes, nerve cells, tracheal cells, lung cells, colon cells, placental cells, neuroblastoma cells, glioblastoma cells, colon cancer cells, lung cancer cells, pancreatic cancer cells, stomach cancer cells and leukemia cells. The thus obtained promoter region and transcription controlling region can be applied to a screening method described below and are also useful in analyzing the transcription controlling mechanism of the gene.

(iii) Detection of Mutation and Polymorphism of a DNA Encoding the Polypeptide of the Present Invention Since the novel β1,3-N-acetylglucosaminyltransferase of the present invention is also involved in the synthesis of a poly-N-acetyllactosamine sugar chain, it is considered that this enzyme is involved in the synthesis of a sialyl Le$^x$ sugar chain in leukocyte and a cancer-related sugar chains in cancer cells (sialyl Lewis x sugar chain, sialyl Lewis a sugar chain, sialyl Lewis c sugar chain and dimeric Lewis a sugar chain). Accordingly, it is considered that diagnosis of inflammatory disease, cancer or tumor metastasis, or prediction of prognosis of cancer is possible by examining mutation and polymorphism of the DNA of the present invention.

Also, it is able to use in diagnosis of other diseases such as functional abnormality of the gene based on polymorphism and mutation of the gene by examining relationship between polymorphism and mutation of the DNA of the present invention and diseases of organs in which the DNA is expressed.

The method for detecting mutation of the DNA of the present invention is described below.

The most distinct test for evaluating the presence or absence of a disease-causing mutation in the DNA of the present invention is to directly compare the DNA from a control group with the DNA from patients of the disease.

Specifically, human biological samples such as tissues, sera and saliva or primary culture cells established from the biological samples are collected from a patient of a disease whose cause is a mutation in the DNA encoding the polypeptide of the present invention and from a healthy person, and DNA is extracted from the biological samples or the primary culture cells (hereinafter, the DNA is called sample-derived DNA). Next, the DNA encoding the polypeptide of the present invention is amplified by PCR using the sample-derived DNA as the template and primers designed based on the nucleotide sequence in the DNA of the present invention. As another method, the DNA encoding the polypeptide of the present invention can be amplified by PCR using the above cDNA derived from the biological samples or the primary culture cells as the template. The presence or absence of a mutation can be examined by comparing the thus obtained the amplified DNA derived from a patient with the amplified DNA derived from a healthy person. The comparing method includes a method for directly examining nucleotide sequence of the amplified DNA samples, a method for detecting a heterogeneous formed by hybridizing a DNA having a wild type sequence with a DNA having a mutation (cf., the following description) and the like.

Furthermore, as a method for detecting the presence of a mutation in a DNA encoding the polypeptide of the present invention, which causes the above diseases, a method for detecting a heteroduplex formed by hybridizing a DNA strand having a wild type allele with a DNA strand having a mutation allele can be used.

Examples of the method for detecting heteroduplex include (a) detection of heteroduplex by polyacrylamide gel electrophoresis [*Trends Genet.*, 7, 5 (1991)], (b) single strand conformation polymorphism analysis [*Genomics*, 16, 325-332 (1993)], (c) chemical cleavage of mismatches (CCM) [*Human Molecular Genetics* (1996), Tom Strachan and Andrew P. Read (BIOS Scientific Publishers Limited)], (d) enzymatic cleavage of mismatches [*Nature Genetics*, 9, 103-104 (1996)], (e) denaturing gradient gel electrophoresis [*Mutat. Res.*, 288, 103-112 (1993)] and the like.

(a) Detection of Heteroduplex by Polyacrylamide Gel Electrophoresis

A DNA encoding the polypeptide of the present invention is amplified by PCR using a sample-derived DNA or a sample-derived cDNA as the template and primers designed based on the nucleotide sequence represented by SEQ ID NO:2. The primers are designed in such a manner that a DNA of 200 bp or less is amplified. The thus amplified DNA (a patient-derived DNA or a mixture of a patient-derived amplified DNA with a healthy person-derived amplified DNA) is converted into single-stranded DNA by thermal denaturation and then double-stranded DNA is again formed by gradually reducing temperature. The double-stranded DNA is subjected to polyacrylamide gel electrophoresis. When heteroduplexs are formed, they can be detected as extra bands due to slower mobility than homologous double strands having no mutation. The separation performance is efficient when a special gel (Hydro-link, MDE or the like) is used. In the screening of fragments smaller than 200 bp, insertion, deletion and almost all of one nucleotide substitution can be detected. It is preferred to carry out the heteroduplex analysis using a single gel in combination with the single strand conformation polymorphism analysis described below.

(b) Single Strand Conformation Polymorphism Analysis (SSCP Analysis)

An amplified DNA prepared by the method described in (a) is denatured and then subjected to electrophoresis using an undenatured polyacrylamide gel. The amplified DNA can be detected as a band by labeling the primers with an isotope or fluorescence dye in the DNA amplification or by silver-staining the unlabeled amplification product. When a control sample is simultaneously subjected to the electrophoresis in order to clarify difference from the pattern of wild type, a fragment having a mutation can be detected from the difference in mobility.

(c) Chemical Cleavage of Mismatches (CCM)

A DNA encoding the polypeptide of the present invention is amplified by PCR using a sample-derived DNA or a sample-derived cDNA as the template and primers designed based on the nucleotide sequence represented by SEQ ID NO:2. Next, a labeled DNA prepared by incorporating a radioisotope or fluorescence dye into the DNA of the present invention is hybridized with the amplified DNA and treated with osmium tetroxide to cleave one of the chains of DNA where a mismatch is occurred, and thus a mutation can be detected. The CCM is one of the methods having the highest sensitivity and can also be applied to samples of a kilo base length.

(d) Enzymatic Cleavage of Mismatches

Mismatches can also be enzymaticcally cleaved by using a combination of enzyme involved in the intracellular repairing of mismatches such as T4 phage resolvase or endonuclease VII with RNase A, instead of the osmium tetroxide of the above (c).

(e) Denaturing Gradient Gel Electrophoresis (DGGE)

An amplified DNA prepared by the method described in (c) is subjected to electrophoresis using a density gradient of a chemical modifier or a gel having temperature gradient. The amplified DNA fragment migrates in the gel to a position where it denatures into single strand, and stops the migration after the denaturation. Since mobility of the amplified DNA in the gel differs in the presence and absence of a mutation in the DNA, it is possible to detect the presence of mutation. In order to increase the detection sensitivity, a poly(G:C) terminal may be added to respective primers.

As another method for detecting a mutation in the DNA, a protein truncation test (PTT) [*Genomics*, 20, 1-4 (1994)] is exemplified. Frameshift mutation, splice site mutation and nonsense mutation which cause deficiency of polypeptides can be specifically detected by the test. Specifically, a DNA encoding the full-length polypeptide of the present invention is amplified by PCR using a sample-derived cDNA (a sample-derived DNA can also be used when intron is not present in a chromosomal gene) as the template and primers designed based on the nucleotide sequence represented by SEQ ID NO:2. In that case, a T7 promoter sequence and a eucaryote translation initiation sequence are added at the 5-end of a primer corresponding to the N-terminal side of the polypeptide. A polypeptide can be produced by carrying out in vitro transcription and translation using the amplified DNA. The presence or absence of a mutation which causes deficiency of polypeptide can be detected from the migrated position when the polypeptide is subjected to a gel electrophoresis. A mutation which causes a deficiency is not present when the migrated position of the polypeptide is present at a position corresponding to the full-length polypeptide. On the other hand, when there is a deficiency in the polypeptide, the polypeptide migrates to a position smaller than the full-length polypeptide so that position of the mutation can be presumed by the position.

A disease induced by a mutation in regions other than the coding region of the chromosomal gene encoding the polypeptide of the present invention can also be present. Since abnormality in the size and expression level of mRNA is detected in patients of diseases caused by mutation in the non-coding regions, their abnormality can be examined by Northern hybridization and PCR.

When the presence of a mutation in a non-coding region is suggested, the presence or absence of a mutation in the promoter region, transcription controlling region or intron region of the gene is inspected. These gene regions can be cloned using a DNA having the nucleotide sequence represented by SEQ ID NO:2 as the probe for hybridization. Moreover, sequence information on these gene regions can also be obtained in some cases by comparing them with human chromosomal gene sequences registered in various data bases. As shown in Example 12, intron has not been present in the case of the chromosomal gene encoding the polypeptide of the present invention. Mutations in the non-coding regions can be screened according to any one of the above methods.

Polymorphism analysis of the DNA of the present invention can be carried out by using the gene sequence information of the DNA. Specifically, gene polymorphism can be analyzed using Southern blotting, direct sequencing, PCR, DNA tip and the like [*Clinical Inspection* (*Rinsho Kensa*), 42, 1507-1517 (1998), *Clinical Inspection* (*Rinsho Kensa*), 42, 1565-1570 (1998)].

The thus found mutation and polymorphism can be identified as SNPs (single nucleotide polymorphism) having linkage to diseases, by a statistic treatment according to the method described in *Handbook of Human Genetics Linkage*, The John Hopkins University Press, Baltimore (1994). Also, a disease can be diagnosed by obtaining DNA samples from a family having a clinical history of the above disease, according to the above method, and detecting a mutation.

(iv) Inhibition of Transcription and Translation of DNA Encoding the Polypeptide of the Present Invention The DNA of the present invention can inhibit transcription or translation of a DNA encoding the protein of the present invention by using antisense RNA/DNA techniques [*Bioscience and Industry*, 50, 322 (1992), *Chemistry*, 46, 681 (1991), *Biotechnology*, 9, 358 (1992), *Trends in Biotechnology*, 10, 87 (1992), *Trends in Biotechnology*, 10, 152 (1992), *Cell Technology*, 16, 1463 (1997)], triple helix techniques [*Trends in Biotechnology*, 10, 132 (1992)] and the like. For example, production of the polypeptide of the present invention can be inhibited by administering the DNA or oligonucleotide of the present invention. That is, each of transcription of a DNA encoding the polypeptide of the present invention or translation of a mRNA encoding the polypeptide of the present invention can be inhibited by using the DNA or oligonucleotide of the present invention or derivatives thereof. The inhibition method can be used as medicaments for treating or preventing diseases which accompany changes in the expression of a DNA encoding the polypeptide of the present invention such as inflammatory disease, cancer and tumor metastasis.

It is considered that the polypeptide of the present invention is involved in the synthesis of neolacto-series glycolipids and lacto-series glycolipids. Thus, it is considered that cancer can be treated by inhibiting transcription of the DNA of the present invention and translation of a mRNA encoding the polypeptide.

Also, when mechanisms of the above inflammatory reactions and metastases are taken into consideration, it can be expected to inhibit inflammatory reactions and prevent metastases by inhibiting expression of a poly-N-acetyllactosamine sugar chain on leukocytes and cancer cells. There is a possibility that expression of a poly-N-acetyllactosamine sugar chain in leukocytes and cancer cells can be inhibited by inhibiting transcription of the DNA of the present invention and translation of a mRNA encoding the polypeptide.

Furthermore, it is considered that Gal β1,3-N-acetylglucosaminyltransferases involved in the synthesis of a poly-N-acetyllactosamine sugar chain in specific leukocytes and cancer cells are different. Since there is a possibility that a lactosylceramide β1,3-N-acetylglucosaminyltransferase is involved in the synthesis of a poly-N-acetyllactosamine sugar chain in specific leukocytes and cancer cells, it is considered that synthesis of a poly-N-acetyllactosamine sugar chain on specific leukocytes and cancer cells expressing the polypeptide can be specifically inhibited by inhibiting transcription of the DNA of the present invention and translation of a mRNA encoding the polypeptide.

(v) Medicament Comprising the DNA or Oligonucleotide of the Present Invention

A medicament comprising the DNA of the present invention, a partial fragment of the DNA or the oligonucleotide of the present invention can be prepared and administered according to the method for a medicament comprising the polypeptide of the present invention described in (3).

(6) Production of Antibody which Recognizes the Polypeptide of the Present Invention (i) Production of Polyclonal Antibody A polyclonal antibody can be produced by using the purified sample of the full-length or a partial fragment of the polypeptide obtained by the method of the above (3) or a peptide having an amino acid of a part of the polypeptide of the present invention as the antigen and administering it to an animal.

Rabbits, goats, rats, mice, hamsters and the like can be used as the animal to be administered. It is preferred that the dose of the antigen is 50 to 100 µg per one animal. When a peptide is used, it is preferred to use the peptide as the antigen after conjugating it to a carrier protein such as keyhole limpet haemocyanin or bovine thyroglobulin by a covalent bond. The peptide used as the antigen can be synthesized using a peptide synthesizer.

The antigen is administered 3 to 10 times at one-to two-week intervals after the first administration. Three to seven days after each administration, a blood sample is collected from the venous plexus of the fundus of the eye, and the serum is tested by enzyme immunoassay [*Enzyme-linked Immunosorbent Assay (Koso Meneki Sokuteiho)* (ELISA), published by Igaku Shoin, (1976), *Antibodies—A Laboratory Manual*, Cold Spring Harbor Laboratory (1988)] and the like as to whether it is reactive with the antigen used for immunization.

A polyclonal antibody can be obtained by collecting a serum sample from non-human mammal in which the serum showed a sufficient antibody titer against the antigen used for immunization, and separating and purifying the serum.

Examples of the method for its separation and purification include centrifugation, salting out with 40 to 50% saturated ammonium sulfate, caprylic acid precipitation [*Antibodies—A Laboratory Manual*, Cold Spring Harbor Laboratory (1988)] and chromatography using a DEAE-Sepharose column, an anion exchange column, a protein A- or G-column, a gel filtration column or the like, which may be used alone or in combination.

(ii) Production of Monoclonal Antibody (a) Preparation of Antibody Producing Cells A rat whose serum showed a sufficient antibody titer against the partial fragment polypeptide of the polypeptide of the present invention used in the immunization is used as the supply source of antibody producing cells.

Three to seven days after the final administration of the antigen substance to the rat which showed the sufficient antibody titer, the spleen is excised. The spleen is cut to pieces in MEM (manufactured by Nissui Pharmaceutical), and cells are loosened using a pair of forceps and centrifuged at 1,200 rpm for 5 minutes and then the supernatant is discarded. Splenocytes in the thus obtained precipitation fraction are treated with a Tris-ammonium chloride buffer (pH 7.65) for 1 to 2 minutes for eliminating erythrocytes and then washed three times with MEM, and the thus obtained splenocytes are used as the antibody producing cells.

(b) Preparation of Myeloma Cells

As myeloma cells, established cell lines obtained from mouse or rat are used.

Examples include 8-azaguanine-resistant mouse (BALB/c-derived) myeloma cell lines P3-X63Ag8-U1 (hereinafter referred to as "P3-U1") [*Curr. Topics Microbiol. Immunol.*, 81, 1 (1978), *Eur. J. Immunol.*, 6, 511 (1976)], SP2/O—Ag14 (SP-2) [*Nature*, 276, 269 (1978)], P3-X63-Ag8653 (653) [*J. Immunol.*, 123, 1548 (1979)], P3-X63-Ag8 (X63) [*Nature*, 256, 495 (1975)] and the like.

The cell lines are subcultured in an 8-azaguanine medium [prepared by supplementing RPMI-1640 medium with glutamine (1.5 mmol/l), 2-mercaptoethanol ($5 \times 10^{-5}$ mol/l), gentamicin (10 µg/ml) and fetal calf serum (FCS) (manufactured by CSL, 10%) and further supplementing the resulting medium (hereinafter referred to as "normal medium") with 8-azaguanine (15 µg/ml)], and they are cultured in the normal medium 3 to 4 days before the cell fusion, and $2 \times 10^7$ or more of the cells are used for the cell fusion.

(c) Preparation of Hybridoma

The antibody producing cells obtained in (a) and the myeloma cells obtained in (b) are washed thoroughly with MEM or PBS (1.83 g of disodium hydrogenphosphate, 0.21 g of potassium dihydrogenphosphate and 7.65 g of sodium chloride, 1 liter of distilled water, pH 7.2) and mixed in a proportion of antibody producing cells:myeloma cells=5 to 10:1, and the mixture is centrifuged at 1,200 rpm for 5 minutes and then the supernatant is discarded.

Cells in the thus obtained precipitation fraction are thoroughly loosened, a mixture of 2 g of polyethylene glycol-1000 (PEG-1000), 2 ml of MEM and 0.7 ml of dimethyl sulfoxide (DMSO) is added to the cells in an amount of 0.2 to 1 ml per 108 antibody producing cells under stirring at 37° C., and then 1 to 2 ml of MEM is added several times at 1 to 2 minute intervals. After the addition, the whole volume is adjusted to 50 ml by adding MEM.

After the thus prepared solution is centrifuged at 900 rpm for 5 minutes, the supernatant is discarded. Cells in the thus obtained precipitation fraction are gently loosened and then suspended in 100 ml of HAT medium [prepared by supplementing the normal medium with hypoxanthine ($10^{-4}$ mol/l), thymidine ($1.5 \times 10^{-5}$ mol/l) and aminopterin ($4 \times 10^{-7}$ mol/l)] by repeated drawing up into and discharging from a measuring pipette.

The suspension is dispensed in 100 µl/well portions into a 96-well culture plate and cultured at 37° C. for 7 to 14 days in a 5% $CO_2$ incubator. After culturing, a portion of the culture supernatant is taken out and subjected to an enzyme immunoassay described in [*Antibodies, A Laboratory Manual*, Cold Spring Harbor Laboratory, Chapter 14 (1988)] or the like, and hybridomas which specifically react with the partial fragment polypeptide of the polypeptide of the present invention are selected.

As an example of the enzyme immunoassay, the following method is shown.

The partial fragment polypeptide of the polypeptide of the present invention used as the antigen in the immunization is coated on an appropriate plate, allowed to react with a first antibody, namely a hybridoma culture supernatant or the purified antibody obtained in the following (d), further allowed to react with a second antibody, namely an anti-rat or anti-mouse immunoglobulin antibody labeled with biotin, an enzyme, a chemiluminescence substance, a radioactive compound or the like and then subjected to the reaction corresponding to the used labeled substance, and those which react specifically with the polypeptide of the present invention are selected as hybridomas that produce the monoclonal antibody for the polypeptide of the present invention.

Cloning is repeated twice using the hybridomas according to a limiting dilution method [HT medium (a medium prepared by eliminating aminopterin from HAT medium) for the first and the normal medium for the second], and those in which high antibody titer is constantly observed are selected as hybridomas that produce an anti-polypeptide antibody against the polypeptide of the present invention.

(d) Preparation of Monoclonal Antibody

The hybridoma cells capable of producing a monoclonal antibody against the polypeptide of the present invention obtained in (c) are injected into the abdominal cavity of 8 to 10-week-old mice or nude mice treated with pristane [by intraperitoneal administration of 0.5 ml of 2,6,10,14-tetramethylpentadecane (pristane), followed by feeding for 2 weeks] at a dose of 5 to 20×10$^6$ cells per animal. The hybridoma causes ascites tumor in 10 to 21 days. The ascitic fluid is collected from the ascites tumor-caused mice and centrifuged at 3,000 rpm for 5 minutes to remove the solid matter. The monoclonal antibody can be obtained by purifying it from the thus obtained supernatant by the same method used in the purification of a polyclonal antibody.

The subclass of the antibody is determined using a mouse monoclonal antibody typing kit or a rat monoclonal antibody typing kit. The amount of the protein is calculated by the Lowry method or from the absorbance at 280 nm.

(e) Neutralizing Antibody

A neutralizing antibody having a property to inhibit activity of the polypeptide of the present invention by binding to the polypeptide of the present invention is included in the antibody of the present invention. In measuring the activity of the polypeptide of the present invention by the method described in (3) by adding the antibody obtained in the above, when the activity of the polypeptide of the present invention is reduced in comparison with a case of not adding the antibody, it can be confirmed that the antibody is a neutralizing antibody.

(7) Application of the Antibody of the Present Invention (i) Detection and Quantification of the Polypeptide of the Present Invention The polypeptide of the present invention or a cell or tissue containing the polypeptide can be immunologically detected by an antigen-antibody reaction using an antibody which specifically recognizes the polypeptide of the present invention. The detection method can be used in the diagnosis of diseases which accompany changes in the expression of the polypeptide of the present invention such as inflammatory disease, cancer and tumor metastasis. The detection method can also be used in the quantification of a protein.

Examples of the immunological detection and quantification methods include fluorescent antibody technique, enzyme-linked immunosorbent assay (ELISA), radioimmunoassay (RIA), immunohistochemistry such as immunohistostaining and immunocytostaining (ABC method, CSA method, etc.), Western blotting, dot blotting, immunoprecipitation, sandwich ELISA [*Monoclonal Antibody Experimentation Manual (Tan Clone Kotai Jikken Manual)*, Kodansha Scientific (1987), *Second Biochemical Experimentation Series* (Zoku Seikagaku Jikken Koza), Vol. 5, "Method for Immuno-biochemical Research (Men-eki Seikagaku Kenkyu-ho)" Tokyo Kagaku Dojin (1986)] and the like.

Fluorescent antibody technique is a method in which the antibody of the present invention is allowed to react with a microorganism, an animal cell or insect cell or a tissue, which expressed the polypeptide of the present invention inside or outside of the cell, and further allowed to react with an anti-mouse IgG antibody or a fragment thereof labeled with a fluorescence substance such as fluorescein isothiocyanate (FITC), and then the fluorescence dye is measured using a flow cytometer.

Enzyme-linked immunosorbent assay (ELISA) is a method in which the antibody of the present invention is allowed to react with a microorganism, an animal cell or insect cell or a tissue, which expressed the polypeptide inside or outside the cell, and further allowed to react with an anti-mouse IgG antibody or a binding fragment thereof labeled with an enzyme such as peroxidase or biotin, and then the chromogenic dye is measured using an absorptiometer.

Radioimmunoassay (RIA) is a method in which the antibody of the present invention is allowed to react with a microorganism, an animal cell or insect cell or a tissue, which expressed the polypeptide inside or outside the cell, and further allowed to react with an anti-mouse IgG antibody or a fragment thereof labeled with a radioisotope, and then the isotope is measured using a scintillation counter or the like.

Immunocytostaining or immunohistostaining is a method in which an antibody capable of specifically recognizing the polypeptide is allowed to react with a microorganism, an animal cell or insect cell or a tissue, which expressed the polypeptide inside or outside the cell, and further allowed to react with an anti-mouse IgG antibody or a fragment thereof labeled with a fluorescence substance such as FITC or an enzyme such as peroxidase or biotin, and then the cell is observed under a microscope.

Western blotting is a method in which a lysate of a microorganism, an animal cell or insect cell or a tissue, which expressed the polypeptide inside or outside of the cell, is separated by SDS-polyacrylamide gel electrophoresis [*Antibodies—A Laboratory Manual*, Cold Spring Harbor Laboratory (1988)], and the gel is blotted on a PVDF membrane or nitrocellulose membrane, allowed to react with an antibody capable of specifically recognizing the polypeptide on the membrane and further allowed to react with an anti-mouse IgG antibody or a fragment thereof labeled with a fluorescence substance such as FITC or an enzyme such as peroxidase or biotin, and then a reaction corresponding to the labeled substance is carried out.

The dot blotting is a method in which a lysate of a microorganism, an animal cell or insect cell or a tissue, which expressed the polypeptide inside or outside the cell, is blotted on a nitrocellulose membrane, allowed to react with the antibody of the present invention on the membrane and further allowed to react with an anti-mouse IgG antibody or a binding fragment thereof labeled with fluorescence substance such as FITC or an enzyme such as peroxidase or biotin, and then a reaction corresponding to the labeled substance is carried out.

The immunoprecipitation is a method in which a lysate of a microorganism, an animal cell or insect cell or a tissue, which expressed the polypeptide inside or outside the cell, is allowed to react with an antibody capable of specifically recognizing the polypeptide, and then an antigen-antibody complex is precipitated by adding a carrier such as protein G-Sepharose having the ability to specifically bind to immunoglobulin.

The sandwich ELISA is a method in which a lysate of a microorganism, an animal cell or insect cell or a tissue, which expressed the polypeptide of the present invention inside or outside the cell, is allowed to react with a plate to which an antibody capable of specifically recognizing the polypeptide is adsorbed, and further allowed to react with an antibody (having an antigen recognizing site different from the above antibody) labeled with a fluorescence substance such as FITC or an enzyme such as peroxidase or biotin, which specifically recognizes the polypeptide of the present invention, and then a reaction corresponding to the labeled substance is carried out.

Also, two types of Gal β1,3-N-acetylglucosaminyltransferases have already been cloned in addition to the polypeptide of the present invention, and it is necessary to carry out an immunological detection using a specific antibody for detecting expression of a specified Gal β1,3-N-acetylglucosaminyltransferase. Accordingly, the antibody of the present invention makes it possible to examine the expression of the polypeptide of the present invention accurately.

(ii) Application to Diagnosis and Treatment of Inflammatory Diseases and Cancers Identification of changes in the expression level of the polypeptide in human biological samples and human derived primary culture cells, and structural changes of the expressed polypeptide is useful for checking the danger of causing future onset of diseases and the cause of diseases already developed.

It is suggested that the polypeptide of the present invention involved in the synthesis of neolacto-series glycolipids and lacto-series glycolipids and the synthesis of a poly-N-acetyllactosamine sugar chain in leukocytes and cancer cells. Accordingly, diagnosis, prevention and treatment of inflammatory diseases and malignancy of cancers become possible by examining the expression level of the polypeptide of the present invention in leukocytes and cancer cells, and by controlling activity of the polypeptide of the present invention using the neutralizing antibody of the present invention.

Also, since it is considered that differentiation of blood cells and mutual recognition and migration of nerve cells are controlled by the expression of lactosylceramide β1,3-N-acetylglucosaminyltransferase, there is a possibility that various diseases are induced by abnormal expression of this enzyme, and decrease and increase of activity of this enzyme by mutation. Thus, diseases relating to differentiation of blood cells or mutual recognition and migration of nerve cells can be diagnosed, prevented and treated by examining the expression level of the polypeptide of the present invention in blood cells or nerve cells, or by controlling activity of the polypeptide of the present invention using the neutralizing antibody of the present invention.

For example, since treatments of myelogenous leukemia and lymphocytic leukemia are different, it is considered that it is clinically very useful if there is a method for accurately discriminating these two leukemia diseases. While a lactosylceramide β1,3-N-acetylglucosaminyltransferase activity is detected in myeloid cell lines, the activity is not detected in lymphocyte cell lines, so that it is considered that the gene encoding the polypeptide of the present invention is expressed in myelogenous leukemia cells but the gene encoding the polypeptide of the present invention is not expressed in lymphocytic leukemia cells. It is possible to discriminate myelogenous leukemia and lymphocytic leukemia by detecting, using the antibody of the present invention, expression of this enzyme protein in leukemia cells collected from patients.

In addition, it is considered that Gal β1,3-N-acetylglucosaminyltransferases involved in the synthesis of a poly-N-acetyllactosamine sugar chain in specific leukocytes and cancer cells are different. There is a possibility that lactosylceramide β1,3-N-acetylglucosaminyltransferase is involved in the synthesis of a poly-N-acetyllactosamine sugar chain in specific leukocytes and cancer cells, therefore, by inhibiting a lactosylceramide β1,3-N-acetylglucosaminyltransferase activity of the polypeptide of the present invention using a neutralizing antibody, synthesis of a poly-N-acetyllactosamine sugar chain on specific leukocytes and cancer cells expressing the polypeptide can be specifically inhibited.

Examples of the diagnosing methods by detecting expression level and structural changes of the polypeptide include the above fluorescent antibody technique, enzyme-linked immunosorbent assay (ELISA), radioimmunoassay (RIA), immunohistochemistry such as immunohistostaining and immunocytostaining (ABC method, CSA method, etc.), Western blotting, dot blotting, immunoprecipitation, sandwich ELISA and the like.

The samples diagnosed by the above methods include biological samples, such as tissues, blood, sera, urine, feces and saliva, collected from patients of diseases which are known to accompany changes in the expression of the polypeptide of the present invention such as inflammatory disease, cancer or tumor metastasis, as such, or cells and cell extracts prepared from the biological samples are used. Furthermore, samples isolated as paraffin or cryostat sections from tissues obtained from biological samples can also be used.

The method for detecting immunologically includes ELISA and fluorescent antibody technique which use a microtiter plate, Western blot technique, immunohistostaining and the like.

Examples of the method for quantifying immunologically include a sandwich ELISA involving use of two monoclonal antibodies against different epitopes among the antibodies capable of reacting with the polypeptide of the present invention in a liquid phase and a radioimmunoassay involving use of the polypeptide of the present invention labeled with a radioisotope such as $^{125}$I and an antibody which recognizes the polypeptide of the present invention.

Medicaments comprising the antibody of the present invention can be prepared and administered according to the methods for medicaments comprising the polypeptide of the present invention described in (3).

(8) Method for Preparing Recombinant Virus Vector which Produces the Polypeptide of the Present Invention A method for preparing a recombinant virus vector for the production of the polypeptide of the present invention in specific human tissues is described below.

A DNA fragment having an appropriate length containing a region moiety encoding the polypeptide is prepared based on a full-length cDNA of the DNA of the present invention, if necessary. Examples include a DNA comprising the nucleotide sequence represented by SEQ ID NO:2, a DNA comprising a nucleotide sequence of positions 135 to 1,268 in the nucleotide sequence represented by SEQ ID NO:2, a DNA comprising a nucleotide sequence of positions 249 to 1,268 in the nucleotide sequence represented by SEQ ID NO:2 and the like.

A recombinant virus vector is constructed by inserting the full-length cDNA or a fragment of the DNA into the downstream of the promoter in a vies vector.

In the case of an RNA virus vector, a recombinant virus vector is constructed by preparing a cRNA homologous to the full-length cDNA of the gene of the present invention or an RNA fragment homologous to an appropriate length DNA fragment containing a region encoding the polypeptide, and inserting it into the downstream of the promoter in a virus vector. As the RNA fragment, a single-stranded chain of either one of a sense chain or an antisense chain is selected in response to the type of virus vector, in addition to a double-stranded chain. For example, an RNA homologous to the sense chain is selected in the case of a retrovirus vector, while an RNA homologous to the antisense chain is selected in the case of a Sendai virus vector.

The recombinant virus vector is introduced into a packaging cell suited for the vector.

All cells which can supply a protein encoded by a gene necessary for the packaging of a virus deficient in the corresponding recombinant virus vector can be used as the packaging cell, and, e.g., human kidney-derived HEK293 cell, mouse fibroblast-derived NIH3 T3 or the like which expressed the following proteins can be used.

Examples of the protein supplied by the packaging cell include proteins such as mouse retrovirus-derived gag, pol and env in the case of a retrovirus vector; proteins such as HIV virus-derived gag, pol, env, vpr, vpu, vif, tat, rev and nef in the case of a lentivirus vector; proteins such as adenovirus-derived E1A and E1B in the case of an adenovirus vector; proteins such as Rep (p5, p19, p40) and Vp (Cap) in the case of adeno-associated virus; and proteins such as NP, P/C, L, M, F and HN in the case of Sendai virus.

The virus vector includes those which can produce a recombinant virus in the above packaging cell and contain a promoter at such a position that the DNA of the present invention can be transcribed in a target cell. The plasmid vector includes MFG [*Proc. Natl. Acad. Sci. USA*, 92, 6733-6737 (1995)], pBabePuro [*Nucleic Acids Res.*, 18, 3587-3596 (1990)], LL-CG, CL-CG, CS-CG and CLG [*Journal of Virology*, 72, 8150-8157 (1998)], pAdex1 [*Nucleic Acids Res.*, 23, 3816-3821 (1995)] and the like.

As the promoter, any promoter can be used, so long as it can work for expression in human tissues. Examples include IE (immediate early) gene promoter of cytomegalovirus (human CMV), SV40 early promoter, retrovirus promoter, metallothionein promote, heat shock protein promoter, SRα promoter and the like. Furthermore, an enhancer of the IE gene of human CMV may be used together with the promoter.

The method for introducing a recombinant virus vector into a packaging cell includes a calcium phosphate method (Japanese Published Unexamined Patent Application No. 227075/90), a lipofection method [*Proc. Natl. Acad. Sci. USA*, 84, 7413 (1987)] and the like.

The virus vector which comprises the DNA of the present invention or an RNA comprising a sequence homologous to the DNA can be used as a medicament for treating or preventing diseases which accompany changes in the expression of the polypeptide of the present invention or a DNA encoding the polypeptide such as inflammatory disease, cancer or metastases, as a gene therapy agent described later.

(9) Application to Screening Methods

The polypeptide of the present invention has a β1,3-N-acetylglucosaminyltransferase activity, namely, an activity to transfer N-acetylglucosamine via β1,3-linkage to a galactose residue present in the non-reducing terminal of a sugar chain. Specifically, it has an activity to transfer N-acetylglucosamine via β1,3-linkage to a galactose residue present in the non-reducing terminal of a sugar chain of an acceptor selected from i) galactose, N-acetyllactosamine (Galβ1-4GlcNAc), Galβ1-3GlcNAc or lactose (Galβ1-4Glc), ii) an oligosaccharide having galactose, N-acetyllactosamine, Galβ1-3GlcNAc or lactose structure in the non-reducing terminal, and iii) a complex carbohydrate having galactose, N-acetyllactosamine, Galβ1-3GlcNAc or lactose structure in the non-reducing terminal, including lactosylceramide and paragloboside. Thus, a compound which changes this activity can be screened by contacting the polypeptide of the present invention with a sample to be tested.

Also, since the polypeptide of the present invention is involved in the synthesis of neolacto-series glycolipids and lacto-series glycolipids or the synthesis of a poly-N-acetyllactosamine sugar chain in various cells, it is possible to increase or decrease the synthesized amount of a neolacto-series glycolipid, a lacto-series glycolipid or poly-N-acetyllactosamine sugar chain in cells by use of a compound capable of enhancing or inhibiting the β1,3-N-acetylglucosaminyltransferase activity of the polypeptide.

Furthermore, a compound which accelerates or inhibits the transcription step of a gene encoding the polypeptide or the translation step of the transcripts into protein can control a synthesized amount of a neolacto-series glycolipid, a lacto-series glycolipid or poly-N-acetyllactosamine sugar chain in cells by controlling expression of the polypeptide.

Since it is known that a sialyl Lewis x sugar chain and a sialyl Lewis a sugar chain existing on the poly-N-acetyllactosamine sugar chain are ligands of selecting, it is considered that a compound capable of decreasing the synthesized amount of a poly-N-acetyllactosamine sugar chain is useful for anti-inflammation and tumor metastasis inhibition. On the other hand, a compound which increases the synthesized amount of a poly-N-acetyllactosamine sugar chain is considered to be useful in the synthesis of a poly-N-acetyllactosamine sugar chain and production of a complex carbohydrate to which a poly-N-acetyllactosamine sugar chain is added.

The compounds can be obtained by the following methods (i) to (vi).

(i) A compound having an activity to increase or decrease a β1,3-N-acetylglucosaminyltransferase activity is selected and obtained by measuring the β1,3-N-acetylglucosaminyltransferase activity using the method described in (3), in the presence of a compound to be tested and using the polypeptide of the present invention prepared using the method described in the above (3) (a purified product or a cell extract or culture supernatant of a transformant expressing the polypeptide) as an enzyme.

(ii) A compound having an activity to increase or decrease the amount of a poly-N-acetyllactosamine sugar chain is selected and obtained by culturing a cell capable of expressing the polypeptide of the present invention or the transformant described in the above (2) using the culturing method described in the above (2) for 2 hours to 1 week in the presence of a compound to be tested, and then measuring the amount of paragloboside or a poly-N-acetyllactosamine sugar chain on the cell surface by use of an antibody capable of recognizing paragloboside or an antibody capable of recognizing poly-N-acetyllactosamine sugar chain (anti-i antibody or anti-I antibody) or a lectin (LEA, PWM or DEA).

Examples of the measuring methods involving use of the above antibody or lectin include detection methods involving use of microtiter-aided ELISA, fluorescent antibody technique, Western blot technique, immunohistostaining and the like. The measurement can be also carried out by use of FACS.

(iii) A compound having an activity to increase or decrease a β1,3-N-acetylglucosaminyltransferase activity or an activity to increase or decrease the amount of paragloboside or a poly-N-acetyllactosamine sugar chain is selected and obtained by synthesizing a large number of peptides constituting parts of the polypeptide in a high density on plastic pins or a certain solid support, efficiently screening compounds which selectively bind to the peptides (WO 84/03564), and then carrying out by the above method (i) or (ii).

(iv) A compound having an activity to increase or decrease the amount of the polypeptide of the present invention is selected and obtained by culturing a cell capable of expressing the polypeptide by the culturing method described in the above (2) for 2 hours to 1 week in the presence of a compound to be tested, and then measuring the amount of the polypeptide in the cell by use of the antibody of the present invention described in the above (6).

Increased or decreased expression of the polypeptide can be detected by the fluorescent antibody technique, enzyme-linked immunosorbent assay (ELISA), radioimmunoassay (RIA), immunohistochemistry such as immunohistostaining method and immunocytostaining (ABC method, CSA method, etc.), Western blotting, dot blotting, immunoprecipitation or sandwich ELISA described in the above (7).

(v) A compound having an activity to increase or decrease the amount of transcripts of a DNA encoding the polypeptide of the present invention is selected and obtained by culturing a cell capable of expressing the polypeptide by the culturing method described in the above (2) for 2 hours to 1 week in the presence of a compound to be tested, and then measuring the amount of the transcripts in the cell by the methods described in the above (4) such as Northern hybridization, PCR or RNase protection assay.

(vi) A plasmid which carries a DNA obtained by ligating a reporter gene to the downstream of a promoter described in the above (2) is prepared by a known method and introduced into an animal cell described in the above (2) according to the method described in the above (2), thereby obtaining a transformant. Thereafter, by culturing the transformant by the culturing method described in the above (2) for 2 hours to 1 week in the presence of a compound to be tested, and then measuring expression level of the reporter gene in the cell using known methods [*New Cell Technology Experimentation Protocol* (*Shin Saibo Kogaku Jikken Protocol*), edited by Antitumor Research Group, Institute of Medical Science, The University of Tokyo, published by Shujun-sha (1993), *Biotechniques*, 20, 914 (1996), *J. Antibiotics*, 49, 453 (1996), *Trends in Biochemical Sciences*, 20, 448 (1995), *Cell Technology*, 16, 581 (1997)], a compound having an activity to increase or decrease the expression level is selected and obtained.

Examples of the reporter genes include a chloramphenicol acetyltransferase (CAT) gene, a β-galactosidase gene, a β-lactamase gene, a luciferase gene, a green fluorescent protein gene and the like.

It is considered that the polypeptide of the present invention is involved in the synthesis of neolacto-series glycolipids and lacto-series glycolipids in cancer cells. Thus, it is considered that cancer can be treated by inhibiting synthesis of neolacto-series glycolipids and lacto-series glycolipids in cancer cells by use of a compound which inhibits expression of the polypeptide or DNA of the present invention and is obtained by the above screening.

Also, when mechanisms of the above inflammatory reactions and metastases are taken into consideration, it can be expected to inhibit an inflammatory reaction and prevent tumor metastasis by inhibiting expression of a poly-N-acetyllactosamine sugar chain on leukocytes and cancer cells. It is considered that inhibition of inflammatory reactions and prevention of metastases become possible by inhibiting expression of a poly-N-acetyllactosamine sugar chain on leukocytes and cancer cells using a compound which inhibits expression of the polypeptide or DNA of the present invention and is obtained by the above screening.

It is considered that Gal β1,3-N-acetylglucosaminyltransferases involved in the synthesis of a poly-N-acetyllactosamine sugar chain in specific leukocytes and cancer cells are different. Since there is a possibility that lactosylceramide β1,3-N-acetylglucosaminyltransferase is involved in the synthesis of a poly-N-acetyllactosamine sugar chain in specific leukocytes and cancer cells, it can be expected that by a compound which inhibits expression of the DNA or polypeptide of the present invention, the synthesis of a poly-N-acetyllactosamine sugar chain in specific leukocytes and cancer cells expressing the polypeptide can be specifically inhibited.

(10) Preparation of Non-human Knockout Animal

Using a vector containing the DNA of the present invention, a mutant clone in which a DNA encoding the polypeptide of the present invention on the chromosome in embryonic stem cells of an objective animal such as cow, sheep, goat, pig, horse, domestic fowl or mouse is inactivated or substituted by any sequence by known homologous recombination techniques [e.g., *Nature*, 326, 6110, 295 (1987), *Cell*, 51, 3, 503 (1987)] can be prepared [e.g., *Nature*, 350, 6315, 243 (1991)].

Using the embryonic stem cell clone prepared in this manner, a chimeric individual comprising the embryonic stem cell clone and a normal cell can be prepared by a method such as an injection chimera method into blastocyst of fertilized egg of an animal or an assembly chimera method. An individual having an optional mutation in the DNA encoding the polypeptide of the present invention on chromosomes of the whole body cells can be obtained by crossing this chimeric individual with a normal individual, and a homologous individual (non-human knockout animal) in which a mutation is introduced into both of homologous chromosomes can be obtained by further crossing the individuals.

In this way, a mutation can be introduced into any position of the DNA encoding the polypeptide of the present invention on the chromosome of an animal individual. For example, mutation such as nucleotide substitution, deletion or insertion can be introduced into a translation region of the DNA encoding the polypeptide of the present invention on the chromosome.

Also, the degree, time, tissue specificity and the like of the expression can be modified by introducing similar mutation into the expression controlling region. Furthermore, it is possible to control the expressing time, expressing site, expression level and the like more positively in combination with a Cre-loxP system. Examples of this method include a method in which a promoter which is expressed in a specific region in the brain is used, and the objective gene is deleted only in this region [*Cell*, 87, 7, 1317 (1996)] and a method in which the objective gene is deleted organ-specifically at the intended stage using a Cre-expressing adenovirus [*Science*, 278, 5335, (1997)].

Accordingly, expression of a DNA encoding the polypeptide of the present invention on the chromosome can also be controlled at any stage and in a tissue in this manner. Also, it is possible to prepare an animal individual having any insertion, deletion or substitution in the translation region or expression controlling region.

Such an animal can induce symptoms of various diseases caused by the polypeptide of the present invention at any stage at any degree in any region. Thus, the non-human knockout animal of the present invention becomes a markedly useful experimental animal for the treatment and prevention of various diseases caused by the polypeptide of the present invention. Particularly, it is markedly useful as an evaluation model of therapeutic agents and preventive agents and physiologically functional foods, healthy foods and the like.

(11) Gene Therapy Agent which Comprises the DNA of the Present Invention and an RNA Comprising a Sequence Homologous to the DNA The gene therapy agent using a virus vector which comprises the DNA of the present invention and an RNA comprising a sequence homologous to the DNA can be produced by mixing the recombinant virus vectors prepared in the (7) with a base material used in gene therapy agents [*Nature Genet.*, 8, 42 (1994)]. The gene therapy agent using a virus vector which comprises the DNA of the present invention and an RNA comprising a sequence homologous to the DNA can be used as a medicament for treating or preventing diseases which accompany changes in the expression of the polypeptide of the present invention or of a DNA encoding the polypeptide such as inflammatory disease, cancer and tumor metastasis.

As the base material used in the gene therapy agents, any base material can be used, so long as it is a base material generally used in injections. Examples include distilled water, a salt solution such as sodium chloride or a mixture of sodium chloride and an inorganic salt, a sugar solution such as mannitol, lactose, dextran or glucose, an amino acid solution such as glycine or arginine, a mixed solution of an organic acid solution or a salt solution with a glucose solution and the like. Also, injections may be prepared according to the conventional method as solutions, suspensions or dispersions using an auxiliary agent including an osmotic pressure controlling agent, a pH adjusting agent, a plant oil such as sesame oil or soybean oil, lecithin, and a surfactant such as a nonionic surfactant in these base materials. These injections can also be prepared as solid preparations for dissolving when used, by powdering, freeze drying or the like. The gene therapy agent of the present invention can be used directly in the treatment when it is a liquid, or when it is a solid, by dissolving it just before the gene therapy in the above base material sterilized, if necessary. The administration method of the gene therapy agent of the present invention includes a topical administration method to effect its absorption into the treating region of a patient.

A virus vector can be prepared by preparing a complex through the combination of the DNA of the present invention having an appropriate size with a polylysine-conjugate antibody specific for the adenovirus hexon protein, and linking the thus obtained complex to an adenovirus vector. The virus vector stably reaches the target cell and is incorporated into the cell by endosome and degraded inside the cell, so that it can express the gene efficiently.

As the RNA virus vectors other than retrovirus vectors, virus vectors based on Sendai virus as a (−) chain RNA virus have been developed (Japanese Patent Application No. 9-517213, Japanese Patent Application No. 9-517214), so that a Sendai virus vector into which the DNA of the present invention is inserted for the purpose of gene therapy can be prepared.

The DNA can also be transported into foci by a non-viral gene transfer method.

Examples of the non-viral gene transfer method well known in the field include calcium phosphate coprecipitation method [*Virology*, 52, 456-467 (1973); *Science*, 209, 1414-1422 (1980)], micro-injection methods [*Proc. Natl. Acad. Sci. USA*, 77, 5399-5403 (1980); *Proc. Natl. Acad. Sci. USA*, 77, 7380-7384 (1980); *Cell*, 27, 223-231 (1981); *Nature*, 294, 92-94 (1981)], membrane fusion-mediated transfer methods via liposome [*Proc. Natl. Acad. Sci. USA*, 84, 7413-7417 (1987); *Biochemistry*, 28, 9508-9514 (1989); *J. Biol. Chem.*, 264, 12126-12129 (1989); *Hum. Gene Ther.*, 3, 267-275 (1992); *Science*, 249, 1285-1288 (1990); *Circulation*, 83, 2007-2011 (1992)], direct DNA incorporation and receptor-mediated DNA transfer methods [*Science*, 247, 1465-1468 (1990); *J. Biol. Chem.*, 266, 14338-14342 (1991); *Proc. Natl. Acad. Sci. USA*, 87, 3655-3659 (1991); *J. Biol. Chem.*, 264, 16985-16987 (1989); *BioTechniques*, 11, 474-485 (1991); *Proc. Natl. Acad. Sci. USA*, 87, 3410-3414 (1990); *Proc. Natl. Acad. Sci. USA*, 88, 4255-4259 (1991); *Proc. Natl. Acad. Sci. USA*, 87, 4033-4037 (1990); *Proc. Natl. Acad. Sci. USA*, 88, 8850-8854 (1991); *Hum. Gene Ther.*, 3, 147-154 (1991)] and the like.

Regarding the membrane fusion-mediated transfer method via liposome, it has been reported based on a study on tumors that, topical incorporation and expression of a gene in a tissue is possible by directly administering a liposome preparation to the tissue as the target [*Hum. Gene Ther.*, 3, 399-410 (1992)]. Accordingly, similar effect is expected also in foci of diseases relating to the DNA and polypeptide of the present invention. A direct DNA incorporation is preferable for directly targeting the DNA at a focus. The receptor-mediated DNA transfer is carried out, for example, by conjugating a DNA (in general, it has a form of covalently closed super-coiled plasmid) with a protein ligand via a polylysine. The ligand is selected based on the presence of a corresponding ligand receptor on the cell surface of a target cell or tissue. The ligand-DNA conjugate can be injected directly to a blood vessel as occasion demands and can be directed to a target tissue where receptor binding and inherence of DNA-protein complex occur. In order to prevent intracellular degradation of DNA, the endosome function can be destroyed by simultaneous infection with adenovirus.

The above gene therapy agent which comprises the DNA of the present invention, an RNA comprising a sequence homologous to the DNA, a recombinant vector comprising the nucleic acid or the like is introduced into cells and a polypeptide encoded by the DNA, differentiation is expressed, so that mutual recognition, migration and the like of the cells can be controlled. Examples of the cells in this case include corpuscles, nerve cells, stem cells cancer cells and the like.

In addition, differentiation of promyelocyte into granulocyte can be accelerated by introducing the above gene therapy agent into promyelocyte and expressing therein.

The present invention is specifically described in based on Examples. However, the examples are for descriptions and do not limit the technical scope of the present invention.

BRIEF DESCRIPTION OF THE DRAWINGS

FIG. 1 shows a result of the FACS analysis of the expression level of poly-N-acetyllactosamine sugar chains in HCT-15 cells transfected with a G6 polypeptide expression plasmid.

FIG. 2 shows a result of the examination on the participation of G6 polypeptide in the synthesis of a glycoprotein sugar chain or glycolipid sugar chain by treating HCT-15 cells transfected with a G6 polypeptide expression plasmid with various sugar chain synthesis inhibitors and then analyzing the expression level of a poly-N-acetyllactosamine sugar chain by using FACS.

BEST MODE FOR CARRYING OUT THE INVENTION

Figure 3A:
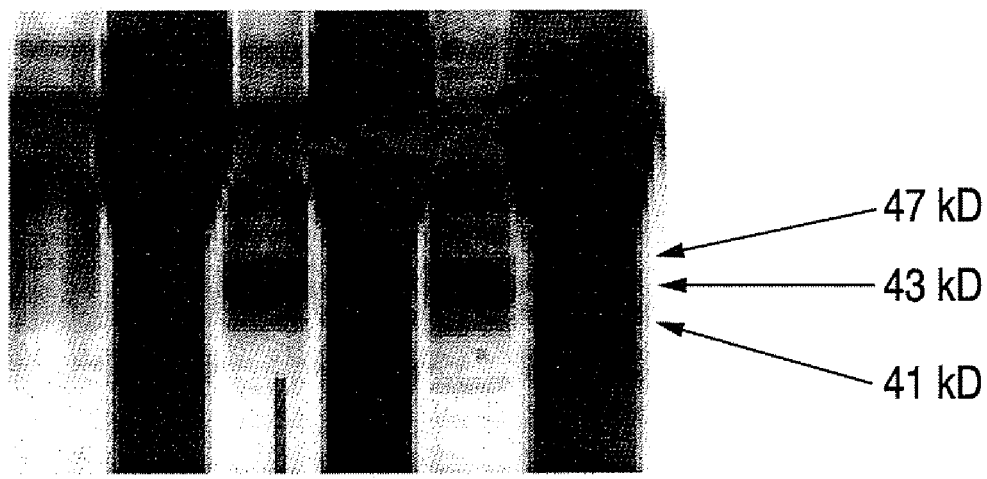
FIG. 3 shows a result of an experiment carried out by purifying a secreted FLAG peptide-fused G6 polypeptide produced in insect cells, and subjecting it to SDS polyacrylamide gel electrophoresis and then to silver staining. B shows a result of a test carried out by purifying a secreted FLAG peptide-fused G6 polypeptide produced in insect cells, and subjecting it to SDS polyacrylamide gel electrophoresis and then to Western blotting by using an anti-FLAG peptide antibody.

Unless otherwise indicated, the known methods described in *Molecular Cloning*, Second Edition were used as the genetic engineering techniques described as follows.

EXAMPLE 1

Cloning of β1,3-galactosyltransferase Homologue (Rat G6) Gene from a Rat Tibia-derived cDNA Library:

(1) Preparation of RNA

From rat tibia, 2.2 mg of total RNA was prepared by the guanidine thiocyanate-cesium trifluoroacetate method [*Methods in Enzymology*, 154, 3 (1987)]. Next, 15.7 μg of mRNA was obtained as poly(A)+ RNA by passing 2.0 mg of the total RNA through an oligo(dT) cellulose column (manufactured by Collaborative Research).

(2) Preparation of cDNA Library

Using 4.0 μg of the mRNA obtained in the above (1), synthesis of cDNA, ligation of BamHI adapter and digestion with NotI were carried out according to the linker primer method [*Preparation Methods of Gene Library (Idenshi Library no Sakusei-ho)*, edited by Hirosho Nojima, Yodo-sha, 1994]. A cDNA library in which 5'-terminal of cDNA is always present in the BamHI site side of the vector was constructed by inserting the thus obtained double-stranded cDNA between BamHI site and NotI site of a plasmid pBluescript II SK(−). As a host for cDNA library construction, *Escherichia coli* MC1061A [Molecular Cloning Second Edition] was used.

(3) Random Sequence

Plasmid DNAs were obtained from each of the *E. coli* clones obtained in the above (2) according to a conventional method, and 300- to 400-bp nucleotide sequences of the 5'-terminal and 3'-terminal sides of cDNA contained in each plasmid were determined. The nucleotide sequence was determined by using a commercially available kit (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, manufactured by PE Biosystems) and a DNA sequencer (ABI PRISM 377, manufactured by PE Biosystems). As the primers, T3 primer (manufactured by STRATAGENE) and T7 primer (manufactured by STRATAGENE) were used.

Genes and proteins having homology were analyzed by using the programs of BLAST [*J. Mol. Biol.*, 215, 403-410 (1990)] for the thus obtained nucleotide sequences, or FrameSearch [manufactured by Compugen] for amino acid sequences deduced from the nucleotide sequences. As a result, it was considered that a cDNA contained in a plasmid named OVX2-038 encodes a protein having homology with a β1,3-galactosyltransferase β3Gal-T1 (alias WM1: Japanese Published Unexamined Patent Application No. 181759/94). A nucleotide sequence (738 bp) of the cDNA contained in OVX2-038 is shown in SEQ ID NO:3, and an amino acid sequence of a polypeptide considered to be encoded by the DNA is shown in SEQ ID NO:32. It was considered that the cDNA contained in OVX2-038 is a partial fragment of a cDNA encoding a rat β1,3-galactosyltransferase homologue (named rat G6).

EXAMPLE 2

Search of Gene Encoding Human G6:

Human G6 gene corresponding to the rat G6 cDNA obtained in Example 1 was searched. As a result of the search of genes having homology with the nucleotide sequence (represented by SEQ ID NO:3) of the cDNA contained in OVX2-038 obtained in Example 1, or genes having a possibility to encode polypeptides having homology with the polypeptide (represented by SEQ ID NO:32) considered to be encoded by the cDNA at amino acid level from gene data bases by using the programs of BLAST [*J. Mol. Biol.*, 215, 403-410 (1990)] and FrameSearch [manufactured by Compugen], one EST (expressed sequence tag) sequence (GenBank No. AI039637) was found. Since the EST sequence is 428 bp, a total amino acid sequence of a polypeptide encoded by a gene corresponding to this EST and the function of the polypeptide cannot be found from this sequence information alone.

EXAMPLE 3

Cloning of Human G6 cDNA:

Cloning of candidate gene fragments was attempted by designing a primer set specific for the EST sequence (GenBank No. AI03937) found in Example 2. As the primers, CB-462 having the nucleotide sequence represented by SEQ ID NO:4 and CB-464 having the nucleotide sequence represented by SEQ ID NO:5 were used. Using the primer set, the presence of human G6 cDNA was examined by PCR by using single-stranded cDNAs prepared from various organs, or various cDNA libraries, as templates. As a result, a DNA fragment of about 250 bp was amplified when a cDNA library derived from a human colon cancer cell line Colo205 or a cDNA library derived from human gastric mucosa was used as a template.

A human G6 cDNA clone of about 3 kb was obtained by screening the above two cDNA libraries by using the amplified fragment as a probe. Since the clone was lacking the 5'-terminal portion, a 5'-terminal side DNA of the human G6 cDNA was obtained by using 5' RACE method. Full-length sequence of the human G6 cDNA (SEQ ID NO:2) was determined by sequencing the cDNA clone of about 3 kb of human G6 cDNA and the 5'-terminal side DNA, and connecting these sequences. A DNA fragment containing entire coding regions was obtained by PCR by using primers constructed based on the sequence. The absence of mutation in the nucleotide sequence derived by PCR was confirmed by sequencing the fragment. Specific methods are shown below.

(1) Preparation of a cDNA Library Derived from Human Colon Cancer Cell Line Colo205 and Analysis by PCR About 30 µg of mRNA was obtained from the human colon cancer cell line Colo205 by using a mRNA extraction kit Oligotex™-dT30<super> (manufactured by Roche). Specific reagents and method are as described in the instructions attached to the kit. Using 8 µg of the thus obtained mRNA and SUPERSCRIPT Choice System for cDNA Synthesis Kit (manufactured by GIBCO BRL), double-stranded cDNAs were synthesized using oligo(dT) as a primer.

An SfiI linker was ligated to both ends of the double-stranded cDNAs by the following method. A single-stranded DNA (11 nucleotides) having the nucleotide sequence represented by SEQ ID NO:6 and a single-stranded DNA (8 nucleotides) having the nucleotide sequence represented by SEQ ID NO:7, which constitute the SfiI linker were synthesized by using 380A DNA synthesizer (manufactured by Applied Biosystems).

Fifty micrograms of the respective synthesized single-stranded DNAs at 50 µg were separately dissolved in 50 µl of a buffer containing 50 mmol/l Tris-HCl (pH 7.5), 10 mmol/l $MgCl_2$, 5 mmol/l dithiothreitol (hereinafter referred to as "DTT"), 0.1 mmol/l EDTA (ethylenediaminetetraacetic acid) and 1 mmol/l ATP (hereinafter referred to as "T4 kinase buffer"), and the 5'-end was phosphorylated by adding 30 units of T4 polynucleotide kinase (manufactured by Takara Shuzo) and carrying out the phosphorylation reaction at 37° C. for 16 hours.

In 45 µl of the T4 ligase buffer, 4 µg of the synthetic DNA of 11 nucleotides and 2.9 µg of synthetic DNA of 8 nucleotides whose 5'-ends were phosphorylated, and the double-stranded cDNAs synthesized in the above were dissolved, and then 1,050 units of T4 DNA ligase was added thereto for reaction at 16° C. for 16 hours to thereby ligate the SfiI linker to each of the double-stranded cDNAs.

DNA fragments of about 1.5 kb or more were recovered by subjecting the thus obtained reaction solution to agarose gel electrophoresis.

In 590 µl of a buffer solution comprising 10 mmol/l Tris-HCl (pH 7.5), 6 mmol/l $MgCl_2$, 50 mmol/l NaCl and 6 mmol/l 12-mercaptoethanol (hereinafter referred to as "Y-50 buffer"), 24 µg of an expression cloning vector pAMo [*J. Biol. Chem.*, 268, 22782 (1003), alias pAMoPRC3Sc (Japanese Published Unexamined Patent Application No. 336963/93)] was dissolved, and then 80 units of SfiI (manufactured by Takara Shuzo, hereinafter, unless otherwise indicated, restriction enzymes manufactured by Takara Shuzo were used) was added thereto for digestion at 37° C. for 16 hours.

To the reaction solution, 40 units of BamHI were added, and the digestion was carried out 37° C. for 2 hours. A DNA fragment of about 8.8 kb was recovered by subjecting the reaction solution to agarose gel electrophoresis.

After each of the SfiI linker-added double-stranded cDNAs prepared in the above (derived from 8 µg of mRNA) was dissolved in 250 µl of the T4 ligase buffer, 2 µg of the DNA fragment of about 8.8 kb and 2,000 units of T4 DNA ligase were added to each of the solutions, and the ligation reaction was carried out at 16° C. for 16 hours.

After the reaction, 5 µg of transfer RNA (tRNA) was added to each of the reaction solutions and subjected to ethanol precipitation, and the precipitate was dissolved in 200 µl of a buffer comprising 10 mmol/l Tris-HCl (pH 8.0) and 1 mmol/l EDTA (hereinafter referred to as "TE buffer").

Using the reaction solution, *E. coli* LE392 (*Molecular Cloning*, Second Edition) was transformed by electroporation [*Nucleic Acids Res.*, 16, 6127 (1988)] to give about one million transformants having ampicillin resistance, and thus a cDNA library was constructed.

Subsequently, cDNA-containing plasmids were prepared using the cDNA library (*E. coli*) and a plasmid preparation kit/plasmid/maxi kit (manufactured by QIAGEN, product No. 41031).

The presence of human G6 cDNA was examined by PCR using the plasmid DNAs as templates and CB-462 having the nucleotide sequence represented by SEQ ID NO:4 and CB-464 having the nucleotide sequence represented by SEQ ID NO:5 as primers. The PCR was carried out under the following conditions. A reaction solution (50 µl) comprising 10 ng/ml of the plasmid DNA, 10 mmol/l Tris-HCl (pH 8.3), 50 mmol/l KCl, 1.5 mmol/l $MgCl_2$, 0.2 mmol/l dNTP, 0.001% (w/v) of gelatin, 0.2 µmol/l human G6 gene specific primers (CB-462 and CB-464) and 1 unit of AmpliTaq Gold DNA polymerase (manufactured by Perkin Elmer) was heated at 95° C. for 11 minutes, and then 50 cycles of the reaction was carried out, each cycle consisting of 30 seconds at 95° C., 1 minute at 55° C. and 2 minutes at 72° C. As a result of the PCR, a DNA fragment of about 250 bp considered to be derived from human G6 cDNA was amplified from several pools.

(2) Production of a Human Gastric Mucosa cDNA Library

A human gastric mucosa cDNA library was produced as follows. A cDNA was synthesized from human gastric mucosa poly(A)$^+$ RNA using cDNA Synthesis System (manufactured by GIBCO BRL), and after adding an EcoRI-NotI-SalI adapter (Super Choice System for cDNA Synthesis; manufactured by GIBCO BRL) to both ends thereof, inserted into the EcoRI site of a cloning vector λZAP II (λZAP II/EcoRI/CIAP Cloning Kit, manufactured by STRATAGENE) and then subjected to in vitro packaging using Gigapack III Gold Packaging Extract (manufactured by STRATAGENE) to thereby produce a cDNA library.

The gastric mucosa cDNA library (phage library) was divided into pools each containing about 50,000 independent clones, and then PCR was carried out using the phage (about $1 \times 10^7$ particles) of each pool as a template. The method was similar to the method described in the above (1), except that the phage (about $1 \times 10^7$ particles) heat-treated at 99° C. for 10 minutes was used as a template. As a result of the PCR, a DNA fragment of about 250 bp considered to be derived from human G6 cDNA was amplified from several pools. The DNA fragment was purified using Prep-A-Gene DNA Purification Kit (manufactured by BIO RAD) and digested with a restriction enzyme (AvaII or RsaI) to confirm that the amplified fragment has a partial sequence (the sequence of positions 946 to 1196 of SEQ ID NO:2, 251 bp) of the above EST sequence (GenBank No. AI039637). The amplified fragment was digested into 3 DNA fragments Of 96 bp, 80 bp and 72 bp by AvaII digestion, and into 2 DNA fragments of 176 bp and 72 bp by RsaI digestion.

(3) Cloning of human G6 cDNA

Using Multiprime DNA Labelling System (manufactured by Amersham Pharmacia Biotech), the PCR-amplified DNA fragment of about 250 bp obtained in the above (2) was labeled with a radioisotope to prepare a probe. The DNA fragment (50 ng) and 50 μl of a reaction solution containing a random primer and radioisotope ([α-$^{32}$P]dCTP) were allowed to react at 37° C. for 30 minutes. The composition of the reaction solution and the handling are as described in the manufacture's instructions attached to the kit. Next, the reaction was stopped by voltex, and the radioisotope-labeled probe was purified by gel filtration using a Sephadex G50 column.

Plaque hybridization was carried out by using the radioisotope-labeled probe on 7 pools (a total of about 350,000 independent clones) of the gastric mucosa cDNA library in which amplification was found in the above (2).

Filters (Biodine A: manufactured by PALL) on which plaque-derived DNAs were transferred were soaked in 25 ml of a buffer comprising 5-folds concentration SSPE [composition of 1-fold concentration SSPE comprises 180 mmol/l sodium chloride, 10 mmol/l sodium dihydrogenphosphate and 1 mmol/l EDTA (pH 7.4)], 5-folds concentration Denhardt solution [composition of 1-fold Denhardt solution comprises 0.02% (w/v) bovine serum albumin, 0.02% (w/v) Ficoll 400 and 0.02% (w/v) polyvinyl pyrrolidone], 0.5% sodium dodecyl sulfate (SDS) and 20 μg/ml salmon sperm DNA (hereinafter referred to as "hybridization buffer"), and pre-hybridization was carried out at 65° C. for 1 hour.

Next, the filters were soaked in 10 ml of the hybridization buffer containing the radioisotope-labeled probe prepared in the above, and hybridization was carried out at 65° C. for 16 hours.

Thereafter, the filters was washed twice under conditions of soaking it at 42° C. for 20 minutes in a buffer solution comprising 0.1-fold concentration SSC [composition of 1-fold concentration SSC comprises 15 mmol/l sodium citrate and 150 mmol/l sodium chloride (pH 7.0)] and 0.1% SDS.

As a result of the plaque hybridization, 11 hybridizing independent phage clones were obtained. Each phage clone was converted into a plasmid clone by carrying out in vivo excision using a kit manufactured by STRATAGENE. Thus, a plasmid in which an insert cDNA of each phage clone is inserted into pbluescript SK(−) can be obtained. The method followed the manufacture's instructions attached to the kit.

The size of cDNA contained in each plasmid was examined by digesting the thus obtained 11 plasmids with a restriction enzyme EcoRI. As a result, it was found that all plasmids contain a cDNA of about 3 kb. From the digestion patterns with plural restriction enzymes (PstI, HindIII and BsmI), it was considered that all of the 11 plasmids are identical. One of these plasmids was named pBS-G6s.

(4) Determination of Nucleotide Sequence of cDNA Inserted into Plasmid pBS-G6s

A full nucleotide sequence of the cDNA contained in pBS-G6s was determined by the following method.

Using primers specific for a sequence in pBluescript SK(−) [M13(−20) Primer and M13 Reverse Primer: manufactured by TOYOBO], 5'-terminal and 3'-terminal sequences of the cDNA were determined. Synthetic DNAs specific for the determined sequences were prepared and used as primers, and further continuing nucleotide sequences were determined. A complete nucleotide sequence of the cDNA was determined by repeating the process.

A DNA sequencer Model 4000L (manufactured by LI-COR) and a reaction kit (Sequitherm EXCELL II™ Long-Read™ DNA-sequencing kit-Lc: manufactured by Air Brown) or a DNA sequencer 377 (manufactured by Perkin Elmer) and a reaction kit (ABI Prism™ BigDye™ Terminator Cycle Sequencing Ready Reaction Kit: manufactured by Applied Biosystems) were used for the determination of the nucleotide sequence.

It was revealed that the cDNA contained in pBS-G6s has a nucleotide sequence (total nucleotide sequence 2,762 bp) of positions 289 to 3,750 in SEQ ID NO:2. It was considered, based on the nucleotide sequence, that the cDNA encodes a human β1,3-galactosyltransferase homologue (human G6), but it was lacking an N-terminal side polypeptide region.

(5) Cloning of Full-length cDNA of Human G6

From the result of the above (1), it was found that a human G6 transcript is expressed in a colon cancer cell line Colo205. Accordingly, 5' RACE method using total RNA of Colo205 as the template was carried out to obtain a 5'-terminal DNA fragment of human G6 cDNA. The 5' RACE method was carried out using a kit (5'-RACE Systems for Rapid Amplification of cDNA Ends, Version 2; manufactured by Life Technologies).

As G6 cDNA specific primers, synthetic DNAs having the nucleotide sequences shown in SEQ ID NOs:8 and 9 were used. As a result, a DNA fragment of about 460 bp was amplified. The DNA fragment was blunt-ended according to a conventional method and then inserted into the EcoRV site of pBluescript SK (−). Next, the cDNA was sequenced using primers specific for a sequence in pBluescript SK(−) [M13(−20) Primer and M13 Reverse Primer: manufactured by TOYOBO]. A DNA sequencer Model 4000L (manufactured by LI-COR) or a DNA sequencer 377 (manufactured by Perkin Elmer) and a reaction kit for each sequencer were used or sequencing. The DNA fragment (named RO2-16) has a nucleotide sequence (total nucleotide sequence 457 bp) of positions 513 to 969 in SEQ ID NO:2. The DNA fragment was unable to cover the N-terminal region of the G6 polypeptide. Accordingly, the following test was carried out.

A 5'-terminal side DNA fragment of the human G6 cDNA can be amplified by PCR using the gastric mucosa cDNA library constructed in the above (2) as a template, and a primer specific for the vector and a primer specific for the human G6 cDNA. Specifically, M13 Reverse Primer (manufactured by TOYOBO) which is a primer specific for a sequence in pBluescript SK(−) was used as a primer specific for the vector, and a synthetic DNA having the nucleotide sequence represented by SEQ ID NO:10 as the primer specific for human G6 cDNA. The PCR was carried out using 50 ng/ml of the cDNA library (plasmid) as a template under the conditions described in the above (1). Next, PCR was carried out using 1 μl of the PCR solution as a template, and M13 Reverse Primer (manufactured by TOYOBO) as a primer specific for a sequence in pBluescript SK(−) and a synthetic DNA having the nucleotide sequence represented by SEQ ID NO:9 as a primer specific for the human G6 cDNA. The PCR was carried out under the conditions described in the above (1). As a result, a DNA fragment of about 1 kb was amplified.

The DNA fragment was blunt-ended according to a conventional method and then inserted into the EcoRV site of pBluescript SK (−). Next, the DNA fragment was sequenced using a primer specific for a sequence in pBluescript SK(−)

[M13(−20) Primer or M13 Reverse Primer: both manufactured by TOYOBO]. A synthetic DNA specific for the determined sequence was prepared and used as a primer, and further continuing nucleotide sequences were determined. A complete nucleotide sequence of the DNA fragment was determined by repeating the process. A DNA sequencer Model 4000L (manufactured by LI-COR) or a DNA sequencer 377 (manufactured by Perkin Elmer) and a reaction kit for each sequencer were used for sequencing. The DNA fragment (named No. 19) has a nucleotide sequence (total nucleotide sequence 969 bp) of positions 1 to 969 in SEQ ID NO:2.

A nucleotide sequence of cDNA encoding the full-length G6 polypeptide was determined by connecting the thus determined sequence of cDNA contained in pBS-G6s, the sequence of PCR fragment determined in the above (2), the sequence of RO2-16 and the sequence of No. 19. The thus determined nucleotide sequence of human G6 full-length cDNA (3,750 bp) is shown in SEQ ID NO:2. The cDNA encoded a polypeptide comprising 378 amino acids having structure characteristic to glycosyltransferase. This polypeptide is called G6 polypeptide, and its amino acid sequence is shown in SEQ ID NO:1.

In order to obtain a DNA encoding the full-length G6 polypeptide, PCR was carried out using the cDNA library of human colon cancer cell line Colo205 as a template and primers specific for the human G6 cDNA. Specifically, PCR was carried out by heating 50 μl of a reaction solution containing 50 ng/ml of the cDNA library (plasmid), primers including an EcoRI recognition sequence [CB-497 (SEQ ID NO:11) and CB-501 (SEQ ID NO:12)] and Platinum Pfx DNA polymerase (manufactured by GIBCO BRL) (detailed composition is described in the Platinum Pfx DNA polymerase kit) at 94° C. for 2 minutes and then carrying out 45 cycles of the reaction, each cycle consisting of 20 seconds at 94° C., 45 seconds at 55° C. and 2 minutes at 68° C. As a result, a DNA fragment of about 1.3 kb was amplified. The fragment was digested with EcoRI and then inserted into the EcoRI site of pBluescript SK(−) to obtain a plasmid pBS-G6. As a result of sequencing the inserted DNA fragment, it was confirmed that the DNA fragment has a nucleotide sequence of position 46 to 1,372 in SEQ ID NO:2. A DNA sequencer 377 (manufactured by Perkin Elmer), a reaction kit for the sequencer and human G6 cDNA-specific primers were used for sequencing. The DNA fragment encoded a polypeptide comprising 378 amino acids having structure characteristic to glycosyltransferase. This polypeptide was possessed of the same amino acid sequence of G6 polypeptide. The absence of errors in the sequence of the PCR-amplified DNA fragment inserted into pBS-G6 was confirmed by carrying out direct sequencing using the PCR-amplified DNA fragment of about 1.3 kb.

A nucleotide sequence of cDNA encoding the full-length G6 polypeptide was determined by connecting the thus determined sequence of cDNA contained in pBS-G6s, the sequence of PCR fragment determined in the above (2), the sequence of No. 19 and the sequence of PCR-amplified DNA fragment contained in pBS-G6. The thus determined nucleotide sequence of human G6 full-length cDNA (3,750 bp) was the same as the nucleotide sequence of SEQ ID NO:2.

EXAMPLE 4

Homology Analysis:

The G6 polypeptide showed homologies of 35.6%, 32.8%, 30.8%, 30.3% and 33.9% at amino acid level with so far cloned five human β1,3-galactosyltransferases β3Gal-T1 (Japanese Published Unexamined Patent Application No. 181759/94), β3Gal-T2 [*J. Biol. Chem.*, 273, 433-440 (1998), *J. Biol. Chem.*, 273, 12770-12778 (1998)], β3Gal-T3 [*J. Biol. Chem.*, 273, 12770-12778 (1998)], β3Gal-T4 [*J. Biol. Chem.*, 273, 12770-12778 (1998)] and β3Gal-T5 [*J. Biol. Chem.*, 214, 12499-12507 (1999)], respectively. Also, the polypeptide showed a homology of 29.4% at amino acid level with so far cloned human 1,3-N-acetylglucosaminyltransferase (β3GnT1) [*Proc. Natl. Acad. Sci. USA*, 96, 406-411 (1999)].

It is considered from the amino acid sequence (SEQ ID NO:1) that the G6 polypeptide is a type II membrane protein characteristic to glycosyltransferase. It was considered that it comprises an N-terminal cytoplasmic region containing 14 amino acids, subsequent membrane-binding region containing 18 amino acids rich in hydrophobic property, a stem region containing at least 12 amino acids and the remaining most part of the C-terminal region containing a catalytic region. Based on the comparison of amino acid sequences with the above glycosyltransferases having a homology and information on stem regions and catalytic regions of the above glycosyltransferases (Japanese Published Unexamined Patent Application No. 181759/94), it was assumed that the stem region contains at least 12 amino acids. Accordingly, it is considered that the polypeptide comprising an amino acid sequence of positions 45 to 378 contains a catalytic region.

Based on these results and the results of Examples 6, 7, 9 and 10 which are described below, it was found that the polypeptide is a novel β1,3-N-acetylglucosaminyltransferase and the polypeptides comprising amino acid sequences of positions 36 to 378 in SEQ ID NO:1 and 39 to 378 in SEQ ID NO:1 are secretory polypeptides.

EXAMPLE 5

Construction of Expression Plasmids for Animal Cells:

In order to express the G6 polypeptide encoded by the human G6 cDNA obtained in Example 3 in animal cells, an expression plasmid was constructed by introducing human G6 cDNA into an expression plasmid pAMo [*J. Biol. Chem.*, 268, 22782 (1993), alias pAMoPRC3Sc (Japanese Published Unexamined Patent Application No. 336963/93)] or pCXN2 [*Gene*, 108, 193 (1991)].

(1) Construction of a Plasmid pAMo-G6 for Expressing G6 Polypeptide

The pBS-G6 was digested with a restriction enzyme EcoRI and then converted to be blunt-ended by using a DNA polymerase Klenow fragment. Thereafter, a SfiI fragment of about 1,350 bp was obtained by adding the SfiI linker prepared in Example 3(1). Separately, pAMo was digested with SfiI and BamHI and then an SfiI fragment of 8.7 kb was obtained. An expression plasmid pAMo-G6 was constructed by ligating the two fragments.

(2) Construction of a Plasmid pCXN2-G6 for Expressing G6 Polypeptide

The pBS-G6 was digested with a restriction enzyme EcoRI and then an EcoRI fragment of about 1,330 bp was obtained. Separately, pCXN2 was digested with EcoRI and then an EcoRI fragment of about 3 kb was obtained. An expression plasmid pCXN2-G6 was constructed by ligating the two fragments.

EXAMPLE 6

Synthesis of a poly-N-acetyllactosamine Sugar Chain in Human Culture Cells Transfected with a G6 Polypeptide Expression Plasmid:

(1) Preparation of Stable Transformant Using Namalwa Cell as a Host

Each of a control plasmid (pAMo) and the G6 polypeptide expression plasmid (pAMo-G6) constructed in Example 5 was dissolved in TE buffer to give a concentration of 1 µg/µl and then transfected into a human B cell line Namalwa cell by electroporation [*Cytotechnology*, 3, 133 (1990)] to obtain transformed cells.

After the plasmids were transfected at 4 µg per $1.6 \times 10^6$ cells, the cells were suspended in 8 ml of 10% fetal bovine serum-containing RPMI 1640 medium [RPMI 1640 medium (manufactured by Nissui Pharmaceutical) supplemented with 1/40 volume of 7.5% $NaHCO_3$, 3% 200 mmol/l L-glutamine solution (manufactured by GIBCO) and 0.5% penicillin-streptomycin solution (manufactured by GIBCO, 5,000 units/ml penicillin and 5,000 µg/ml streptomycin); hereinafter, RPMI 1640 medium means the RPMI 1640 medium supplemented with these additives] and cultured at 37° C. for 24 hours in a $CO_2$ incubator. After the culturing, G418 (manufactured by GIBCO) was added thereto to give a concentration of 0.8 mg/ml, followed by culturing for 14 days to obtain a stable transformant. The transformant was sub-cultured using RPMI 1640 medium containing 0.8 mg/ml G418 and 10% fetal bovine serum.

(2) Preparation of a Stable Transformant Using HCT-15 Cell as a Host

Each of a control plasmid (pCXN2) and the G6 polypeptide expression plasmid (pCXN2-G6) constructed in Example 5 was dissolved in TE buffer to give a concentration of 1 µg/µl and then transfected into a human colon cancer cell line HCT-15 cell by the electroporation method [*Cytotechnology*, 3, 133 (1990)] to obtain transformed cells.

After the plasmids were transfected at 10 µg per $8 \times 10^6$ cells, the cells were suspended in 8 ml of 10% fetal bovine serum-containing RPMI 1640 medium and cultured at 37° for 24 hours in a $CO_2$ incubator.

After the culturing, G418 (manufactured by GIBCO) was added thereto to a concentration of 0.8 mg/ml, and the culturing was continued for 20 days to obtain a stable transformant. In addition, a single clone was also obtained from the transformed cells using limiting dilution. The transformant was sub-cultured using RPMI 1640 medium containing 0.8 mg/ml of G418 and 10% of fetal bovine serum.

(3) Measurement of Expression Level of poly-N-acetyllactosamine Sugar Chains in Respective Transformed Cells An example by using an anti-i antibody (OSK28) which recognizes poly-N-acetyllactosamine sugar chains is shown below.

The HCT-15 cells transfected with pCXN2-G6 or pCXN2 prepared in the above (2) (each $5 \times 10^6$ cells) were washed by using 3 ml of a phosphate buffer PBS (8 g/l NaCl, 0.2 g/l KCl, 1.15 g/l $Na_2HPO_4$ (anhydrous) and 0.2 g/l $KH_2PO_4$).

The cells (about $1 \times 10^6$ cells) described above were put into a microtube (1.5 ml, manufactured by Eppendorf) and the cells were collected by centrifugation (550×g, 7 minutes).

The cells were washed with 0.9 ml of 0.1% sodium azide-containing PBS (A-PBS: 8 g/l NaCl, 0.2 g/l KCl, 1.15 g/l $Na_2HPO_4$ (anhydrous), 0.2 g/l $KH_2PO_4$ and 0.1% sodium azide), and then the washed cells were suspended in 100 µl of an antibody (OSK28) capable of recognizing a poly-N-acetyllactosamine sugar chain diluted with A-PBS to give a concentration of 10 µg/ml (20 times dilution of the following purified antibody) and allowed to react at 4° C. for 30 minutes in the dark.

OSK28 (a purified antibody) was obtained from Dr. Junko Takahashi at the First Research Department, Osaka Red Cross Blood Center. OSK28 is a human monoclonal antibody (IgM antibody) produced by an immortalized B-cell line established from human lymphocytes capable of producing an anti-Tja+anti-i antibodies by an EBV-hybridoma method. The purified OSK28 used in this test was purified by the method described in the Best Mode for Carrying Out the Invention (6)(i) after a large scale culturing of the above B-cell line.

After the reaction, the cells are washed twice with 3 ml of A-PBS, suspended in 100 µl of an FITC-labeled anti-human IgM antibody [manufactured by Medical & Biological Laboratories (MBL)] diluted to 10 µg/ml, and then allowed to react at 4° C. for 1 hour. After the reaction, the cells were washed twice with 3 ml of A-PBS, suspended in 200 µl of PBS containing 0.5% p-formaldehyde and then immobilized. The cells were analyzed by using FACS (Epics Elite Flow Cytometer). Also, as a control test, the same analysis was carried out by using A-PBS instead of the antibody.

HCT-15 cells transfected with the G6 polypeptide expression plasmid (pCXN2-G6) or the control plasmid pCXN2 were subjected to indirect fluorescent antibody staining by using various anti-sugar chain antibodies (OSK28, KM93, OM81, CA19-9, KM231, TT42 and 7LE) and then analyzed by using FACS, and the results are shown in FIG. 1. The FACS analysis using indirect fluorescent antibody staining was carried out according to a conventional method [*J. Biol. Chem.*, 274, 12499-12507 (1999)].

The reactivity to OSK28 was increased in the cells transfected with pCXN2-G6 in comparison with the cells transfected with pCXN2 (FIG. 1). These results mean that a poly-N-acetyllactosamine sugar chain was newly synthesized on sugar chains of a glycoprotein or glycolipid on the surface of cells by expressing the G6 polypeptide in HCT-15 cells.

On the other hand, when the fluorescent staining was carried out using CA19-9 or KM231 as an antibody against a sialyl Lewis a sugar chain, the reactivity to the antibody did not change in HCT-15 cells transfected with pCXN2-G6 and HCT-15 cells transfected with pCXN2 (FIG. 1). It is known that HCT-15 cells express α1,3/1,4-fucose transferase (Fuc-TIII), and a sialyl Lewis a sugar chain which is detected by the above antibody is synthesized when β1,3-galactosyltransferase is expressed in the cells [*J. Biol. Chem.*, 274, 12499-12507 (1999)]. Thus, the above results show that the G6 polypeptide does not have the GlcNAc β1,3-galactosyltransferase activity.

In the same manner, when the fluorescent staining was carried out by using KM93 as an antibody against a sialyl Lewis x sugar chain, PM81 as an antibody against a Lewis x sugar chain, TT42 as an antibody against a Lewis b sugar chain or 7LE as an antibody against a Lewis a sugar chain, the reactivity to the antibody also did not change in HCT-15 cells transfected with pCXN2-G6 and HCT-15 cells transfected with pCXN2 (FIG. 1).

(4) Experiments Using Sugar Chain Synthesis Inhibitors

Experiments using sugar chain synthesis inhibitors were carried out in order to examine whether the G6 polypeptide is involved in the synthesis of a glycoprotein sugar chain or a glycolipid sugar chain. The pCXN2-G6-transfected HCT-15 cell (single clone) obtained in the above (2) was cultured for 5 days in the presence of various sugar chain synthesis inhibitors, and then analysis by FACS was carried out using OSK28. An inhibitor for O-linked sugar chain of glycoproteins, benzyl-α-GalNAc (manufactured by SIGMA) was used at a concentration of 4 mmol/l. As an inhibitor for N-linked sugar chain of glycoproteins, a mannosidase II inhibitor swainsonine (manufactured by Seikagaku Corporation) was used at a concentration of 10 μg/ml. As a glycolipid sugar chain inhibitor, a glucosylceramide synthase inhibitor D-PDMP (D-threo-1-phenyl-2-decanoylamino-3-morpholino-1-propanol: manufactured by Matreya) was used at a concentration of 10 μmol/l. Also, as a negative control of D-PDMP, L-D-PDMP (L-threo-1-phenyl-2-decanoylamino-3-morpholino-1-propanol: manufactured by Matreya) was used at a concentration of 10 μmol/l. The culturing was carried out according to the method of the above (2). The results are shown in FIG. 2. As a control, the indirect fluorescent antibody staining using OSK28 was carried out on HCT-15 cells transfected with a vector (pCXN2), and the result is also shown in the drawing.

When cultured in the presence of a sugar chain synthesis inhibitor benzyl-α-GalNAc, the reactivity to OSK28 antibody was sharply reduced in comparison with the case of its absence. This result suggests that the de novo synthesis poly-N-acetyllactosamine sugar chains of G6 polypeptide-expressed observed in HCT-15 cells is occurred mainly on the O-linked sugar chains of glycoproteins. On the other hand, since the reactivity to OSK28 antibody was also reduced in swainsonine-treated cells, it suggests that the de novo synthesis of a poly-N-acetyllactosamine sugar chains observed in G6 polypeptide-expressed HCT-15 cells is also occurred on N-linked sugar chains of glycoproteins. Based on the above results, it is considered that when the G6 polypeptide is highly expressed in animal cells, a poly-N-acetyllactosamine sugar chain can be synthesized on glycoprotein sugar chains.

Furthermore, it is considered that a poly-N-acetyllactosamine sugar chain is newly synthesized also on sugar chains of glycoproteins and oligosaccharides secreted from cells in which the G6 polypeptide is expressed. Accordingly, useful secreted glycoproteins are produced by using a G6 polypeptide-expressed cell as a host, so that sugar chains containing a poly-N-acetyllactosamine sugar chain can be added to the thus produced secretory glycoproteins.

EXAMPLE 7

Measurement of β1,3-N-acetylglucosaminyltransferase Activity in Human Cultural Cells Transfected with a G6 Polypeptide Expression Plasmid:

Using a cell extract of the stable transformant cell (Namalwa cell) transfected with the G6 polypeptide expression plasmid obtained in Example 6(1), β1,3-N-acetylglucosaminyltransferase activity was measured.

(1) Activity Measurement by Using 2-aminobenzamide-labeled Oligosaccharides as Substrates The transformant cells (about $2 \times 10^7$ cells) obtained in Example 6(1) were put into a microtube (1.5 ml: manufactured by Eppendorf), and the cells were collected by centrifugation (550×g, 7 minutes). The cells were washed with 0.9 ml of PBS, the washed cells were suspended in a solution (100 μl) containing 20 mmol/l HEPES (pH 7.2) and 2% Triton X-100 and then the cells were disrupted using a sonicator (Bioruptor; manufactured by COSMO BIO). After the mixture was allowed to stand at 4° C. for 1 hour, the supernatant was obtained by centrifugation (550×g, 7 minutes). The supernatant was used as an enzyme sample.

A β1,3-N-acetylglucosaminyltransferase activity was measured by using this enzyme sample and 2-aminobenzamide-labeled sugar chain substrates.

The 2-aminobenzamide-labeled sugar chain substrates were prepared by using SIGMA 2AB glycan labeling kit (manufactured by Oxford Glycoscience) according to the manufacture's instructions of the kit. 2-Aminobenzamide-labeled lacto-N-neotetraose (Galβ1,4-GlcNAcβ1-3Galβ1-4Glc; hereinafter referred to as "LNnT") and Galβ1,4-GlcNAcβ1-3Galβ1-4GlcNAc (hereinafter referred sometimes to as "2LN") were used as substrates. LNnT was purchased from Oxford Glycosystems. 2LN was obtained from Seikagaku Corporation.

The activity measurement was carried out using known methods [*FEBS*, 462, 289 (1999), *J. Biol. Chem.*, 269, 14730-14737 (1994), *J. Biol. Chem.*, 267, 23507 (1992), *J. Biol. Chem.*, 267, 2994 (1992)]. Specifically, the reaction was carried out at 37° C. for 16 hours in 20 μl of an assay solution [150 mmol/l MOPS (pH 7.5), 50 mmol/l UDP-GlcNAc (manufactured by SIGMA), 20 mmol/l sodium cacodylate (pH 7.2), 0.4% Triton CF-54, 10 mmol/l $MnCl_2$, 15 mmol/l 2-aminobenzamide-labeled sugar chain substrate, the above cell extract (20 μg as protein)], and then the product was detected by high performance liquid chromatography (HPLC). The protein concentration of the cell extract was measured by using DC Protein Assay Kit (manufactured by BIO RAD) according to the manufacture's instructions of the kit.

After carrying out the reaction by using an assay solution containing UDP-GlcNAc (saccharide donor) and an assay solution containing no donor and subsequently analyzing by HPLC, peaks appeared only in the assay solution containing UDP-GlcNAc was defined as products.

The assay solution after completion of the reaction was treated at 100° C. for 5 minutes, 50 μl of pure water for HPLC was added thereto, and the mixture was centrifuged at 10,000×g for 5 minutes to obtain the supernatant. To a tube containing the assay solution, 50 μl of pure water for HPLC was again added to wash the tube, the mixture was centrifuged at 10,000×g for 5 minutes, and the resulting supernatant was combined with the first supernatant. Next, the supernatant was passed through Ultrafree-MC column (manufactured by Millipore) and a part thereof (10 μl) was subjected to HPLC. The Ultrafree-MC column was used according to the method described in the manufacture's instructions attached thereto.

The HPLC was carried out using TSK-gel ODS-80Ts Column (4.6×300 mm; manufactured by TOSOH) as a column and 7% methanol-containing 0.02 mol/l ammonium acetate buffer (pH 4.0) as an eluant at an elution temperature of 50° C. and a flow rate of 1 ml/min.

The product was detected by using a fluorescence spectrophotometer FP-920 (manufactured by JASCO Corporation) (excitation wavelength: 330 nm, radiation wavelength: 420 nm).

The product was identified by using its coincidence of elution time with that of a standard sugar chain as the marker. 2-Aminobenzamide-labeled GlcNAcβ1-3Galβ1,4-GlcNAcβ1-3Galβ1-4Glc was used as the standard sugar chain.

The product was determined by using a 2-aminobenzamide-labeled glucose polymer (manufactured by Oxford Glycoscience) as the standard and comparing the fluorescence intensities.

As a result of the activity measurement by using a cell extract of the stable transformant cells (Namalwa cells) transfected with a control plasmid (pAMo) or a G6 polypeptide expression plasmid (pAMo-G6), a ratio of the substrate (LNnT) converted into the product (GlcNAcβ1-3Galβ1,4-GlcNAcβ1-3Galβ1-4Glc) was almost 0% in the control plasmid-transfected cells, while it was increased to 6.11% in the G6 polypeptide expression plasmid-transfected cells. Also, a ratio of the other substrate (Galβ1-4GlcNAcβ1-3Galβ1,4-GlcNAc) converted into the product (GlcNAcβ1-3Galβ1,4-GlcNAcβ1-3Galβ1-4GlcNAc) was almost 0% in the control plasmid-transfected cells, while it was increased to 3.95% in the G6 polypeptide expression plasmid-introduced cells. That is, it was found that β1,3-N-acetylglucosaminyltransferase activity is increased in the G6 polypeptide expression plasmid-introduced cells in comparison with the control plasmid-introduced cells.

Based on the above results, it was confirmed that the G6 polypeptide is a novel β1,3-N-acetylglucosaminyltransferase. This result shows that a sugar chain in which N-acetylglucosamine is linked via β1,3-linkage to the galactose residue present in the non-reducing terminal of a sugar chain can be synthesized by using the G6 polypeptide.

(2) Activity Measurement Using Glycolipids as Substrates

β1,3-N-Acetylglucosaminyltransferase activity of G6 polypeptide was measured by using glycolipids as substrates according to known methods [*FEBS*, 462, 289 (1999), *J. Biol. Chem.*, 269, 14730-14737 (1994), *J. Biol. Chem.*, 267, 23507 (1992), *J. Biol. Chem.*, 267, 2994 (1992)]. Specifically, the reaction was carried out at 37° C. for 16 hours in 20 μl of reaction solution [150 mmol/l sodium cacodylate (pH 7.2), 10 mmol/l UDP-GlcNAc (manufactured by SIGMA), 480 μmol/l UDP—[$^{14}$C]GlcNAc (manufactured by Amersham), 0.4% Triton CF-54, 10 mmol/l MnCl$_2$, 250 μmol/l glycolipid, the cell extract prepared in the above (1) (20 μg as protein)]. As glycolipids, lactosylceramide (manufactured by SIGMA) and paragloboside (obtained from Yasunori Kushi at Tokyo Medical and Dental University) were used. After completion of the reaction, 200 μl of 0.1 mol/l KCl was added and lightly centrifuged to obtain the supernatant. The supernatant was passed through Sep-Pak plus C18 Cartridge (Waters), which had been washed once with 10 ml of methanol and equilibrated twice with 10 ml of 0.1 mol/l KCl, to adsorb the glycolipid in the supernatant onto the cartridge. After washing the cartridge twice with 10 ml of pure water for HPLC, the adsorbed glycolipid was eluted with 5 ml of methanol. After concentrating the eluate to about 10 μl by using a vacuum dryer, the concentrated solution was spotted on a TLC plate (HPTLC plate Silica gel 60: manufactured by MERCK) and developed using a developing solvent comprising a composition of chloroform:methanol:water (containing 0.2% CaCl$_2$)=65:35:8. After the development was carried out to a position 5 mm from the upper end of the TLC plate, the plate was dried and then the radioactivity incorporated into the glycolipid was measured using Bio Image Analyzer BAS 2000 (manufactured by Fuji Photo Film).

As a result of the activity measurement by using a cell extract of the stable transformant cells (Namalwa cells) transfected with a control plasmid (pAMo) or a G6 polypeptide expression plasmid (pAMo-G6), the activity was not detected in the cells transfected with the control plasmid when lactosylceramide was used as the substrate, but the activity was distinctively detected in the cells transfected with the G6 polypeptide expression plasmid (conversion efficiency into the product 0.125%). When paragloboside was used as a substrate, weak activity was detected even in the cells transfected with the control plasmid (conversion efficiency into the product 0.006%), but the activity was distinctively increased in the cells transfected with the G6 polypeptide expression plasmid (conversion efficiency into the product 0.126%). Based on the above results and the results of the above (1), it was confirmed that the G6 polypeptide is a novel β1,3-N-acetylglucosaminyltransferase which uses lactosylceramide and paragloboside as substrates. When the activity of G6 polypeptide using lactosylceramide as a substrate was defined as 100%, the activity using paragloboside as a substrate was 96%.

The above results show that a glycolipid in which N-acetylglucosamine is added via β1,3-linkage to the galactose residue present in the non-reducing terminal of a sugar chain such as of lactosylceramide or paragloboside can be synthesized using the G6 polypeptide.

EXAMPLE 8

Secreted Production of Flag Peptide-fused G6 Polypeptide Using Insect Cell as the Host:

It was considered based on its primary sequence that the cloned β1,3-N-acetylglucosaminyltransferase G6 comprises an N-terminal cytoplasmic region containing 14 amino acids, subsequent membrane-binding region containing 18 amino acids rich in hydrophobic property, a stem region containing at least 12 amino acids and the remaining most part of the C-terminal region including a catalytic region. Thus, secreted expression of the G6 polypeptide was carried out wherein the N-terminal cytoplasmic region containing 14 amino acids, the membrane-binding region containing 18 amino acids and a part of the stem region (3 amino acids or 6 amino acids) was removed from the G6 polypeptide, and an immunoglobulin signal sequence and FLAG peptide was added to the removed regions.

(1) Construction of a Flag Peptide Fused-secretion Vector pAMoF2 for Animal Cells A secretion vector pAMoF2 was constructed for the secreted expression of a polypeptide of interest fused with a FLAG peptide having the amino acid sequence represented by SEQ ID NO:13 at the N-terminal.

A HindIII-Asp718 fragment was obtained by digesting pAMo with HindIII and Asp718. As linkers for ligating HindIII digestion site and Asp718 digestion site, the following 6 DNAs [IgK-1 (nucleotide sequence: SEQ ID NO:14), IgK-2 (nucleotide sequence: SEQ ID NO:15), IgK-3 (nucleotide sequence: SEQ ID NO:16), IgK-4 (nucleotide sequence: SEQ ID NO:17), IgK-5 (nucleotide sequence: SEQ ID NO:18), IgK-61 (nucleotide sequence: SEQ ID NO:19)] were synthesized. Also, the linker constructed by these DNAs encodes an immunoglobulin κ signal sequence and FLAG peptide, and respective restriction enzyme digestion sites of PmaCI, StuI and SnaBI are included therein. Each of these 6 DNAs was synthesized using 380A DNA synthesizer manufactured by Applied Biosystems. The synthesized DNAs were used after phosphorylation using T4 polynucleotide kinase (manufactured by Takara Shuzo, the same shall apply hereinafter).

The plasmid pAMoF2 was constructed by ligating the 6 phosphorylated synthetic DNAs obtained in the above with the HindIII-Asp718 fragment of about 8.7 kb.

(2) Construction of a Plasmid pAMoF2-i52S

As primers for PCR, a DNA having the nucleotide sequence represented by SEQ ID NO:20 (called C12-7) and a DNA having the nucleotide sequence represented by SEQ ID NO:21 (called C12-9) were synthesized (it is possible to purchase from Sawady Technology). They are designed such that BamHI site and NotI site are included in C12-7 and C12-9, respectively.

PCR was carried out using a kit Manufactured by Takara Shuzo (GeneAmp™ DNA Amplification Reagent Kit with AmpliTaq™ Recombinant Taq Polymerase). The reaction solution was prepared according to the method of the kit, and the reaction was carried out using a DNA thermal cycler (PERKIN ELMER CETUS DNA Thermal Cycler; Available from Takara Shuzo) by carrying out 10 cycles, each cycle consisting of a reaction at 94° C. for 30 seconds, 65° C. for 1 minute and 72° C. for 2 minutes, and then a further reaction was carried out at 72° C. for 7 minutes. As a template, 10 ng of a plasmid pAMo-i (Japanese Published Unexamined Patent Application No. 236398/99) was used. A DNA fragment of about 1.1 kb was obtained by the PCR.

A plasmid pT7B-i52S No. 3 was constructed by ligating the PCR-amplified DNA fragment of about 1.1 kb to a T-vector pT7Blue (manufactured by Novagen).

Next, the plasmid pAMoF2-i52S was constructed.

A StuI-BanIII fragment of about 7.2 kb was obtained by digesting pAMoF2 with StuI and BanIII. A BanIII-NotI fragment of about 1.7 kb was obtained by digesting pAMo with BanIII and NotI. A BamHI (blunt end)-NotI fragment of about 1.1 kb was obtained by digesting pT7B-i52S No. 3 with BamHI, converting the 5' protruding end formed by the BamHI digestion to a blunt end using *E. coli* DNA polymerase I Klenow fragment, and then digesting it with NotI.

The plasmid pAMoF2-i52S was constructed by ligating the thus obtained StuI-BanIII fragment of about 7.2 kb, BanIII-NotI fragment of about 1.7 kb and BamHI (blunt end)-NotI fragment of about 1.1 kb.

(3) Construction of Plasmids pBS-G6sec1 and pBS-G6sec2

A DNA fragment encoding a region considered to have the catalytic activity of G6 polypeptide (aspartic acid at position 36 to isoleucine at position 378 in SEQ ID NO:1 or isoleucine at position 39 to isoleucine at position 378 in SEQ ID NO:1) was subcloned.

PCR was carried out by using CB-543 having the nucleotide sequence represented by SEQ ID NO:22 and CB-545 having the nucleotide sequence represented by SEQ ID NO:23 as primers and the plasmid pBS-G6 constructed in Example 3 as a template to prepare a DNA fragment of about 1.0 kb encoding a region of aspartic acid at position 36 to isoleucine at position 378 in SEQ ID NO:1. BamHI digestion site and XbaI digestion site were included in CB-543 and CB-545, respectively. The plasmid pBS-G6sec1 was constructed by digesting the PCR-amplified fragment with BamHI and XbaI and then inserted the digested products between BamHI and XbaI of a vector pBluescript SK(−).

PCR was carried out by using CB-544 having the nucleotide sequence represented by SEQ ID NO:24 and CB-545 having the nucleotide sequence represented by SEQ ID NO:25 as primers and the plasmid pBS-G6 constructed in Example 3 as a template to prepare a DNA fragment of about 1.0 kb encoding a region of isoleucine at position 39 to isoleucine at position 378 in SEQ ID NO:1. BamHI digestion site and XbaI digestion site were ligated to CB-544 and CB-545, respectively. The plasmid pBS-G6sec2 was constructed by digesting the PCR-amplified fragment with BamHI and XbaI and then inserting the digested products between BamHI and XbaI of the vector pBluescript SK(−).

Platinum Pfx DNA polymerase (manufactured by GIBCO BRL) was used in the PCR. As a template, 1 ng of the plasmid pBS-G6 was used. After 50 μl the PCR solution was heated at 94° C. for 2 minutes, 25 cycles of the reaction was carried out, each cycle consisting of a reaction at 94° C. for 20 seconds, at 55° C. for 45 seconds and at 68° C. for 2 minutes. This process was carried out according to the manufacture's instructions attached to the Platinum Pfx DNA polymerase kit.

The absence of errors by PCR was confirmed by sequencing DNA fragments inserted into pBS-G6sec1 and pBS-G6sec2.

(4) Production of a Recombinant Virus for Secreted Expression of Flag Peptide-fused G6 Polypeptide in Insect Cells A recombinant virus was prepared by two steps, namely a step (step 1) in which a DNA encoding an objective protein is inserted into a special plasmid called transfer vector, and another step (step 2) in which a recombinant virus is obtained through homologous recombination by co-transfection of the objective DNA-inserted transfer vector prepared in the step 1 and a wild type virus in an insect cell. The steps were carried out by the following procedures using BaculoGold Starter Kit (product No. PM-21001K) manufactured by Pharmingen according to the manufacture's instructions of the kit.

Step 1: Integration of a DNA encoding FLAG Peptide-fused G6 Polypeptide into a Transfer Vector Plasmids pVL1393-F2G6sec1 and pVL1393-F2G6sec2 were constructed by inserting a DNA encoding FLAG peptide-fused G6 polypeptide between BamHI site and NotI site of a transfer vector pVL1393 (manufactured by Pharmingen).

The pAMoF2-i52S prepared in the above (2) was digested with restriction enzymes HindIII and NotI to obtain a HindIII-NotI fragment of 1.2 kb.

A pVL1393 was digested with restriction enzymes BamHI and BstPI to obtain a BamHI-BstPI fragment of 3.2 kb.

A pVL1393 was digested with restriction enzymes NotI and BstPI to obtain a NotI-BstPI fragment of 6.4 kb.

As linkers for connecting BamHI site and HindIII site, the DNA fragments shown in SEQ ID NOs:26 and 27 were synthesized and the 5'-ends were phosphorylated by using T4 polynucleotide kinase.

pVL1393-F2i52S2 was constructed by ligating these 3 fragments and linkers.

A BamHI-NotI fragment of about 9.6 kb was obtained by digesting pVL1393-F2i52S2 with BamHI and NotI. Also, a BamHI-NotI fragment of about 1.0 kb was obtained by digesting pBS-G6sec1 constructed in the above (3) with restriction enzymes BamHI and NotI. A plasmid pVL1393-F2G6sec1 was constructed by ligating these 2 fragments.

A BamHI-NotI fragment of about 9.6 kb was obtained by digesting pVL1393-F2i52S2 with BamHI and NotI. Also, a BamHI-NotI fragment of about 1.0 kb was obtained by digesting pBS-G6sec2 constructed in the above (3) with restriction enzymes BamHI and NotI. A plasmid pVL1393-F2G6sec2 was constructed by ligating these 2 fragments.

Step 2: Preparation of Recombinant Virus

A recombinant baculovirus was prepared by introducing a linear baculovirus DNA (BaculoGold baculovirus DNA, manufactured by Pharmingen) and the plasmid prepared in the above (pVL1393-F2G6sec1 or pVL1393-F2G6sec2) into an insect cell Sf9 (manufactured by Pharmingen) cultured using TNM-FH insect medium (manufactured by Pharmingen) according to a lipofectin method [*Protein, Nucleic Acid and Enzyme*, 37, 2701 (1992)]. A process for producing a pVL1393-F2G6sec1-derived recombinant baculovirus is described below. A pVL1393-F2G6sec2-derived recombinant baculovirus was also produced in the same manner.

In 12 μl of distilled water, 1 to 5 μg of pVL1393-F2G6sec1 and 15 ng of the linear baculovirus DNA were dissolved, a mixture of 6 μl (6 μg) of lipofectin (manufactured by GIBCO BRL) and 6 µl of distilled water was added thereto, and the resulting mixture was allowed to stand at room temperature for 15 minutes.

About $2\times10^6$ of Sf9 cells were suspended in 2 ml of Sf900-II medium (manufactured by GIBCO BRL) and were put into a cell culture plastic dish of 35 mm in diameter, and a total volume of the mixed solution of pVL1393-F2G6sec1, linear baculovirus DNA and lipofectin was added thereto, followed by culturing at 27° C. for 3 days.

From the culture, 1 ml of the culture supernatant containing the recombinant virus was recovered.

To the dish from which the culture supernatant was recovered, 1 ml of the TNM-FH insect medium was newly added and further cultivation at 27° C. for 4 days was done. After the culturing, 1.5 ml of culture supernatant containing the recombinant virus was further recovered in the same manner.

(5) Preparation of a Recombinant Virus Solution

About $8\times10^6$ of Sf9 cells were suspended in 5 ml of EX-CELL 400 medium (manufactured by JRH), put into a 25 cm$^2$ flask (manufactured by Greiner) and allowed to stand at room temperature for 30 minutes to adhere the cells onto the flask, the supernatant was discarded, and then 1 ml of EX-CELL 400 medium and 1 ml of a culture supernatant containing the recombinant virus obtained in the above (4) were added to the flask.

After the addition, the cells and virus particles were thoroughly contacted by gently shaking at room temperature for 1 hour, and then cultured at 27° C. for 4 days by adding 4 ml of the TNM-FH insect medium.

The culture was centrifuged at 1,500×g for 10 minutes to obtain recombinant virus-infected Sf9 cells and 5.5 ml of a recombinant virus solution.

About $2\times10^7$ of Sf9 cells were suspended in 15 ml of EX-CELL 400 medium, put into a 75 cm$^2$ flask (manufactured by Greiner) and allowed to stand at room temperature for 30 minutes to adhere the cells onto the flask, the supernatant was discarded, and then 5 ml of EX-CELL 400 medium and 1 ml of the recombinant virus solution obtained in the above were added to the flask.

After the addition, the cells and virus particles were thoroughly contacted by gently shaking at room temperature for 1 hour, and 10 ml of the TNM-FH insect medium was added thereto, followed by culturing at 27° C. for 4 days. The culture was centrifuged at 1,500×g for 10 minutes to obtain recombinant virus-infected Sf9 cells and 15 ml of a recombinant virus solution.

A titer of the virus in the recombinant virus solution can be calculated by the following method (based on the manual of BaculoGold Starter Kit manufactured by Pharmingen).

About $6\times10^6$ of Sf9 cells are suspended in 4 ml of EX-CELL 400 medium, put into a cell culture plastic dish of 60 mm in diameter and allowed to stand at room temperature for 30 minutes to adhere the cells onto the dish, the supernatant is discarded, and then 400l of EX-CELL 400 medium and 100 µl of the recombinant virus solution diluted to $10^{-4}$ or $10^{-5}$ with EX-CELL 400 medium are added to the dish.

After the addition, the cells and virus particles are thoroughly contacted by gently shaking the dish at room temperature for 1 hour.

After the contact, the medium is removed from the dish, and a mixed solution of 2 ml of EX-CELL 400 medium (kept at 42° C.) containing a 2% low melting point agarose (Agarplaque Agarose; manufactured by Pharmingen) and 2 ml of TNM-FH insect medium (kept at 42° C.) is poured into the dish and allowed to stand at room temperature for 15 minutes.

After the standing, the dish is wrapped with a vinyl tape to prevent drying, put into a sealable plastic container, and cultured at 27° C. for 5 days.

After the culturing, 1 ml of PBS buffer containing 0.01% Neutral Red is added to the dish, followed by further culturing for 1 day, and then the number of formed plaques is counted.

(6) Secreted Production and Purification of a Flag Peptide-fused G6 Polypeptide

Since the G6 polypeptide encoded by the plasmid pVL1393-F2G6sec1- or plasmid pVL1393-F2G6sec2-derived recombinant virus is expressed as a secreted fusion protein with FLAG peptide, it can be easily purified using Anti-FLAG M1 Affinity Gel (manufactured by COSMO BIO).

The pVL1393-F2G6sec1-derived recombinant virus can secrete and produce a polypeptide in which a presumed catalytic region of G6 polypeptide (aspartic acid at position 36 to isoleucine at position 378 in SEQ ID NO:1) is fused to the C-terminal of a FLAG peptide containing 8 amino acids via a Gly residue and a Ser residue.

The pVL1393-F2G6sec2-derived recombinant virus can secrete and produce a polypeptide in which a presumed catalytic region of G6 polypeptide (isoleucine at position 39 to isoleucine at position 378 in SEQ ID NO:1) is fused to the C-terminal of a FLAG peptide containing 8 amino acids via a Gly residue and a Ser residue.

About $2\times10^7$ Sf21 cells were suspended in 15 ml of EX-CELL 400 medium, put into a 75 cm$^2$ flask (manufactured by Greiner) and allowed to stand at room temperature for 30 minutes to adhesion the cells onto the flask, the supernatant was discarded, and 5 ml of EX-CELL 400 medium and 1 ml of the recombinant virus solution obtained in the above (5) were added to the flask.

After the addition, the cells and virus particles were thoroughly contacted by gently shaking at room temperature for 1 hour, and then cultured at 27° C. for 4 days by adding 10 ml of the TNM-FH insect medium. The culture supernatant was obtained respectively at 15 ml by centrifuging the culture at 1,500×g for 10 minutes.

Sodium azide, sodium chloride and calcium chloride were added to 15 ml of the culture supernatant obtained in the above to give final concentrations of 0.1%, 150 mmol/l and 2 mmol/l, respectively, and 100 µl of Anti-FLAG M1 Affinity Gel (manufactured by COSMO BIO) was added thereto, followed by gently stirring at 4° C. overnight.

After the stirring, the Anti-FLAG M1 Affinity Gel was recovered by centrifuging at 160×g for 10 minutes, and the gel was washed twice with 1 ml of a buffer solution containing 50 mmol/l Tris-HCl (pH 7.4), 150 mmol/l sodium chloride and 1 mmol/l calcium chloride.

After the washing, the gel was treated at 4° C. for 30 minutes by adding 30 µl of a buffer solution containing 50 mmol/l Tris-HCl (pH 7.4), 150 mmol/l sodium chloride and 2 mmol/l EDTA to elute proteins absorbed onto the gel. Thereafter, a supernatant was obtained by centrifuging at 160×g for 10 minutes.

To the gel, 30 µl of the buffer solution containing 50 mmol/l Tris-HCl (pH 7.4), 150 mmol/l sodium chloride and 2 mmol/l EDTA was added again, and the mixture was treated at 4° C. for 10 minutes and centrifuged at 160×g for 10 minutes to obtain a supernatant. Thereafter, by carrying out this process again, a total of three elution processes were carried out and a total of 85 µl of the eluate was obtained.

To the eluate was added 1 mol/l calcium chloride to give a final concentration of 4 mmol/l.

After carrying out SDS-PAGE using 8 µl of the eluate prepared in this manner, silver staining or Western blotting using an anti-FLAG antibody was carried. The silver staining was carried out using Silver Staining Kit Wako (manufactured by Wako Pure Chemical Industries). The method followed the manufacture's instructions of the kit. The Western blotting using an anti-FLAG antibody was carried out by using YEAST AMINO-TERMINAL FLAG EXPRESSION KIT (manufactured by SIGMA). The method followed the manufacture's instructions of the kit.

Results of the silver staining or Western blotting using an anti-FLAG antibody are shown in FIG. 3. FIG. 3A is a graph showing a result of the silver staining carried out after purifying a secreted FLAG peptide-fused G6 polypeptide (G6sec1 or G6sec2) (lanes 3 and 5) from a culture supernatant (lanes 4 and 6) of Sf21 cell infected with a recombinant virus derived from a secreted FLAG peptide-fused G6 polypeptide expression plasmid [pVL1393-F2G6sec1 (lanes 3 and 4) or pVL1393-F2G6sec2 (lanes 5 and 6)] using Anti-FLAG M1 Affinity Gel and subsequently subjecting it to SDS polyacrylamide gel electrophoresis. As a control, a sample (lane 1) was prepared in the same manner from a culture supernatant (lane 2) of Sf21 cell infected with a recombinant virus derived from plasmid pVL1393. Each arrow indicates position and size of the produced secreted G6 polypeptide.

Figure 3B:
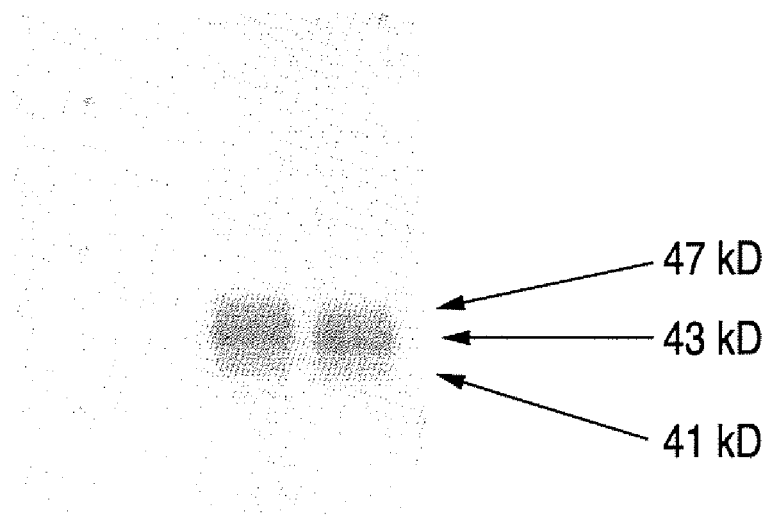

FIG. 3B is a graph showing a result of Western blotting carried out using an anti-FLAG peptide antibody after purifying a secreted FLAG peptide-fused G6 polypeptide (G6sec1 or G6sec2) from a culture supernatant of Sf21 cell infected with a recombinant virus derived from a secreted FLAG peptide-fused G6 expression plasmid [pVL1393-F2G6sec1 (lane 2) or pVL1393-F2G6sec2 (lane 3)] using Anti-FLAG M1 Affinity Gel and subsequently subjecting it to SDS polyacrylamide gel electrophoresis. As a control, a sample (lane 1) was prepared in the same manner from a culture supernatant of Sf21 cell infected with a recombinant virus derived from plasmid pVL1393. Each arrow indicates position and size of the produced secreted G6 polypeptide.

As a result, a broad band of approximately from 41 to 47 kD was found when an elution solution prepared from a culture supernatant of Sf21 infected with the pVL1393-F2G6sec1-derived recombinant virus was used. The size of the main band was about 43 kD. The molecular weight of the polypeptide calculated from its amino acid sequence is 40.95 kD, because it is considered that the recombinant virus can secrete and produce a polypeptide in which a presumed catalytic region of G6 polypeptide (aspartic acid at position 36 to isoleucine at position 378 in SEQ ID NO:1) is fused to the C-terminal of a FLAG peptide containing 8 amino acids via a Gly residue and a Ser residue. The reason for the larger molecular weight of the detected band than the calculated value is considered to be due to addition of sugar chains. The polypeptide has 4 possible N-linked sugar chain addition sites. The broad band indicates the presence of polypeptides having different numbers and sizes of added sugar chains.

A broad band of approximately 41 to 47 kD was also found when an elution solution prepared from a culture supernatant of Sf21 infected with the pVL1393-F2G6sec2-derived recombinant virus was used. The size of the main band was about 43 kD. The molecular weight of the polypeptide calculated from its amino acid sequence is 40.6 kD, because it is considered that the recombinant virus can secrete and produce a polypeptide in which a presumed catalytic region of G6 polypeptide (isoleucine at position 39 to isoleucine at position 378 in SEQ ID NO:1) is fused to the C-terminal of a FLAG peptide containing 8 amino acids via a Gly residue and a Ser residue. The reason for the larger molecular weight of the detected band than the calculated value is considered to be due to addition of sugar chains. The polypeptide has 4 possible N-linked sugar chain addition sites. The broad band indicates the presence of polypeptides having different numbers and sizes of added sugar chains.

On the other hand, the band was not detected when an elution solution prepared from a culture supernatant of Sf21 infected with the recombinant virus derived from the vector pVL1393.

Regarding the strength of bands detected by the Western blotting using anti-FLAG antibody, when the strength of the band detected in the elution solution prepared from the recombinant virus derived from pVL1393-F2G6sec1 is defined as 1, the strength of the band detected in the elution solution prepared from the recombinant virus derived from pVL1393-F2G6sec2 was 1.05.

Based on the above results, it was shown that FLAG peptide-fused G6 polypeptide can be secreted and produced using insect cells and that the polypeptide can be easily purified using Anti-FLAG M1 Affinity Gel.

EXAMPLE 9

Activity Measurement Using Flag Peptide-fused G6 Polypeptide Produced by Insect Cells:

β1,3-N-Acetylglucosaminyltransferase activity of the FLAG peptide-fused G6 polypeptide produced and purified in Example 8 was measured by using various substrates.

(1) Activity Measurement using 2-aminobenzene Modified Oligosaccharides as the Substrates β1,3-N-Acetylglucosaminyltransferase activity of the FLAG peptide-fused G6 polypeptide secreted and produced in insect cells was measured by using the eluate prepared in Example 8(6). The method of Example 7 was used for the activity measurement.

As substrates, oligosaccharides [LNnT, Galβ1-4GlcNAcβ1-3Galβ1-4GlcNAc (hereinafter referred to as "2LN"), Galβ1-4GlcNAcβ1-3Galβ1-4GlcNAcβ1-3Galβ1-4GlcNAc (hereinafter referred to as "3LN"), Galβ1-4GlcNAcβ1-3Galβ1-4GlcNAcβ1-3Galβ1-4GlcNAcβ1-3Galβ1-4GlcNAc (hereinafter referred to as "4LN"), Galβ1-4GlcNAcβ1-3Galβ1-4GlcNAcβ-3Galβ1-4GlcNAcβ1-3Galβ1-4GlcNAcβ1-3Galβ1-4GlcNAc (hereinafter referred to as "5LN"), or Galβ1-4(SO$_3$-6)GlcNAcβ1-3Galβ1-4(SO$_3$-6)GlcNAc (hereinafter referred to as "L2L2")] were labeled with 2-aminobenzamide and used. 2-Aminobenzamide-labeling of oligosaccharides was carried out using SIGMA 2AB glycan labeling kit (manufactured by Oxford Glycoscience) according to the manufacture's instructions of the kit. LNnT was purchased from Oxford Glycosystems. Other oligosaccharides were obtained from Seikagaku Corporation.

Specifically, the reaction was carried out at 37° C. for 16 hours in 20 µl of an assay solution [150 mmol/l sodium cacodylate (pH 7.2), 50 mmol/l UDP-GlcNAc (manufactured by SIGMA), 0.4% Triton CF-54, 10 mmol/l MnCl$_2$, 5 µmol/l 2-aminobenzamide-labeled sugar chain substrate, the above purified enzyme solution], and then the product was detected by high performance liquid chromatography (HPLC, details will be described below). As the enzyme, an eluate (1.5 µl) prepared from a culture supernatant of Sf21 infected with the recombinant virus derived from pVL1393-F2G6sec1 or an eluate (1.4 µl) prepared from a culture supernatant of Sf21 infected with the recombinant virus derived from pVL1393-F2G6sec2, prepared in Example 8(6), was used.

The assay solution after completion of the reaction was treated at 100° C. for 5 minutes and then mixed with 50 µl of pure water for HPLC and centrifuged at 10,000×g for 5 minutes to obtain the supernatant. To a tube containing the assay solution, 50 µl of pure water for HPLC was added again, the tube was washed, and supernatant was obtained by centrifugation at 10,000×g for 5 minutes and was combined with the first supernatant. Next, the supernatant was passed through Ultrafree-MC column (manufactured by Millipore) and a portion thereof (10 µl) was subjected to HPLC. The Ultrafree-MC column was used according to the method described in the manufacture's instructions attached thereto.

The HPLC was carried out using TSK-gel ODS-80Ts Column (4.6×300 mm; manufactured by TOSOH) as a column and 0.02 mol/l ammonium acetate buffer containing 7% methanol (pH 4.0) as an eluant at an elution temperature of 50° C. and a flow rate of 1 ml/min.

The product was detected using a fluorescence spectrophotometer FP-920 (manufactured by JASCO Corporation) (excitation wavelength: 330 nm, radiation wavelength: 420 nm).

As a result that the activity measurement was carried out on a secretory enzyme produced and purified using the pVL1393-F2G6sec1-derived recombinant virus (called G6sec1) and another secretory enzyme produced and purified using the pVL1393-F2G6sec2-derived recombinant virus (called G6sec2), both showed the β1,3-N-acetylglucosaminyltransferase activity. When G6sec1 and G6sec2, respectively, were used, the conversion efficiencies of the substrate LNnT into the product were 9.85% and 11.2%, respectively. A result of the examination of substrate specificity using G6sec1 or G6sec2 is shown in Table 1 (Test 1 in Table 1). Relative activities when the activity measured using 2-aminobenzamide-labeled LNnT as the substrate is defined as 100% are shown in the table. On the other hand, the activity was not detected in a sample prepared using the pVL1393-derived recombinant virus (control virus).

Also, a purified enzyme (G6sec2) was again prepared using the method shown in Example 8(6), its substrate specificity was again examined, and the results are also shown in Table 1 (Test 2 in Table 1). The purified enzyme (280 µl) was prepared from 30 ml of a culture supernatant of Sf21 infected with the recombinant virus derived from pVL1393-F2G6sec2, and the assay was carried out using a 4 µl portion thereof. Relative activities when the activity measured using 2-aminobenzamide-labeled LNnT as the substrate is defined as 100% are shown in the table. When LNnT was used as the substrate, the conversion efficiency into the product was 26.2%.

TABLE 1

Substrate specificity of
β1,3-N-acetylglucosaminyltransferase (G6)
using 2-aminobenzamide-labeled oligosaccharides
as substrates

| Substrate name | Relative activity (%) | | |
|---|---|---|---|
| | Test 1 | | Test 2 |
| | G6sec1 | G6sec2 | G6sec2 |
| LNnT | 100 | 100 | 100 |
| 2LN | 81.4 | 86.8 | 65.3 |
| 3LN | 92.9 | 95.8 | 79.2 |
| 4LN | 13.2 | 21.5 | 10.0 |
| 5LN | 9.3 | 11.5 | 12.3 |
| L2L2 | | | 5.9 |

As a result, it was found that poly-N-acetyllactosamine sugar chains (2LN, 3LN, 4LN and 5LN) also become substrates of the G6 polypeptide. It was also found that the shorter poly-N-acetyllactosamine sugar chains (2LN and 3LN) are apt to become substrates of the G6 polypeptide in comparison with the longer poly-N-acetyllactosamine sugar chains (4LN and 5LN). Furthermore, it was found that L2L2 which is a sulfated poly-N-acetyllactosamine sugar chain also becomes a substrate of the G6 polypeptide.

The β1,3-N-acetylglucosaminyltransferase was also detected when the G6sec1- or G6sec2-adsorbed ANTI-FLAG M1 AFFINITY GEL (gel before elution of the enzyme) was used as an enzyme. An amount of the gel equivalent to the elution solution used in the above β1,3-N-acetylglucosaminyltransferase activity measurement was used as the enzyme. When G6sec1-adsorbed gel and G6sec1-adsorbed gel were used, the conversion efficiencies of LNnT used as the substrate were 6.64% and 20.2%, respectively.

This result indicates that sugar chains can be synthesized even when the enzyme is adsorbed to the gel. On the other hand, the activity was not detected in the gel prepared in the same manner using the pVL1393-derived recombinant virus (control virus).

On the other hand, the G6sec1 and G6sec2 did not show the GlcNAc β1,3-galactosyltransferase activity. The β1,3-galactosyltransferase activity measurement was carried out according to a conventional method [*J. Biol. Chem.*, 274, 12499-12507 (1999)]. The reaction was carried out at 37° C. for 16 hours in 20 µl of an assay solution [14 mmol/l HEPES (pH 7.4), 75 µmol/l UDP-Gal (manufactured by SIGMA), 11 mmol/l MnCl$_2$, 88 µmol/l sugar chain substrate, the above purified enzyme]. The amount of the enzyme used was the same as the amount used in the measurement of β1,3-N-acetylglucosaminyltransferase. As a substrate, 2-aminobenzamide-labeled GlcNAcβ1-3Galβ1-4GlcNAcβ1-3Galβ1-4GlcNAc (hereinafter referred to as "GlcNAc-2LN") was used. The sugar chain was prepared by treating 2-aminobenzamide-labeled LN3 with β-galactosidase and thereby removing the terminal galactose residue. Specifically, 100 milli-units of β-galactosidase (manufactured by Seikagaku Corporation) were added to about 60 nmol of 2-aminobenzamide-labeled LN3, the reaction was carried out at 37° C. for 16 hours, and the sugar chain was prepared by inactivating β-galactosidase through its heat treatment at 100° C. for 5 minutes.

It was shown by the above results that the FLAG peptide-fused G6 polypeptide (G6sec1 or G6sec2) secreted and expressed in insect cells has the β1,3-N-acetylglucosaminyltransferase activity but does not have the β1,3-galactosyltransferase activity. From this result, it was confirmed again that the G6 polypeptide is not a β1,3-galactosyltransferase but a β1,3-N-acetylglucosaminyltransferase. It was shown that the β1,3-N-acetylglucosaminyltransferase G6 can be secreted and produced in insect cells as a fusion protein with FLAG peptide, and the produced fusion protein can be easily purified using ANTI-FLAG M1 AFFINITY GEL. It was shown that the produced fusion protein can be used in synthesizing sugar chains such as a poly-N-acetyllactosamine sugar chain.

It was found that the productivity of the enzyme is high when produced by insect cells in comparison with the case of producing it by Namalwa cells.

(2) Activity Measurement Using Pyridylaminated Oligosaccharides as Substrates

After carrying out the reaction at 37° C. for 14.5 hours in 30 µl of an assay solution [150 mmol/l sodium cacodylate (pH 7.2), 50 mmol/l UDP-GlcNAc (manufactured by SIGMA), 0.4% Triton CF-54, 10 mmol/l MnCl$_2$, 50 µmol/l pyridylaminated sugar chain substrate, a purified enzyme solution (G6sec2)], the product was detected by HPLC. The purified enzyme (G6sec2) was obtained according to the method shown in Example 8(6). The purified enzyme (280 µl) was prepared from 30 ml of a culture supernatant of Sf21 infected with the recombinant virus derived from pVL1393-F2G6sec2, and the assay was carried out using 5 µl thereof. As substrates, LnNT, lacto-N-tetraose (Galβ1-3GlcNAcβ1-3Galβ1-4Glc (hereinafter referred to as "LNT"), lacto-N-fucopentaose II (Galβ1-3(Fucα1-4)GlcNAcβ1-3Galβ1-4Glc; hereinafter referred to as "LNFP-II"), lacto-N-fucopentaose III (Galβ1-4(Fucα1-3)GlcNAcβ1-3Galβ1-4Glc; hereinafter referred to as "LNFP-III"), lacto-N-fucopentaose V (Galβ1-3GlcNAcβ1-3Galβ1-4(Fucα1-3)Glc; hereinafter referred to as "LNFP-V"), and lacto-N-difucohexaose II (Galβ1-3(Fucα1-4)GlcNAcβ1-3Galβ1-4(Fucα1-3)Glc; hereinafter referred to as "LNDFH-II") (all manufactured by Oxford Glycosystems) were fluorescently-labeled with aminopyridine and used. The substrates were fluorescently-labeled according to a conventional method [*Agric. Biol. Chem.*, 54, 2169 (1990)].

After carrying out the reaction on each substrate using an assay solution containing UDP-GlcNAc (saccharide donor) and an assay solution containing no donor and subsequently analyzing by HPLC, peaks appeared only in the assay solution containing UDP-GlcNAc were defined as products.

The assay solution after completion of the reaction was treated at 100° C. for 5 minutes and then centrifuged at 10,000×g for 5 minutes to obtain a supernatant, and a part thereof (5 µl) was subjected to HPLC.

The HPLC was carried out using TSK-gel ODS-80Ts Column (4.6×300 mm; manufactured by TOSOH) and 0.02 mol/l ammonium acetate buffer (pH 4.0) as the eluant at an elution temperature of 50° C. and a flow rate of 0.5 ml/min.

Detection and determination of products were carried out using a fluorescence spectrophotometer FP-920 (manufactured by JASCO Corporation) (excitation wavelength: 320 nm, radiation wavelength: 400 nm).

Relative activities when the activity measured using LnNT as a substrate is defined as 100% are shown in Table 2.

TABLE 2

Substrate specificity of
β1,3-N-acetylglucosaminyltransferase (G6) using
pyridylaminated oligosaccharides as substrates

| Substrate name | Relative activity (%) |
|---|---|
| LNnT | 100 |
| LNT | 5.5 |
| LNFP-II | <0.05 |
| LNFP-III | 4.9 |
| LNDFH-II | <0.05 |
| LNFP-V | 4.9 |

When LNnT was used as a substrate, the conversion efficiency of the substrate into the product was 12.8%. It was found that LNnT becomes a good substrate of G6 polypeptide (G6sec2), but LNT, LNFP-III and LNFP-V hardly become substrates. Furthermore, it was also found that LNFP-II and LNDFH-II as oligosaccharides in which fucose is added via α1,4-linkage to the GlcNAc residue present at position 2 from the non-reducing terminal of LNT do not become substrates of the G6 polypeptide.

(3) Activity Measurement Using Unlabeled Oligosaccharides as Substrates

The glycosyltransferase reaction was carried out as follows. The reaction was carried out at 37° C. for 16 hours in 40 µl of an assay solution [50 mmol/l MOPS (pH 7.5), 5 mmol/l UDP-GlcNAc (manufactured by SIGMA), 5 mmol/l $MnCl_2$, 10 mmol/l sugar chain substrate, a purified enzyme solution (G6sec2)]. Next, the mixture was treated at 100° C. for 5 minutes and then centrifuged at 10,000×g for 20 minutes to obtain a supernatant, and a part thereof was analyzed using HPAE/PAD (High Performance Anion Pulsed Amperometric Detection; manufactured by DIONEX). The method was specifically carried out according to a conventional method [*Anal. Biochem.*, 189, 151-162 (1990), *J. Biol. Chem.*, 273, 433-440 (1998)].

As a purified enzyme (G6sec2), 10l of the enzyme obtained in the above (2) was used. As substrates, unlabeled oligosaccharides [lactose (Galβ1-4Glc) and LNnT] were used.

After the reaction on each substrate using an assay solution containing UDP-GlcNAc (saccharide donor) and an assay solution containing no donor, analysis was carried out using HPAE/PAD and peaks appeared only in the assay solution containing UDP-GlcNAc were defined as products. The product was identified using coincidence of its elution time with that of standard sugar chain as the index. As standard sugar chains, GlcNAcβ1-3Galβ1,4Glc and GlcNAcβ1-3Galβ1,4GlcNAcβ1-3Galβ1-4Glc were used.

When LNnT and lactose were used as substrates, the conversion efficiencies into the product were 0.48% and 0.30%, respectively. When the activity using LNnT as a substrate is defined as 100%, the relative activity when lactose is used as a substrate is calculated to be 62.5%. Based on the above results, it was found that the β1,3-N-acetylglucosaminyltransferase (G6) also uses lactose as a good substrate in addition to LNnT.

(4) Activity Measurement Using Glycolipids

Using glycolipids as the substrate, β1,3-N-acetylglucosaminyltransferase activity of the G6 polypeptide was measured according to known methods [*FEBS*, 462, 289 (1999), *J. Biol. Chem.*, 269, 14730-14737 (1994), *J. Biol. Chem.*, 267, 23507 (1992), *J. Biol. Chem.*, 267, 2994 (1992)]. Specifically, the reaction was carried out at 37° C. for 16 hours in 20 µl of a reaction solution [150 mmol/l sodium cacodylate (pH 7.2), 10 mmol/l UDP-GlcNAc (manufactured by SIGMA), 480 µmol/l UDP—[$^{14}$C]GlcNAc (manufactured by Amersham), 0.4% Triton CF-54, 10 mmol/l $MnCl_2$, 250 µl/l glycolipid, purified enzyme (G6sec2)]. As the purified enzyme (G6sec2), 10 µl of the enzyme obtained in the above (2) was used. As glycolipids, lactosylceramide, paragloboside, galactosylceramide (Type I) and galactosylceramide (Type II) were used. Paragloboside was obtained from Yasunori Kushi at Tokyo Medical and Dental University. Other glycolipids were purchased from SIGMA. After completion of the reaction, 200 µl of 0.1 mol/l KCl was added and lightly centrifuged to obtain the supernatant. The supernatant was passed through Sep-Pak plus C18 Cartridge (manufactured by Waters) which had been washed once with 10 ml of methanol and equilibrated by washing twice with 10 ml of 0.1 mol/l KCl to adsorb the glycolipid in the supernatant onto the cartridge. After washing the cartridge twice with 10 ml of pure water for HPLC, the adsorbed glycolipid was eluted with 5 ml of methanol. After concentrating the eluate to about 10 µl using a vacuum dryer, the concentrated solution was plotted on a TLC plate (HPTLC plate Silica gel 60: manufactured by MERCK) and developed using a developing solvent comprising a composition of chloroform:methanol:water (containing 0.2% $CaCl_2$)=65:35:8. After the development was carried out to a position 5 mm from the upper end of the TLC plate, the plate was dried and then the radioactivity incorporated into the glycolipid was measured using Bio Image Analyzer BAS 2000 (manufactured by Fuji Photo Film).

It was found that the FLAG-fused G6 polypeptide (G6sec2) uses lactosylceramide and paragloboside as substrates. When lactosylceramide and paragloboside were used as the substrates, the conversion efficiencies were 5.39% and 25.2%, respectively. When the G6 polypeptide activity using lactosylceramide as a substrate was defined as 100%, the activity when paragloboside was used as a substrate was 468%.

On the other hand, the G6 polypeptide (G6sec2) did not show activity for galactosylceramide (Type I) and galactosylceramide (Type II).

Based on the above results, it was found that the G6 polypeptide is a β1,3-N-acetylglucosaminyltransferase which uses lactosylceramide and paragloboside as good substrates. In comparison with the result of Example 7(2), it can be understood that paragloboside is more easily used as a substrate than lactosylceramide in secreted G6 (G6sec2). Although it has been shown that β3GnT as a known β1,3-N-acetylglucosaminyltransferase uses paragloboside as a substrate in vitro, its activity when lactosylceramide is used as a substrate is low [*Glycobiology*, 9, 1123 (1999)]. Accordingly, it is considered that the G6 polypeptide is a β1,3-N-acetylglucosaminyltransferase having different substrate specificity from that of β3GnT.

Furthermore, when the G6 polypeptide and GlcNAc β1,4-galactosyltransferase are used in combination, it is possible to synthesize, for example, paragloboside from lactosylceramide, neolactohexaosylceramide (Galβ1-4GlcNAcβ1-3Galβ1-4GlcNAcβ1-3Galβ1-4Glc-ceramide) from paragloboside or neolactohexaosylceramide from lactosylceramide.

EXAMPLE 10

Synthesis of Glycolipids in Human Culture Cells Transfected with a G6 Polypeptide Expression Plasmid:

Neutral glycolipids were extracted from Namalwa cells ($10^8$ cells) transfected with pAMo-G6 prepared in Example 6(1), Namalwa cells ($10^8$ cells) transfected with the vector pAMo and Namalwa cells transfected with no plasmid, and the compositions and expression levels of glycolipids having N-acetyllactosamine structure in the non-reducing termini of sugar chains were compared. The method was carried out according to known methods [Shujunsha, *Cell Technology Supplement (Saibo Kogaku Bessatsu)*, "Glycobiology Experiment Protocol (Glycobiology Jikken Protocol)", *Anal. Biochem.*, 223, 232 (1994)]. As antibodies, monoclonal antibodies capable of recognizing N-acetyllactosamine structure present in the non-reducing termini of sugar chains [anti-N-acetyllactosamine antibodies 1B2 to 1B7: *Arch. Biochem. Biophysics.*, 303, 125 (1993), *Infect. Immun.*, 64, 4129 (1996), *J. Comp. Neurol.*, 22, 607 (1988)] were used.

Neutral glycolipids corresponding to $10^7$ cells were spotted on a TLC plate (HPTLC plate Silica gel60: manufactured by MERCK) and developed using a developing solvent containing a composition of chloroform:methanol:water (containing 0.2% $CaCl_2$)=60:35:8. As standard glycolipids, glucosylceramide (2 µg; hereinafter referred sometimes to as "GlcCer"), lactosylceramide (2 µg; hereinafter referred sometimes to as "LacCer"), lactotriaosylceramide (0.5 µg; hereinafter referred sometimes to as "$Lc_3Cer$") and paragloboside (0.5 µg; hereinafter referred sometimes to as "$nLc_4Cer$") were spotted in the case of orcinol staining, and paragloboside ($nLc_4Cer$) and neolactohexaosylceramide (hereinafter referred sometimes to as "$nLc_6Cer$") in the case of immunostaining. Except for the standard glycolipids, two identical plates were prepared and one of them was used in orcinol staining, and another was used in immunostaining.

Each of the plates after development was soaked for 20 seconds in a solution containing a composition of isopropanol:water (containing 0.2% $CaCl_2$):methanol=40:20:7. Next, the plate was covered with a PVDF membrane (Immobilon: manufactured by Millipore) and a glass microfiber filter (manufactured by ATTO), and glycolipids on the plate were transferred to the PVDF membrane using TLC Thermal Blotter (manufactured by ATTO) at 180° C. and at level 8 for 45 seconds. The PVDF membrane was soaked for 1 hour in a solution which contains 5% skim milk and TBS-Tween 20 and then soaked for 2 hours in a solution which contains 5% skim milk and TBS-Tween 20 containing 1/100 volume of anti-N-acetyllactosamine antibodies 1B2 to 1B7 (hybridoma culture supernatants). The PVDF membrane was washed with TBS-Tween 20 three times and then soaked for 1 hour in a solution which contains 5% skim milk and TBS-Tween 20 containing a horseradish peroxidase-labeled anti-mouse IgM antibody (0.4 µg/ml: manufactured by Jackson). The PVDF membrane was washed three times with TBS-Tween 20, and then the antibody-bound glycolipids were detected using an ECL system (manufactured by Amersham Pharmacia).

Figure 4A:
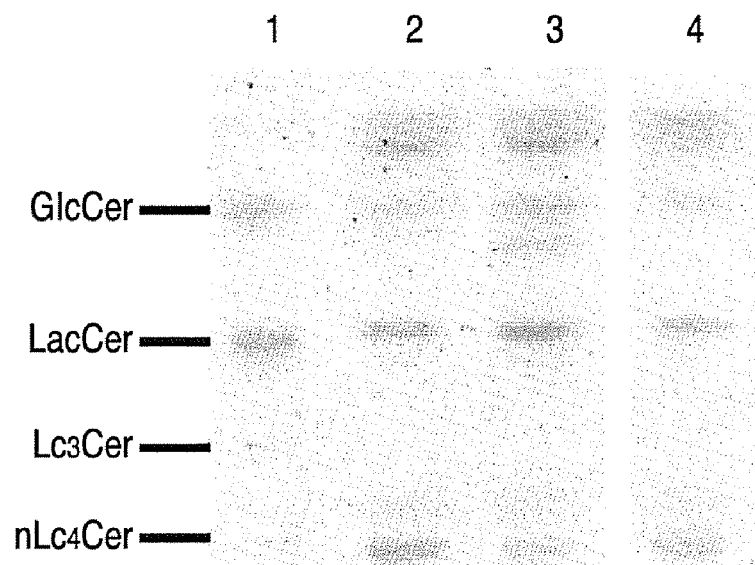
FIG. 4 shows a result of a test carried out by extracting neutral glycolipid from Namalwa cells transfected with a G6 polypeptide expression plasmid, developing the extract on a TLC plate and then subjecting it to orcinol staining. B shows a result of a test carried out by extracting neutral glycolipid from Namalwa cells transfected with a G6 polypeptide expression plasmid, developing the extract on a TLC plate and then subjecting it to immunostaining by using an anti-N-acetyllactosamine antibody 1B2.
Figure 4B:
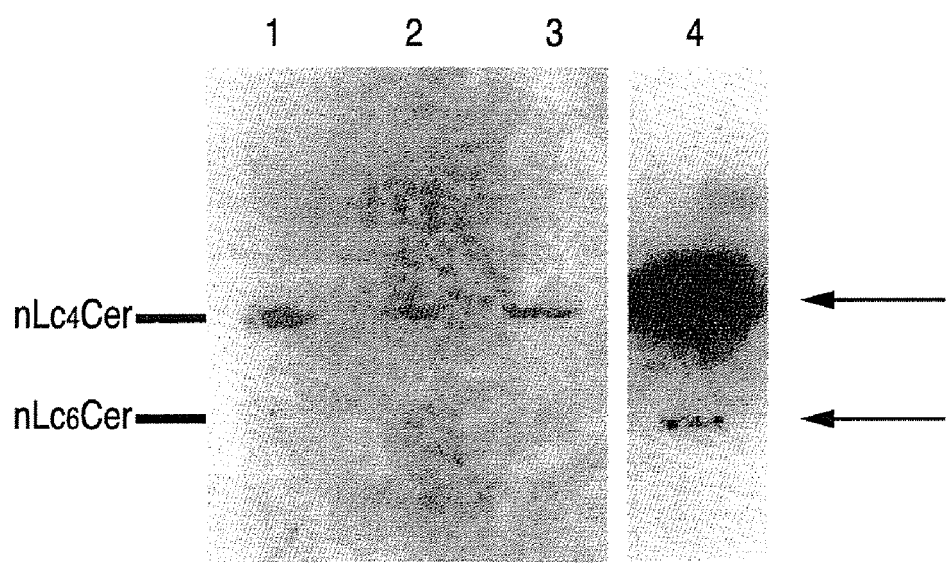

Results of the orcinol staining are shown in FIG. 4A, and results of the immunostaining in FIG. 4B. Lane 1 in FIG. 4A shows development of the standard glycolipids (GlcCer, LacCer, $Lc_3Cer$ and $nLc_4Cer$), and other lanes show results of the orcinol staining performed on neutral glycolipids extracted from Namalwa cells transfected with no plasmid (lane 2), Namalwa cells transfected with the vector pAMo (lane 3) and Namalwa cells transfected with pAMo-G6 (lane 4) and developed on the TLC plate. Lane 1 in FIG. 4B shows development of the standard glycolipids ($nLc_4Cer$ and $nLc_6Cer$), and other lanes show results of the immunostaining by using an antibody capable of recognizing N-acetyllactosamine structure present in the non-reducing termini of sugar chains (anti-N-acetyllactosamine antibodies 1B2) performed on neutral glycolipids extracted from Namalwa cells transfected with no plasmid (lane 2), Namalwa cells transfected with the vector pAMo (lane 3) and Namalwa cells transfected with pAMo-G6 (lane 4) and developed on the TLC plate. The arrows in B show positions of glycolipids ($nLc_4Cer$ and $nLc_6Cer$) whose expression was increased in the Namalwa cells transfected with pAMo-G6.

It was found that amounts of paragloboside ($nLc_4Cer$) and neolactohexaosylceramide (Galβ1-4GlcNAcβ1-3Galβ1-4GlcNAcβ1-3Galβ1-4Glc-ceramide: abbreviated as "$nLc_6Cer$" in the drawing), which were glycolipids having N-acetyllactosamine structure on the non-reducing termini of sugar chains, are increased in the Namalwa cells expressing G6 polypeptide, in comparison with the Namalwa cells transfected with the vector and the Namalwa cells transfected with no plasmid (FIG. 4B).

Based on the above results and the results of Example 9, it was found that the G6 polypeptide is involved in the synthesis of glycolipids having N-acetyllactosamine structure in cells. As shown in Example 9, the G6 polypeptide can synthesize lactotriaosylceramide (GlcNAcβ1-3Galβ1-4Glc-ceramide) by using lactosylceramide (Galβ1-4Glc-ceramide) as the substrate. It is considered that, in appropriate cells expressing a β1,4-galactosyltransferase (e.g., Namalwa cells), lactotriaosylceramide synthesized by the G6 polypeptide is converted into paragloboside (Galβ1-4GlcNAcβ1-3Galβ1-4Glc-ceramide) by the further addition of galactose via β1,4-linkage by the β1,4-galactosyltransferase. The above results indicate that a glycolipid in which N-acetyllactosamine is added via β1,3-linkage to the galactose residue present in the non-reducing terminal of a glycolipid sugar chain as a substrate can be synthesized by expressing the G6 polypeptide in appropriate cells which express glycolipid substrates of the G6 polypeptide such as lactosylceramide and paragloboside. In addition, it is indicated that a glycolipid in which N-acetyllactosamine structure or a poly-N-acetyllactosamine sugar chain is added to the non-reducing terminal of a sugar chain on a glycolipid substrate can be synthesized when a cell expresses an appropriate β1,4-galactosyltransferase.

The above results show that the G6 polypeptide acts as a lactosylceramide β1,3-N-acetylglucosaminyltransferase in cells and is involved in the synthesis of neolacto-series glycolipids and lacto-series glycolipids. Furthermore, it is considered that the G6 polypeptide is also involved in the synthesis of a glycolipid having a poly-N-acetyllactosamine sugar chain, such as neolactohexaosylceramide, in cells by acting with a GlcNAc β1,4-galactosyltransferase synergistically.

Although it has been shown that a known enzyme (β3GnT) shows weak β1,3-N-acetylglucosaminyltransferase activity on lactosylceramide in vitro, it has not been shown whether or not it can actually use lactosylceramide as a substrate in cells.

EXAMPLE 11

Examination of Expression Level of Transcripts of the G6 Gene in Various Cells

Transcripts of the G6 gene were quantified by quantitative PCR according to conventional methods [*Proc. Natl. Acad. Sci. USA*, 87, 2725 (1990), *J. Biol. Chem.*, 269, 14730 (1994), Japanese Published Unexamined Patent Application No. 181759/94].

Quantification of β-actin transcripts for correcting the expression level of the gene was also performed in the same manner by quantitative PCR.

(1) Synthesis of Single-stranded cDNAs Derived from Various Cells and Cell Lines As cell lines, colon cancer cell lines (Colo201, Colo205, HCT-15, SW480, SW620, WiDR, LS180), lung cancer cell lines (AOI, EBC-1, PC-1, A549, ABC-1, EHHA-9, HAL8, HAL24, LX-1, PC-7, PC-9, PC-12, RERF-LC-MS), stomach cancer cell lines (KATOIII, MKN1, MKN7, MKN28, MKN45, MKN74, TMK1, HSC43), neuroblastoma cell lines (NAGAI, NB-9, SCCH-26, IMR-32, SK-N-SH), glioblastoma cell lines (A172, KG-1-C, YKG-1, T98G, U251, U-118-MG, G1-1), pancreatic cancer cell lines (Capan-1, Capan-2), a prostatic cancer cell line PC-3, a hepatic cancer cell line HepG2, an erythroleukemia cell line K562, granulocyte/monocyte cell lines (HL-60, U-937, U266), a T-cell line Jurkat and B-cell lines (Namalwa KJM-1, Namalwa, Daudi, Ramos, NALL-1, Raji) were used. Jurkat was obtained from Aichi Cancer Center. KATOIII and PC-9 were obtained from I B L Co., Ltd. Other cells can be obtained from Japanese Collection of Research Bioresources (JCRB) cell bank (internet address, http://cellbank.nihs.go.jp/) or American Type Culture Collection.

Furthermore, polymorphonuclear leukocytes and mononuclear leukocytes were separated and isolated from peripheral blood of a health adult using Polymorphprep™ as a kit manufactured by Nycomed Pharma. The thus obtained mononuclear leukocytes were further separated into monocytes and lymphocytes according to a conventional method [*J. Immunol.*, 130, 706 (1977)].

A total RNA of each cell was prepared according to a conventional method [*Biochemistry*, 18, 5294 (1977)]. Single-stranded cDNAs from total RNAs were synthesized using a kit (SUPER™ Preamplification System: manufactured by BRL). Single-stranded cDNAs were synthesized from 5 μg of total RNAs in the case of cell lines, or from 1 μg of total RNAs in the case of peripheral blood-derived leukocytes, and diluted with water 50-folds and 10-folds, respectively, and used as templates of PCR. Oligo(dT) primers were used as primers.

(2) Synthesis of Single-stranded cDNAs Derived from Various Human Tissues

Single-stranded cDNAs were synthesized from mRNAs of various human organs (manufactured by Clontech) in the same manner as in the above (1). Single-stranded cDNAs were synthesized from 1 μg of mRNAs, diluted 240-folds and used as templates of PCR. Oligo(dT) primers were used as primers. As mRNAs, mRNAs derived from the following 35 organs were used: 1. adrenal gland, 2. brain, 3. caudate nucleus, 4. hippocampus, 5. substantia nigra, 6. thalamus, 7. kidney, 8. pancreas, 9. pituitary gland, 10. small intestine, 11. bone marrow, 12. amygdala, 13. cerebellum, 14. corpus callosum, 15. fetal brain, 16. fetal kidney, 17. fetal liver, 18. fetal lung, 19. heart, 20. liver, 21. lung, 22. lymph node, 23. mammary gland, 24. placenta, 25. prostate, 26. salivary gland, 27. skeletal muscle, 28. spinal cord, 29. spleen, 30. stomach, 31. testis, 32. thymus, 33. thyroid, 34. trachea and 35. uterus.

Furthermore, a total RNA was prepared from the human colon tissue, and a single-stranded cDNA was synthesized using 5 μg of the total RNA in the same manner as in the case of the above cell lines of (1).

(3) Preparation of Standard and Internal Control for Quantitative PCR

Standard and internal control were constructed using the pBS-G6 constructed in Example 3(5) [cf. the following (a) and (b)].

β-Actin transcripts were determined in the same manner as described in reports [*J. Biol. Chem.*, 269, 14730 (1994), Japanese Published Unexamined Patent Application No. 181759/94]. In determining β-actin transcripts, pUC119-ACT and pUC119-ACTd were converted into linear DNAs by digesting with restriction enzymes (HindIII and Asp718) which cut out cDNA moieties and then used as a standard and internal control, respectively [*J. Biol. Chem.*, 269, 14730 (1994), Japanese Published Unexamined Patent Application No. 181759/94]. After confirming that each plasmid was completely digested, they were used by serially diluting with water containing 1 μg/ml of yeast transfer RNAs.

(a) Preparation of a Standard for G6 Transcripts Determination pBS-G6 constructed in Example 3(5) was converted into a linear DNA by digestion with a restriction enzyme (EcoRI) which cuts out the G6 cDNA moiety and used as a standard for determination. After confirming that the plasmid was completely digested, it was used by serially diluting with water containing 1 μg/ml of yeast transfer RNAs.

(b) Preparation of Internal Control for G6 Transcripts Determination pBS-G6 was digested with restriction enzymes MscI and BglII and the linear DNAs were subjected to self-ligation to construct pBS-G6d in which 243 bp were deleted from the G6 cDNA. The pBS-G6d was converted into a linear DNA by digestion with a restriction enzyme (EcoRI) which cuts out the G6 cDNA moiety and used as the internal control for determination. After confirming that the plasmid was completely digested, it was used by serially diluting with water containing 1 μg/ml of yeast transfer RNAs.

(4) Determination of Transcripts of the G6 Gene Using Quantitative PCR

Competitive-PCR as a quantitative PCR was carried out using the single-stranded cDNAs derived from cell lines and normal tissues prepared in the above (1) and (2). As the primers for PCR, CB513 having the nucleotide sequence represented by SEQ ID NO:25 and CB515 having the nucleotide sequence represented by SEQ ID NO:28 were used for the detection of G6 transcripts. For the detection of β-actin transcripts, CB53 having the nucleotide sequence represented by SEQ ID NO:29 and CB54 having the nucleotide sequence represented by SEQ ID NO:30 were used. Also, a calibration curve was prepared by carrying out the PCR in the same manner using the standard and internal control prepared in (3).

PCR was carried out by adding a DNA polymerase AmpliTaq Gold™ (manufactured by Perkin Elmer) to 50 μl of a reaction solution [10 mmol/l Tris-HCl (pH 8.3), 50 mmol/l KCl, 1.5 mmol/l $MgCl_2$, 0.2 mmol/l dNTP, 0.001% (w/v) gelatin, 0.2 μmol/l KCl gene specific primers] containing 10 μl of the above single-stranded cDNAs and 10 μl (1 fg) of the internal control plasmid. The amount of the internal control plasmid or the amount of the standard plasmid was appropriately changed depending on each tissue or cell.

PCR was carried out under the following conditions.

In quantification of G6 transcripts, heating was carried out at 95° C. for 11 minutes, and 42 cycles were carried out, each cycle consisting of a reaction at 95° C. for 30 seconds, at 65° C. for 1 minute and at 72° C. for 2 minutes.

In quantification of the β-actin transcripts, heating was carried out at 95° C. for 11 minutes, and 24 cycles were carried out, each cycle consisting of a reaction at 95° C. for 1 minute, at 65° C. for 1 minute and at 72° C. for 2 minutes.

A solution of 10 μl after the PCR was subjected to electrophoresis using 1% agarose gel, and the gel was stained with ethidium bromide and photographed. Staining intensity of the amplified fragment was measured by scanning the photograph using NIH Image System, and used as the amount of amplification. In order to carry out more accurate quantification of transcripts, similar PCR was carried out by changing the number of cycles of the PCR. The amounts of the standard and internal control were changed depending on the number of cycles of the PCR.

Using 0.125 fg, 0.25 fg, 0.5 fg, 1 fg, 2 fg or 4 fg of the standard prepared in the above (3) instead of the cell-derived single-stranded cDNAs, PCR was carried out and the amounts of amplified fragments were measured, and a calibration curve was prepared by plotting the amount of cDNA against the amount of the amplified fragment.

Figure 5:
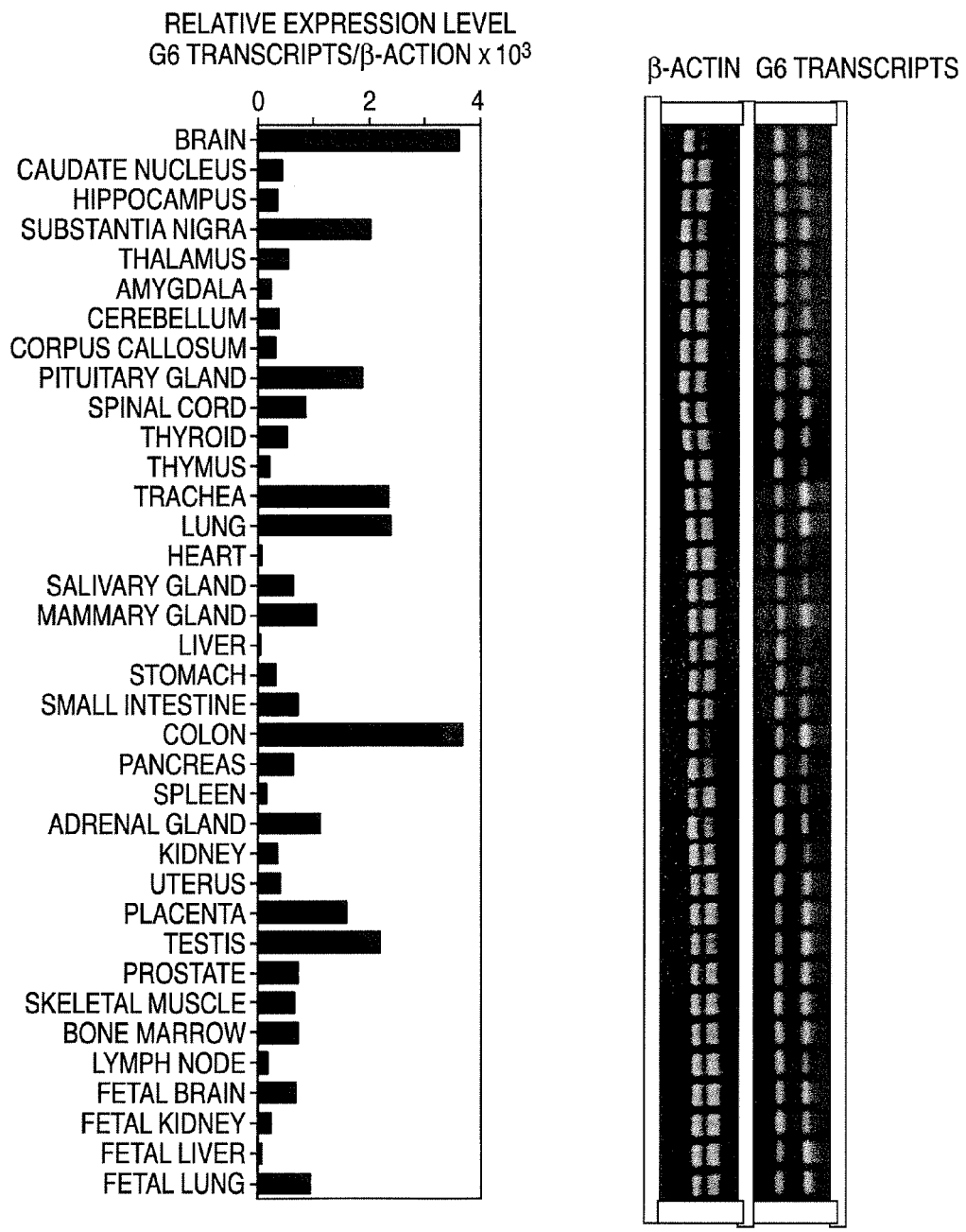
FIG. 5 shows a result of electrophoresis to examine the expression levels of G6 transcripts and β-actin transcripts in 36 human organs by using competitive PCR. The histogram is a graph showing the expression level of G6 transcripts when the expression level of β-actin is defined as 1,000.

When the above primers for quantification of G6 transcripts are used, a DNA fragment of 458 bp is amplified from G6 transcripts and the G6 standard, and a DNA fragment of 215 bp is amplified from the G6 internal control (photograph in FIG. 5).

When the above primers for quantification of β-actin transcripts are used, a DNA fragment of 649 bp is amplified from β-actin transcripts and the β-actin standard, and a DNA fragment of 439 bp is amplified from the β-actin internal control (photograph in FIG. 5).

The amounts of G6 transcripts are shown in the histogram of FIG. 5, Table 3-1 and Table 3-2, which are indicated as relative values when the amount of β-actin transcripts is defined as 1,000.

TABLE 3-1

Expression level of G6 transcripts in various cell lines

| Cell lines | Cell type | G6 transcripts/ β-actin transcripts (×1,000) |
|---|---|---|
| Colo201 | colon adenocarcinoma | 0.43 |
| Colo205 | colon adenocarcinoma | 3.08 |
| HCT15 | colon adenocarcinoma | 0.43 |
| SW480 | colon adenocarcinoma | 0.36 |
| SW620 | colon adenocarcinoma | 0.50 |
| WiDr | colon adenocarcinoma | 0.79 |
| LS180 | colon adenocarcinoma | 0.27 |
| AOI | lung squamous cell carcinoma | 0.24 |
| EBC-1 | lung squamous cell carcinoma | 1.04 |
| PC-1 | lung squamous cell carcinoma | 0.57 |
| A545 | lung adenocarcinoma | 0.14 |
| ABC-1 | lung adenocarcinoma | 0.18 |
| EHHA-9 | lung adenocarcinoma | 0.17 |
| HAL8 | lung adenocarcinoma | 2.51 |
| HAL24 | lung adenocarcinoma | 0.41 |
| LX-1 | lung adenocarcinoma | 2.07 |
| PC-7 | lung adenocarcinoma | 7.24 |
| PC-9 | lung adenocarcinoma | 0.44 |
| PC-12 | lung adenocarcinoma | 0.57 |
| RERF-LC-MS | lung adenocarcinoma | 3.62 |
| KATOIII | stomach cancer | 3.37 |
| MKN1 | stomach cancer | 0.35 |
| MKN7 | stomach cancer | 1.29 |
| MKN28 | stomach cancer | 4.84 |
| MKN45 | stomach cancer | 0.12 |
| MKN74 | stomach cancer | 2.62 |
| TMK1 | stomach cancer | 0.16 |
| HSC43 | stomach cancer | 1.06 |

TABLE 3-2

Expression level of G6 transcripts in various cell lines

| Cell lines | Cell type | G6 transcripts/ β-actin transcripts (×1,000) |
|---|---|---|
| NAGAI | neuroblastoma | 0.07 |
| NB-9 | neuroblastoma | 1.74 |
| SCCH-26 | neuroblastoma | 1.71 |
| IRM32 | neuroblastoma | 1.63 |
| SK-N-SH | glioblastoma | 1.20 |
| A172 | glioblastoma | 0.71 |
| KG-1-C | glioblastoma | 0.04 |
| YKG-1 | glioblastoma | 0.42 |
| T98G | glioblastoma | 0.30 |
| U251 | glioblastoma | 1.38 |
| U-118-MG | glioblastoma | 0.51 |
| G1-1 | glioblastoma | 0.12 |
| Capan-1 | pancreas adenocarcinoma | 1.51 |
| Capan-2 | pancreas adenocarcinoma | 0.19 |
| PC-3 | prostate adenocarcinoma | 0.86 |
| HepG2 | hepatocellular carcinoma | 0.00 |
| K562 | clonic myelogenous leukemia | 0.06 |
| U-937 | histiocytic lymphoma | 0.55 |
| HL-60 | promyelocytic leukemia | 0.91 |
| Namalwa | Burkitt's lymphoma | 0.04 |
| Namalwa KJM-1 | Burkitt's lymphoma | 0.38 |
| Daudi | Burkitt's lymphoma | 0.00 |
| Raji | Burkitt's lymphoma | 0.02 |
| Ramos | Burkitt's lymphoma | 0.01 |
| U266 | myeloma | 0.03 |
| Jurkat | acute T cell leukemia | 0.05 |
| NALL-1 | lymphoblastic leukemia | 1.06 |

G6 transcripts were expressed in almost all of the 36 human tissues examined (FIG. 5). Expression level varied among tissues, and it was expressed relatively frequently in the cerebellum, pituitary gland, trachea, lung, colon, placenta, testis and the like tissues. Furthermore, G6 transcripts were expressed also in monocytes and lymphocytes separated from human peripheral blood.

Regarding cell lines, it was expressed relatively frequently in a colon cancer cell line Colo205, lung cancer cell lines (EBC-1, HAL8, LX-1, PC-7, RERF-LC-MS), stomach cancer cell lines (KATOIII, MKN7, MKN28, MKN74, HSC43), neuroblastoma cell lines (NB-9, SCCH-26, IMR-32, SK-N-SH), a glioblastoma cell line (U251), a pancreatic cancer cell line (Capan-1) and a B-cell line (NALL-1) (Table 3-1, Table 3-2).

EXAMPLE 12

Structural Analysis of Chromosomal Gene Encoding G6 Polypeptide:

Currently, sequences of a large number of human chromosomal genes whose functions are unknown are registered in data bases. Thus, by comparing the sequence of G6 cDNA of the present invention with sequences of the human chromosomal genes registered in data bases, there is a possibility to identify a human chromosomal gene encoding the G6 polypeptide of the present invention (called G6 chromosomal gene) and to reveal its structure. When a chromosomal gene sequence which is identical to the sequence of the G6 cDNA is registered, a promoter region and exon and intron structure of the chromosomal gene encoding the polypeptide of the present invention can be determined by comparing sequence of the cDNA and sequence of the chromosomal gene.

When the nucleotide sequence of human G6 cDNA (SEQ ID NO:2) was compared with the sequences registered in GenBank [accessible from the home page (http://www.ncbi.nlm.nih.gov/) of National Center for Biotechnology Information (NCBI) on internet], it was found that a part of the human chromosomal working draft sequence (131,716 bp) of registration No. AC025833 (published on May 30, 2000) (an assembly sequence comprising a sequence of positions 67,758 to 72,176: shown in SEQ ID NO:30) is identical to the nucleotide sequence of G6 cDNA. As a result of the analysis, nucleotides of positions 1 to 3,721 in the G6 cDNA sequence having the nucleotide sequence represented by SEQ ID NO:2 is identical to nucleotides of positions 653 to 4,373 in SEQ ID NO:30. Thus, it was found that the G6 cDNA moiety shown in SEQ ID NO:2 is derived from one exon. It was considered that the sequence of AATAAA present in positions 3,702 to 3707 in the G6 cDNA sequence represented by SEQ ID NO:2 is a polyadenylation signal. It was considered that an upstream sequence (654 bp) of the exon is a promoter region (including transcription controlling region) of the G6 chromosomal gene. When the presence of consensus sequences in binding sequences of transcription factors was analyzed on the promoter region (654 bp) by using Motif Search Program of a sequence analyzing software GENE-TYX-MAC 10.1 which was prepared based on Transcription Factor Database [*Nucleic Acids Research,* 18, 1749 (1990), *Trends in Biochemical Science,* 16, 455 (1991), *Nucleic Acids Research,* 20S, 2091 (1992), *Nucleic Acids Research,* 21S, 3117 (1993)], it was judged that the sequence has the promoter region.

Since the sequence of registration No. AC025833 is derived from the human first chromosome, it was found that the G6 chromosomal gene is positioned at the human first chromosome. The position of the G6 chromosomal gene on the chromosome and its structure (promoter region and exon region) were able to be specified for the first time by the present invention through the elucidation of the structure of the G6 cDNA and function of the polypeptide encoded thereby. Furthermore, it has not been found so far that the sequence of registration No. AC025833 encodes a β1,3-N-acetylglucosaminyltransferase (G6 polypeptide).

INDUSTRIAL APPLICABILITY

The present invention provides a novel polypeptide having β1,3-N-acetylglucosaminyltransferase activity; a process for producing the polypeptide; a DNA encoding the polypeptide; a recombinant vector containing the DNA; a transformant carrying the recombinant vector; an antibody which recognizes the polypeptide; a determination method and an immunostaining method of the polypeptide of the present invention which use the antibody; a process using the polypeptide for producing a sugar chain having GlcNAcβ1-3Gal structure, a poly-N-acetyllactosamine sugar chain and a complex carbohydrate containing the above sugar chains; a process using a transformant carrying the recombinant vector for producing a sugar chain having a GlcNAcβ1-3Gal structure, a poly-N-acetyllactosamine sugar chain and a complex carbohydrate containing the above sugar chains; a method for screening a substance which changes expression of a gene encoding the polypeptide; a method for screening a substance which changes β1,3-N-acetylglucosaminyltransferase activity of the polypeptide; a method using the DNA or the antibody for diagnosing inflammatory diseases and cancers (colon cancer, pancreatic cancer, gastric cancer and the like); and a method using the DNA for treating inflammatory diseases and cancers (colon cancer, pancreatic cancer, gastric cancer and the like), a substance capable of changing expression of a gene encoding the polypeptide or a substance capable of changing β1,3-N-acetylglucosaminyltransferase activity of the polypeptide.

FREE TEXT IN SEQUENCE LISTING

SEQ ID NO:4—Synthetic DNA
SEQ ID NO:5—Synthetic DNA
SEQ ID NO:6—Synthetic DNA
SEQ ID NO:7—Synthetic DNA
SEQ ID NO:8—Synthetic DNA
SEQ ID NO:9—Synthetic DNA
SEQ ID NO:10—Synthetic DNA
SEQ ID NO:11—Synthetic DNA
SEQ ID NO:12—Synthetic DNA
SEQ ID NO:13—Amino acid sequence of FLAG peptide
SEQ ID NO:14—Synthetic DNA
SEQ ID NO:15—Synthetic DNA
SEQ ID NO:16—Synthetic DNA
SEQ ID NO:17—Synthetic DNA
SEQ ID NO:18—Synthetic DNA
SEQ ID NO:19—Synthetic DNA
SEQ ID NO:20—Synthetic DNA
SEQ ID NO:21—Synthetic DNA
SEQ ID NO:22—Synthetic DNA
SEQ ID NO:23—Synthetic DNA
SEQ ID NO:24—Synthetic DNA
SEQ ID NO:25—Synthetic DNA
SEQ ID NO:26—Synthetic DNA
SEQ ID NO:28—Synthetic DNA
SEQ ID NO:29—Synthetic DNA
SEQ ID NO:31—Synthetic DNA

The invention claimed is:

1. A method for producing a cell having increased activity of a beta 1,3-N-acetylglucosaminyltransferase, which comprises the steps of:

introducing DNA or RNA into a cell to express a polypeptide encoded by the DNA or RNA, wherein said DNA or RNA is selected from the group consisting of the following (a) to (g):

(a) a DNA encoding a polypeptide comprising the amino acid sequence of SEQ ID NO:1 and having a beta 1,3-N-acetylglucosaminyltransferase activity, (b) a DNA encoding a polypeptide comprising an amino acid sequence of positions 39-378 in the amino acid sequence of SEQ ID NO:1 and having a beta 1,3-N-acetylglucosaminyltransferase activity, (c) a DNA encoding a polypeptide comprising an amino acid sequence having 95% or more homology with the amino acid sequence in the polypeptide according to (a) or (b), and having a beta 1,3-N-acetylglucosaminyltransferase activity, (d) a DNA comprising the nucleotide sequence of SEQ ID NO:2 and encoding a polypeptide having a beta 1,3-N-acetylglucosaminyltransferase activity, (e) a DNA comprising the nucleotide sequence of positions 135 to 1268 of SEQ ID NO:2 and encoding a polypeptide having a beta 1,3-N-acetylglucosaminyltransferase activity, (f) a DNA comprising the nucleotide sequence of positions 249 to 1268 of SEQ ID NO:2 and encoding a polypeptide having a beta 1,3-N-acetylglucosaminyltransferase activity, and (g) an RNA comprising a sequence corresponding to the DNA selected from any one of (a) to (g); and culturing the cells in order to express said polypeptide.

2. A method for producing a cell having increased amount of a poly-N-acetyllactosamine sugar chain, a lacto-series glycolipid (a glycolipid having Galβ1-3GlcNAcβ1-3Galβ1-4Glc-ceramide as a backbone) or a neolacto-series glycolipid (a glycolipid having Galβ1-4GlcNAcβ1-3Galβ1-4-ceramide as a backbone), which comprises the steps of:

introducing DNA or RNA into a cell to express a polypeptide encoded by the DNA or RNA, wherein said DNA or RNA is selected from the group consisting of the following (a) to (g):

(a) a DNA encoding a polypeptide comprising the amino acid sequence of SEQ ID NO:1 and having a beta 1,3-N-acetylglucosaminyltransferase activity, (b) a DNA encoding a polypeptide comprising an amino acid sequence of positions 39-378 in the amino acid sequence of SEQ ID NO:1 and having a beta 1,3-N-acetylglucosaminyltransferase activity, (c) a DNA encoding a polypeptide comprising an amino acid sequence having 95% or more homology with the amino acid sequence in the polypeptide according to (a) or (b), and having a beta 1,3-N-acetylglucosaminyltransferase activity, (d) a DNA comprising the nucleotide sequence of SEQ ID NO:2 and encoding a polypeptide having a beta 1,3-N-acetylglucosaminyltransferase activity, (e) a DNA comprising the nucleotide sequence of positions 135 to 1268 of SEQ ID NO:2 and encoding a polypeptide having a beta 1,3-N-acetylglucosaminyltransferase activity, (f) a DNA comprising the nucleotide sequence of positions 249 to 1268 of SEQ ID NO:2 and encoding a polypeptide having a beta 1,3-N-acetylglucosaminyltransferase activity, and (g) an RNA comprising a sequence corresponding to the DNA selected from any one of (a) to (g); and culturing the cells in order to express said polypeptide.

3. The method according to any one of claims 1 or 2, wherein the cell is derived from human, non-human animal, plant, insect or microorganism.

4. The method according to any one of claims 1 or 2, wherein the cell is a blood cell, a bone marrow cell, a nerve cell, a stem cell, a cancer cell, a Namalwa cell or a derivative of Namalwa cell.

5. The method according to claim 3, wherein the non-human animal is a mouse.

* * * * *

UNITED STATES PATENT AND TRADEMARK OFFICE
CERTIFICATE OF CORRECTION

PATENT NO. : 7,629,150 B2
APPLICATION NO. : 11/837804
DATED : December 8, 2009
INVENTOR(S) : Narimatsu et al.

It is certified that error appears in the above-identified patent and that said Letters Patent is hereby corrected as shown below:

COLUMN 7:

Line 9, "Glycobiology, 6, 65 (1996), *Glycobiology*, 1, 453 (1997);" should read
      --*Glycobiology*, 6, 65 (1996), *Glycobiology*, 7, 453 (1997);--; and
    Line 31, "*Lysosome*" should read --Lysosome--.

COLUMN 10:

Line 53, "Glcnac)" should read --GlcNac)--.

COLUMN 12:

Line 16, "continuos" should read --continuous--.

COLUMN 14:

Line 61, "reveled" should read --revealed--.

COLUMN 18:

Line 62, "continuos" should read --continuous--.

COLUMN 19:

Line 9, "derivative" should read --derivatives--; and
    Line 22, "2'-propylribose," should read --2'-O-propylribose,--.

COLUMN 20:

Line 64, "penp promoter." should read --penP promoter.--.

COLUMN 22:

Line 58, "express of" should read --express--; and
    Line 63, "bacurovirus" should read --baculovirus--.

COLUMN 23:

Line 2, "(*Bacurovirus*" should read --(*Baculovirus*--; and
    Line 8, "bacurovirus" should read --baculovirus--.

COLUMN 26:

Line 61, "a in vitro" should read --an in vitro--.

COLUMN 27:

Line 6, "manufactures," should read --manufacturers,--.

COLUMN 29:

Line 11, "manufacture's" should read --manufacturer's--.

COLUMN 31:

Line 38, "suppositories" should read --suppositories,--.

COLUMN 38:

Line 59, "continues" should read --continuous--; and
Line 62, "continues" should read --continuous--.

COLUMN 39:

Line 32, "[*Trends in Genetics*, 1, 314-317 (1991)]" should read --[*Trends in Genetics*, 7, 314-317 (1991)]--.

COLUMN 41:

Line 51, "able" should read --possible--.

COLUMN 42:

Line 16, "heterogeneous" should read --heteroduplex--; and
Line 48, "heteroduplexs" should read --heteroduplexes--.

COLUMN 43:

Line 46, "5-end" should read --5'-end--.

COLUMN 44:

Line 25, "The John Hopkins University Press," should read --The Johns Hopkins University Press,--.

COLUMN 45:

Line 39, "one-to two-" should read --one- to two- --.

COLUMN 46:

Line 45, "108 antibody" should read --$10^8$ antibody--.

COLUMN 49:

Line 34, "involved" should read --is involved--.

COLUMN 50:

Line 67, "vies" should read --virus--.

COLUMN 52:

Line 28, "selecting," should read --selection,--.

COLUMN 55:

Line 12, "healthy" should read --health--.

COLUMN 56:

Line 59, "cells cancer" should read --cells, cancer--;
Line 64, "in" should be deleted; and
Line 65, "descriptions" should read --description--.

COLUMN 57:

Line 14, "FIG. 3" should read --FIG. 3A--;
Line 17, "B" should read --FIG. 3B--;
Line 23, "FIG. 4" should read --FIG. 4A--; and
Line 26, "B" should read --FIG. 4B--.

COLUMN 59:

Line 59, "mmol/" should be deleted; and
Line 60, "12-mercaptoethanol" should read --mmol/1 2-mercaptoethanol--.

COLUMN 61:

Line 3, "Of" should read --of--; and
Line 51, "manufacture's" should read --manufacturer's--.

COLUMN 62:

Line 38, "or" should read --for--.

CERTIFICATE OF CORRECTION (continued)
U.S. Pat. No. 7,629,150 B2

COLUMN 68:

Line 7, "manufacture's" should read --manufacturer's--;
    Line 27, "manufacture's" should read --manufacturer's--; and
    Line 45, "manufacture's" should read --manufacturer's--.

COLUMN 71:

Line 1, "Manufactured" should read --manufactured--; and
    Line 47, "inserted" should read --inserting--.

COLUMN 72:

Line 1, "manufacture's" should read --manufacturer's--; and
    Line 18, "manufacture's" should read --manufacturer's--.

COLUMN 73:

Line 55, "4001" should read --400 μl--.

COLUMN 74:

Line 31, "to adhesion" should read --to adhere--.

COLUMN 75:

Line 3, "carried." should read --carried out.--;
    Line 6, "manufacture's" should read --manufacturer's--; and
    Line 10, "manufacture's" should read --manufacturer's--.

COLUMN 76:

Line 50, "manufacture's" should read --manufacturer's--;
    Line 56, "$\mu$mol/" should be deleted; and
    Line 57, "12-aminobenzamide-labeled" should read --$\mu$mol/1 2aminobenzamide-labeled--.

COLUMN 77:

Line 10, "manufacture's" should read --manufacturer's--.

COLUMN 78:

Line 13, "G6sec1-adsorbed" (second occurrence) should read --G6sec2-adsorbed--.

CERTIFICATE OF CORRECTION (continued)
U.S. Pat. No. 7,629,150 B2

COLUMN 80:

Line 12, "101" should read --10μl--.

COLUMN 81:

Line 57, "gel60:" should read --gel 60:--.

COLUMN 82:

Line 43, "B" should read --FIG. 4B--.

COLUMN 83:

Line 63, "health" should read --healthy--.

COLUMN 113:

Line 46, "(a) to (g);" should read --(a) to (f);--; and
Line 52, "Galβ1-4GlcNAcβ1-3Galβ1-4-ceramide" should read
--Galβ1-4GlcNAcβ1-3Galβ1-4Glc-ceramide--.

COLUMN 114:

Line 42, "(a) to (g);" should read --(a) to (f);--.

Signed and Sealed this

Sixteenth Day of March, 2010

David J. Kappos
*Director of the United States Patent and Trademark Office*

SEQUENCE LISTING

<160> NUMBER OF SEQ ID NOS: 32

<210> SEQ ID NO 1
<211> LENGTH: 378
<212> TYPE: PRT
<213> ORGANISM: Homo sapiens

<400> SEQUENCE: 1

```
Met Arg Met Leu Val Ser Gly Arg Arg Val Lys Lys Trp Gln Leu Ile
 1               5                  10                  15

Ile Gln Leu Phe Ala Thr Cys Phe Leu Ala Ser Leu Met Phe Phe Trp
                20                  25                  30

Glu Pro Ile Asp Asn His Ile Val Ser His Met Lys Ser Tyr Ser Tyr
            35                  40                  45

Arg Tyr Leu Ile Asn Ser Tyr Asp Phe Val Asn Asp Thr Leu Ser Leu
        50                  55                  60

Lys His Thr Ser Ala Gly Pro Arg Tyr Gln Tyr Leu Ile Asn His Lys
 65                  70                  75                  80

Glu Lys Cys Gln Ala Gln Asp Val Leu Leu Leu Phe Val Lys Thr
                85                  90                  95

Ala Pro Glu Asn Tyr Asp Arg Arg Ser Gly Ile Arg Arg Thr Trp Gly
            100                 105                 110

Asn Glu Asn Tyr Val Arg Ser Gln Leu Asn Ala Asn Ile Lys Thr Leu
        115                 120                 125

Phe Ala Leu Gly Thr Pro Asn Pro Leu Glu Gly Glu Glu Leu Gln Arg
    130                 135                 140

Lys Leu Ala Trp Glu Asp Gln Arg Tyr Asn Asp Ile Ile Gln Asp
145                 150                 155                 160

Phe Val Asp Ser Phe Tyr Asn Leu Thr Leu Lys Leu Met Gln Phe
                165                 170                 175

Ser Trp Ala Asn Thr Tyr Cys Pro His Ala Lys Phe Leu Met Thr Ala
            180                 185                 190

Asp Asp Asp Ile Phe Ile His Met Pro Asn Leu Ile Glu Tyr Leu Gln
        195                 200                 205

Ser Leu Glu Gln Ile Gly Val Gln Asp Phe Trp Ile Gly Arg Val His
    210                 215                 220

Arg Gly Ala Pro Pro Ile Arg Asp Lys Ser Ser Lys Tyr Tyr Val Ser
225                 230                 235                 240

Tyr Glu Met Tyr Gln Trp Pro Ala Tyr Pro Asp Tyr Thr Ala Gly Ala
                245                 250                 255

Ala Tyr Val Ile Ser Gly Asp Val Ala Ala Lys Val Tyr Glu Ala Ser
            260                 265                 270

Gln Thr Leu Asn Ser Ser Leu Tyr Ile Asp Asp Val Phe Met Gly Leu
        275                 280                 285

Cys Ala Asn Lys Ile Gly Ile Val Pro Gln Asp His Val Phe Phe Ser
    290                 295                 300

Gly Glu Gly Lys Thr Pro Tyr His Pro Cys Ile Tyr Glu Lys Met Met
305                 310                 315                 320

Thr Ser His Gly His Leu Glu Asp Leu Gln Asp Leu Trp Lys Asn Ala
                325                 330                 335

Thr Asp Pro Lys Val Lys Thr Ile Ser Lys Gly Phe Phe Gly Gln Ile
            340                 345                 350

Tyr Cys Arg Leu Met Lys Ile Ile Leu Leu Cys Lys Ile Ser Tyr Val
```

```
                355                 360                 365
Asp Thr Tyr Pro Cys Arg Ala Ala Phe Ile
    370                 375

<210> SEQ ID NO 2
<211> LENGTH: 3750
<212> TYPE: DNA
<213> ORGANISM: Homo sapiens
<220> FEATURE:
<221> NAME/KEY: CDS
<222> LOCATION: (135)..(1271)

<400> SEQUENCE: 2
aagaagactt ccatttttaa tgaccaacat gtattaagat ggacacctac tctacgaaac      60
acgaagttct atggtctcga agaagcccgt gcctgtttaa aactgatcct aactaaaaac     120
agacttgagt ggat atg aga atg ttg gtt agt ggc aga aga gtc aaa aaa       170
             Met Arg Met Leu Val Ser Gly Arg Arg Val Lys Lys
               1               5                  10 tgg cag tta att att cag tta ttt gct act tgt ttt tta gcg agc ctc       218
Trp Gln Leu Ile Ile Gln Leu Phe Ala Thr Cys Phe Leu Ala Ser Leu
         15                  20                  25 atg ttt ttt tgg gaa cca atc gat aat cac att gtg agc cat atg aag       266
Met Phe Phe Trp Glu Pro Ile Asp Asn His Ile Val Ser His Met Lys
     30                  35                  40 tca tat tct tac aga tac ctc ata aat agc tat gac ttt gtg aat gat       314
Ser Tyr Ser Tyr Arg Tyr Leu Ile Asn Ser Tyr Asp Phe Val Asn Asp
 45                  50                  55                  60 acc ctg tct ctt aag cac acc tca gcg ggg cct cgc tac caa tac ttg       362
Thr Leu Ser Leu Lys His Thr Ser Ala Gly Pro Arg Tyr Gln Tyr Leu
                 65                  70                  75 att aac cac aag gaa aag tgt caa gct caa gac gtc ctc ctt tta ctg       410
Ile Asn His Lys Glu Lys Cys Gln Ala Gln Asp Val Leu Leu Leu Leu
             80                  85                  90 ttt gta aaa act gct cct gaa aac tat gat cga cgt tcc gga att aga       458
Phe Val Lys Thr Ala Pro Glu Asn Tyr Asp Arg Arg Ser Gly Ile Arg
         95                 100                 105 agg acg tgg ggc aat gaa aat tat gtt cgg tct cag ctg aat gcc aac       506
Arg Thr Trp Gly Asn Glu Asn Tyr Val Arg Ser Gln Leu Asn Ala Asn
    110                 115                 120 atc aaa act ctg ttt gcc tta gga act cct aat cca ctg gag gga gaa       554
Ile Lys Thr Leu Phe Ala Leu Gly Thr Pro Asn Pro Leu Glu Gly Glu
125                 130                 135                 140 gaa cta caa aga aaa ctg gct tgg gaa gat caa agg tac aat gat ata       602
Glu Leu Gln Arg Lys Leu Ala Trp Glu Asp Gln Arg Tyr Asn Asp Ile
                145                 150                 155 att cag caa gac ttt gtt gat tct ttc tac aat ctt act ctg aaa tta       650
Ile Gln Gln Asp Phe Val Asp Ser Phe Tyr Asn Leu Thr Leu Lys Leu
            160                 165                 170 ctt atg cag ttc agt tgg gca aat acc tat tgt cca cat gcc aaa ttt       698
Leu Met Gln Phe Ser Trp Ala Asn Thr Tyr Cys Pro His Ala Lys Phe
        175                 180                 185 ctt atg act gct gat gat gac ata ttt att cac atg cca aat ctg att       746
Leu Met Thr Ala Asp Asp Asp Ile Phe Ile His Met Pro Asn Leu Ile
    190                 195                 200 gag tac ctt caa agt tta gaa caa att ggt gtt caa gac ttt tgg att       794
Glu Tyr Leu Gln Ser Leu Glu Gln Ile Gly Val Gln Asp Phe Trp Ile
205                 210                 215                 220 ggt cgt gtt cat cgt ggt gcc cct ccc att aga gat aaa agc agc aaa       842
Gly Arg Val His Arg Gly Ala Pro Pro Ile Arg Asp Lys Ser Ser Lys
                225                 230                 235
```

```
tac tac gtg tcc tat gaa atg tac cag tgg cca gct tac cct gac tac         890
Tyr Tyr Val Ser Tyr Glu Met Tyr Gln Trp Pro Ala Tyr Pro Asp Tyr
            240                 245                 250 aca gcc gga gct gcc tat gta atc tcc ggt gat gta gct gcc aaa gtc         938
Thr Ala Gly Ala Ala Tyr Val Ile Ser Gly Asp Val Ala Ala Lys Val
            255                 260                 265 tat gag gca tca cag aca cta aat tca agt ctt tac ata gac gat gtg         986
Tyr Glu Ala Ser Gln Thr Leu Asn Ser Ser Leu Tyr Ile Asp Asp Val
        270                 275                 280 ttc atg ggc ctc tgt gcc aat aaa ata ggg ata gta ccg cag gac cat        1034
Phe Met Gly Leu Cys Ala Asn Lys Ile Gly Ile Val Pro Gln Asp His
285                 290                 295                 300 gtg ttt ttt tct gga gag ggt aaa act cct tat cat ccc tgc atc tat        1082
Val Phe Phe Ser Gly Glu Gly Lys Thr Pro Tyr His Pro Cys Ile Tyr
                305                 310                 315 gaa aaa atg atg aca tct cat gga cac tta gaa gat ctc cag gac ctt        1130
Glu Lys Met Met Thr Ser His Gly His Leu Glu Asp Leu Gln Asp Leu
                320                 325                 330 tgg aag aat gct aca gat cct aaa gta aaa acc att tcc aaa ggt ttt        1178
Trp Lys Asn Ala Thr Asp Pro Lys Val Lys Thr Ile Ser Lys Gly Phe
            335                 340                 345 ttt ggt caa ata tac tgc aga tta atg aag ata att ctc ctt tgt aaa        1226
Phe Gly Gln Ile Tyr Cys Arg Leu Met Lys Ile Ile Leu Leu Cys Lys
        350                 355                 360 att agc tat gtg gac aca tac cct tgt agg gct gcg ttt atc taa            1271
Ile Ser Tyr Val Asp Thr Tyr Pro Cys Arg Ala Ala Phe Ile
365                 370                 375 tagtacttga atgttgtatg ttttcactgt cactgagtca aacctggatg aaaaaaacct      1331
ttaaatgttc gtctataccc taagtaaaat gaggacgaaa gacaaatatt ttgaaagcct      1391
agtccatcag aatgtttctt tgattctaga agctgtttaa tatcacttat ctacttcatt     1451
gcctaagttc atttcaaaga atttgtattt agaaaaggtt tatattatta gtgaaaacaa     1511
aactaaaggg aagttcaagt tctcatgtaa tgccacatat atacttgagg tgtagagatg     1571
ttattaagaa gttttgatgt tagaataatt gcttttggaa ataccaaat gaacgtacag      1631 tacaacattt caaggaaatg aatatattgt tagaccaggt aagcaagttt attttttgtta   1691 aagagcactt ggtggaggta gtaggggcag ggaaaggtca gcataggaga gaaagttcat     1751
gaatctggta aaacagtctc ttgttcttaa gaggagatgt agaaaaatgt gtacaatgtt     1811
attataaaca gacaaatcac gtcttaccac atccatgtag ctactggtgt tagagtcatt    1871
aaaatacctt ttttttgcatc tttttttcaaa gtttaatgtg aactttttaga aaagtgatta   1931 atgttgccct aatactttat atgttttttaa tggattttttt tttaagtatt agaaaatgac   1991
acataacacg ggcagctggt tgctcatagg gtccttctct agggagaaac cattgttaat     2051
tcaaataagc tgattttaat gacgttttca actggttttt aaatattcaa tattggtctg    2111
tgtttaagtt tgttatttga atgtaattta catagaggaa tataataatg gagagacttc     2171
aaatggaaag acagaacatt acaagcctaa tgtctccata attttataaa atgaaatctt     2231
agtgtctaaa tccttgtact gattactaaa attaacccac tcctcccaa caaggtctta      2291 taaaccacag cactttgttc caagttcaga gttttaaatt gagagcatta aacatcaaag     2351
ttataatatc taaaacaatt tattttttcat caataactgt cagaggtgat ctttatttttc    2411 taaatatttc aaacttgaaa acagagtaaa aaagtgatag aaaagttgcc agtttggggt     2471
taaagcattt ttaaagctgc atgttccttg taatcaaaga gatgtgtctg agatctaata    2531
```

```
gagtaagtta catttatttt acaaagcagg ataaaaatgt ggctataata cacactacct    2591
cccttcacta cagaaagaac taggtggtgt ctactgctag ggagattata tgaaggccaa    2651
aataatgact tcagcaagag tgactgaact cactctaagg cctttgactg cagaggcacc    2711
tgttagggaa aatcagatgt ctcatataat aaggtgatgt cggaaacacg caaaacaaaa    2771
cgaaaaaaga tttctcagta tacacaactg aatgatgata cttacaattt ttagcaggta    2831 gcttttaat gttacagaa attttaattt ttttctattt tgaaatttga ggcttgttta     2891
cattgcttag ataatttaga attttttaact aatgtcaaaa ctacagtgtc aaacattcta   2951
ggttgtagtt actttcagag tagatacagg gttttagatc attacagttt aagttttctg   3011
accaattaaa aaaacataga gaacaaaagc atatttgacc aagcaacaag cttataatta   3071 attttttatta gttgattgat taatgatgta ttgccttttg cccatatata ccctgtgtat  3131
ctatacttgg aagtgtttaa ggttgccatt ggttgaaaac ataagtgtct ctggccatca   3191
aagtgatctt gttacagca gtgcttttgt gaaacaatta tttatttgct gaaagagctc    3251
ttctgaactg tgtccttta attttgctt agaatagaat ggaacaagtt taaatttcaa     3311
ggaaatatga aggcacttcc ttttttcta agaaggaagt tgctagatga ttccttcatc    3371
acacttactt aaagtactga aagagtatc tgtaaataaa agggttccaa cctttaaaa    3431 aagaaggaaa aaacttttg gtgctccagt gtagggctat cttttaaaa aatgtcaaca    3491 aagggaaaat taactatcag cttggatggt cacttgaata aagatggtt atacacagtg   3551 ttattgttaa aattttttta cctttggtt ggtttgcatc ttttttccat attgttaatt   3611
ttataccaaa atgttaaata tttgtattac ttgaattttg ctcttgtatg gcaaaataat  3671
tagtgagttt aaaaaaaatc tatagtttcc aataaacaac tgaaaatta aaaaaaaaa    3731 aaaaaaaaaa aaaaaaaaa                                                 3750
```

```
<210> SEQ ID NO 3
<211> LENGTH: 738
<212> TYPE: DNA
<213> ORGANISM: Rattus norvegicus
<220> FEATURE:
<221> NAME/KEY: CDS
<222> LOCATION: (1)..(738)

<400> SEQUENCE: 3 c tac gag cga cgt tct gcc atc aga aag acg tgg ggc aac gag aat tac    49
  Tyr Glu Arg Arg Ser Ala Ile Arg Lys Thr Trp Gly Asn Glu Asn Tyr
  1               5                  10                  15 gtc cag tct cag ctc aac gcc aac atc aaa att ctg ttc gcg tta gga     97
Val Gln Ser Gln Leu Asn Ala Asn Ile Lys Ile Leu Phe Ala Leu Gly
             20                  25                  30 act cct cat cca ctg aag gga aaa gag ctg caa aaa aga ctg att tgg    145
Thr Pro His Pro Leu Lys Gly Lys Glu Leu Gln Lys Arg Leu Ile Trp
         35                  40                  45 gaa gat caa gtg tac cac gac ata att cag caa gat ttc act gat tct    193
Glu Asp Gln Val Tyr His Asp Ile Ile Gln Gln Asp Phe Thr Asp Ser
     50                  55                  60 ttc cac aat ctt act ttt aaa ttt ctt ctt cag ttc ggc tgg gca aac    241
Phe His Asn Leu Thr Phe Lys Phe Leu Leu Gln Phe Gly Trp Ala Asn
65                  70                  75                  80 acc ttt tgc cca cat gcc aga ttc ctg atg act gct gat gat gac ata    289
Thr Phe Cys Pro His Ala Arg Phe Leu Met Thr Ala Asp Asp Asp Ile
                 85                  90                  95 ttt atc cac atg cca aat ctc att gaa tac ctt caa ggg ctg gag cag    337
Phe Ile His Met Pro Asn Leu Ile Glu Tyr Leu Gln Gly Leu Glu Gln
```

```
                    Phe Ile His Met Pro Asn Leu Ile Glu Tyr Leu Gln Gly Leu Glu Gln
                                    100                 105                 110 gtt gga gtt cga gac ttt tgg att ggt cac gtt cac cga ggg ggc cct                385
Val Gly Val Arg Asp Phe Trp Ile Gly His Val His Arg Gly Gly Pro
            115                 120                 125 cct gtt aga gac aaa agt agc aag tac tat gtt ccc tat gaa atg tac                433
Pro Val Arg Asp Lys Ser Ser Lys Tyr Tyr Val Pro Tyr Glu Met Tyr
130                 135                 140 aag tgg cca gcc tac cct gac tat acc gcc ggt gct gcc tat gtc gtc                481
Lys Trp Pro Ala Tyr Pro Asp Tyr Thr Ala Gly Ala Ala Tyr Val Val
145                 150                 155                 160 tcc aac gat gta gct gcc aaa atc tat gag gca tca cag acg ctg aat                529
Ser Asn Asp Val Ala Ala Lys Ile Tyr Glu Ala Ser Gln Thr Leu Asn
                165                 170                 175 tcc agc atg tac ata gac gat gtg ttc atg ggc ctc tgc gcc aat aaa                577
Ser Ser Met Tyr Ile Asp Asp Val Phe Met Gly Leu Cys Ala Asn Lys
            180                 185                 190 gtg ggg gtc gtg cca cag gac cat gta ttt ttc tct ggg gaa ggg aag                625
Val Gly Val Val Pro Gln Asp His Val Phe Phe Ser Gly Glu Gly Lys
        195                 200                 205 att cct tac cat ccc tgc atc tat gaa aag atg ata acg tct cat gga                673
Ile Pro Tyr His Pro Cys Ile Tyr Glu Lys Met Ile Thr Ser His Gly
    210                 215                 220 cac tca caa gac cta cag gac ctc tgg gtg gag gcc aca gat cct aaa                721
His Ser Gln Asp Leu Gln Asp Leu Trp Val Glu Ala Thr Asp Pro Lys
225                 230                 235                 240 gtg aag gac att tcg aa                                                         738
Val Lys Asp Ile Ser <210> SEQ ID NO 4
<211> LENGTH: 24
<212> TYPE: DNA
<213> ORGANISM: Artificial Sequence
<220> FEATURE:
<223> OTHER INFORMATION: synthetic DNA

<400> SEQUENCE: 4
catcacagac actaaattca agtc                                                     24

<210> SEQ ID NO 5
<211> LENGTH: 24
<212> TYPE: DNA
<213> ORGANISM: Artificial Sequence
<220> FEATURE:
<223> OTHER INFORMATION: synthetic DNA

<400> SEQUENCE: 5
gcagtatatt tgaccaaaaa aacc                                                     24

<210> SEQ ID NO 6
<211> LENGTH: 11
<212> TYPE: DNA
<213> ORGANISM: Artificial Sequence
<220> FEATURE:
<223> OTHER INFORMATION: synthetic DNA

<400> SEQUENCE: 6
ctttagagca c                                                                   11

<210> SEQ ID NO 7
<211> LENGTH: 8
<212> TYPE: DNA
<213> ORGANISM: Artificial Sequence
```

```
<220> FEATURE:
<223> OTHER INFORMATION: synthetic DNA

<400> SEQUENCE: 7 ctctaaag                                                                    8

<210> SEQ ID NO 8
<211> LENGTH: 29
<212> TYPE: DNA
<213> ORGANISM: Artificial Sequence
<220> FEATURE:
<223> OTHER INFORMATION: synthetic DNA

<400> SEQUENCE: 8
ggggtaccat agatgcaggg atgataagg                                            29

<210> SEQ ID NO 9
<211> LENGTH: 32
<212> TYPE: DNA
<213> ORGANISM: Artificial Sequence
<220> FEATURE:
<223> OTHER INFORMATION: synthetic DNA

<400> SEQUENCE: 9
ggggtaccga cttgaattta gtgtctgtga tg                                        32

<210> SEQ ID NO 10
<211> LENGTH: 30
<212> TYPE: DNA
<213> ORGANISM: Artificial Sequence
<220> FEATURE:
<223> OTHER INFORMATION: synthetic DNA

<400> SEQUENCE: 10
ggggtaccat ctgtagcatt cttccaaagg                                           30

<210> SEQ ID NO 11
<211> LENGTH: 32
<212> TYPE: DNA
<213> ORGANISM: Artificial Sequence
<220> FEATURE:
<223> OTHER INFORMATION: synthetic DNA

<400> SEQUENCE: 11
ggaattcccc tactctacga aacacgaagt tc                                        32

<210> SEQ ID NO 12
<211> LENGTH: 32
<212> TYPE: DNA
<213> ORGANISM: Artificial Sequence
<220> FEATURE:
<223> OTHER INFORMATION: synthetic DNA

<400> SEQUENCE: 12
ggaattccct ttcgtcctca ttttacttag gg                                        32

<210> SEQ ID NO 13
<211> LENGTH: 8
<212> TYPE: PRT
<213> ORGANISM: Artificial Sequence
<220> FEATURE:
<223> OTHER INFORMATION: commercially available amino acid sequence

<400> SEQUENCE: 13

Asp Tyr Lys Asp Asp Asp Asp Lys
 1               5
```

<210> SEQ ID NO 14
<211> LENGTH: 39
<212> TYPE: DNA
<213> ORGANISM: Artificial Sequence
<220> FEATURE:
<223> OTHER INFORMATION: synthetic DNA

<400> SEQUENCE: 14
agcttgccgc caccatgcat tttcaagtgc agattttca                                39

<210> SEQ ID NO 15
<211> LENGTH: 39
<212> TYPE: DNA
<213> ORGANISM: Artificial Sequence
<220> FEATURE:
<223> OTHER INFORMATION: synthetic DNA

<400> SEQUENCE: 15
gcttcctgct aatcagtgcc tcagtcataa tgtcacgtg                                39

<210> SEQ ID NO 16
<211> LENGTH: 36
<212> TYPE: DNA
<213> ORGANISM: Artificial Sequence
<220> FEATURE:
<223> OTHER INFORMATION: synthetic DNA

<400> SEQUENCE: 16
gagattacaa ggacgacgat gacaaggcct acgtag                                   36

<210> SEQ ID NO 17
<211> LENGTH: 40
<212> TYPE: DNA
<213> ORGANISM: Artificial Sequence
<220> FEATURE:
<223> OTHER INFORMATION: synthetic DNA

<400> SEQUENCE: 17
gaagctgaaa atctgcactt gaaaatgcat ggtggcggca                               40

<210> SEQ ID NO 18
<211> LENGTH: 39
<212> TYPE: DNA
<213> ORGANISM: Artificial Sequence
<220> FEATURE:
<223> OTHER INFORMATION: synthetic DNA

<400> SEQUENCE: 18
atctccacgt gacattatga ctgaggcact gattagcag                                39

<210> SEQ ID NO 19
<211> LENGTH: 35
<212> TYPE: DNA
<213> ORGANISM: Artificial Sequence
<220> FEATURE:
<223> OTHER INFORMATION: synthetic DNA

<400> SEQUENCE: 19
gtacctacgt aggccttgtc atcgtcgtcc ttgta                                    35

<210> SEQ ID NO 20
<211> LENGTH: 30
<212> TYPE: DNA
<213> ORGANISM: Artificial Sequence
<220> FEATURE:

<223> OTHER INFORMATION: Synthetic DNA

<400> SEQUENCE: 20
cgcggatcct ccccacggtc cgtggaccag        30

<210> SEQ ID NO 21
<211> LENGTH: 36
<212> TYPE: DNA
<213> ORGANISM: Artificial Sequence
<220> FEATURE:
<223> OTHER INFORMATION: Synthetic DNA

<400> SEQUENCE: 21
atagtttagc ggccgcggaa gggctcagca gcgtcg        36

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22
cgggatccga taatcacatt gtgagccata tg        32

<210> SEQ ID NO 23
<211> LENGTH: 32
<212> TYPE: DNA
<213> ORGANISM: Artificial Sequence
<220> FEATURE:
<223> OTHER INFORMATION: Synthetic DNA

<400> SEQUENCE: 23
gctctagatg acagtgaaaa catacaacat tc        32

<210> SEQ ID NO 24
<211> LENGTH: 32
<212> TYPE: DNA
<213> ORGANISM: Artificial Sequence
<220> FEATURE:
<223> OTHER INFORMATION: Synthetic DNA

<400> SEQUENCE: 24
cgggatccat tgtgagccat atgaagtcat at        32

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA

<400> SEQUENCE: 25
tcttatgact gctgatgatg acat        24

<210> SEQ ID NO 26
<211> LENGTH: 13
<212> TYPE: DNA
<213> ORGANISM: Artificial Sequence
<220> FEATURE:
<223> OTHER INFORMATION: synthetic DNA

<400> SEQUENCE: 26
gatcatcgcg aga        13

```
<210> SEQ ID NO 27
<211> LENGTH: 13
<212> TYPE: DNA
<213> ORGANISM: Artificial Sequence
<220> FEATURE:
<223> OTHER INFORMATION: synthetic DNA

<400> SEQUENCE: 27
agcttctcgc gat                                                          13

<210> SEQ ID NO 28
<211> LENGTH: 24
<212> TYPE: DNA
<213> ORGANISM: Artificial Sequence
<220> FEATURE:
<223> OTHER INFORMATION: synthetic DNA

<400> SEQUENCE: 28
ctttaggatc tgtagcattc ttcc                                              24

<210> SEQ ID NO 29
<211> LENGTH: 24
<212> TYPE: DNA
<213> ORGANISM: Artificial Sequence
<220> FEATURE:
<223> OTHER INFORMATION: synthetic DNA

<400> SEQUENCE: 29
gatatcgccg cgctcgtcgt cgac                                              24

<210> SEQ ID NO 30
<211> LENGTH: 4419
<212> TYPE: DNA
<213> ORGANISM: Homo sapiens
<220> FEATURE:
<221> NAME/KEY: promoter
<222> LOCATION: (1)..(652)
<220> FEATURE:
<221> NAME/KEY: exon
<222> LOCATION: (653)..(4373)
<220> FEATURE:
<221> NAME/KEY: CDS
<222> LOCATION: (787)..(1923)

<400> SEQUENCE: 30
ttaaaaaaaa agaaaaaaga agtcttactc ttattcctgc cttgtctggg gcaagcctta        60
atggattttt actgctgtga attttctttt cattgaagat tttgccttga tctatgtatc       120
tgctttcatc ctgaccatat tcaagtcagt atattcatga atgtacctgt ttgtgaaatt       180
tgaacttaag tatacacgat tatagccgtt tgggaagctt ttttttttt ttttttaaga        240 gtaggagtag aaaaaggtct ctgtactctg aatgggaaga cagtgtaaag caattttttc       300
ccttttcctg tcctccttta aaaaaataa acagccgtat gcctctgcta agtactaact        360
acctcatcac cttttgtgca gacagggcag gttacatttg gttttaagga attaggaata       420
tgtttctttc cagcacctta gtaacccacg cgattgtgat tcttttctct tcttgactgt       480
gataggtggc atgaatatt cacatgggag agccgcatga ggccgcccac cacgcttcct        540
gaaggatgcc cgtgtggaag aattttgacg tgccagtgtc ctcgttctac agggtgttcc       600
attcttccgc aatctcagaa aaatgggact aaaagaaact attttgtaaa ataagaagac       660 ttccatttt aatgaccaac atgtattaag atggacacct actctacgaa acacgaagtt        720
ctatggtctc gaagaagccc gtgcctgttt aaaactgatc ctaactaaaa acagacttga       780 gtggat atg aga atg ttg gtt agt ggc aga aga gtc aaa aaa tgg cag          828
```

```
            Met Arg Met Leu Val Ser Gly Arg Arg Val Lys Lys Trp Gln
              1               5                  10 tta att att cag tta ttt gct act tgt ttt tta gcg agc ctc atg ttt       876
Leu Ile Ile Gln Leu Phe Ala Thr Cys Phe Leu Ala Ser Leu Met Phe
 15              20                  25                  30 ttt tgg gaa cca atc gat aat cac att gtg agc cat atg aag tca tat       924
Phe Trp Glu Pro Ile Asp Asn His Ile Val Ser His Met Lys Ser Tyr
                 35                  40                  45 tct tac aga tac ctc ata aat agc tat gac ttt gtg aat gat acc ctg       972
Ser Tyr Arg Tyr Leu Ile Asn Ser Tyr Asp Phe Val Asn Asp Thr Leu
             50                  55                  60 tct ctt aag cac acc tca gcg ggg cct cgc tac caa tac ttg att aac      1020
Ser Leu Lys His Thr Ser Ala Gly Pro Arg Tyr Gln Tyr Leu Ile Asn
 65                  70                  75 cac aag gaa aag tgt caa gct caa gac gtc ctc ctt tta ctg ttt gta      1068
His Lys Glu Lys Cys Gln Ala Gln Asp Val Leu Leu Leu Leu Phe Val
         80                  85                  90 aaa act gct cct gaa aac tat gat cga cgt tcc gga att aga agg acg      1116
Lys Thr Ala Pro Glu Asn Tyr Asp Arg Arg Ser Gly Ile Arg Arg Thr
 95                 100                 105                 110 tgg ggc aat gaa aat tat gtt cgg tct cag ctg aat gcc aac atc aaa      1164
Trp Gly Asn Glu Asn Tyr Val Arg Ser Gln Leu Asn Ala Asn Ile Lys
                115                 120                 125 act ctg ttt gcc tta gga act cct aat cca ctg gag gga gaa gaa cta      1212
Thr Leu Phe Ala Leu Gly Thr Pro Asn Pro Leu Glu Gly Glu Glu Leu
         130                 135                 140 caa aga aaa ctg gct tgg gaa gat caa agg tac aat gat ata att cag      1260
Gln Arg Lys Leu Ala Trp Glu Asp Gln Arg Tyr Asn Asp Ile Ile Gln
             145                 150                 155 caa gac ttt gtt gat tct ttc tac aat ctt act ctg aaa tta ctt atg      1308
Gln Asp Phe Val Asp Ser Phe Tyr Asn Leu Thr Leu Lys Leu Leu Met
         160                 165                 170 cag ttc agt tgg gca aat acc tat tgt cca cat gcc aaa ttt ctt atg      1356
Gln Phe Ser Trp Ala Asn Thr Tyr Cys Pro His Ala Lys Phe Leu Met
175                 180                 185                 190 act gct gat gat gac ata ttt att cac atg cca aat ctg att gag tac      1404
Thr Ala Asp Asp Asp Ile Phe Ile His Met Pro Asn Leu Ile Glu Tyr
                195                 200                 205 ctt caa agt tta gaa caa att ggt gtt caa gac ttt tgg att ggt cgt      1452
Leu Gln Ser Leu Glu Gln Ile Gly Val Gln Asp Phe Trp Ile Gly Arg
         210                 215                 220 gtt cat cgt ggt gcc cct ccc att aga gat aaa agc agc aaa tac tac      1500
Val His Arg Gly Ala Pro Pro Ile Arg Asp Lys Ser Ser Lys Tyr Tyr
             225                 230                 235 gtg tcc tat gaa atg tac cag tgg cca gct tac cct gac tac aca gcc      1548
Val Ser Tyr Glu Met Tyr Gln Trp Pro Ala Tyr Pro Asp Tyr Thr Ala
         240                 245                 250 gga gct gcc tat gta atc tcc ggt gat gta gct gcc aaa gtc tat gag      1596
Gly Ala Ala Tyr Val Ile Ser Gly Asp Val Ala Ala Lys Val Tyr Glu
255                 260                 265                 270 gca tca cag aca cta aat tca agt ctt tac ata gac gat gtg ttc atg      1644
Ala Ser Gln Thr Leu Asn Ser Ser Leu Tyr Ile Asp Asp Val Phe Met
                275                 280                 285 ggc ctc tgt gcc aat aaa ata ggg ata gta ccg cag gac cat gtg ttt      1692
Gly Leu Cys Ala Asn Lys Ile Gly Ile Val Pro Gln Asp His Val Phe
         290                 295                 300 ttt tct gga gag ggt aaa act cct tat cat ccc tgc atc tat gaa aaa      1740
Phe Ser Gly Glu Gly Lys Thr Pro Tyr His Pro Cys Ile Tyr Glu Lys
             305                 310                 315
```

```
atg atg aca tct cat gga cac tta gaa gat ctc cag gac ctt tgg aag    1788
Met Met Thr Ser His Gly His Leu Glu Asp Leu Gln Asp Leu Trp Lys
    320             325                 330 aat gct aca gat cct aaa gta aaa acc att tcc aaa ggt ttt ttt ggt    1836
Asn Ala Thr Asp Pro Lys Val Lys Thr Ile Ser Lys Gly Phe Phe Gly
335                 340                 345                 350 caa ata tac tgc aga tta atg aag ata att ctc ctt tgt aaa att agc    1884
Gln Ile Tyr Cys Arg Leu Met Lys Ile Ile Leu Leu Cys Lys Ile Ser
                355                 360                 365 tat gtg gac aca tac cct tgt agg gct gcg ttt atc taa tagtacttga     1933
Tyr Val Asp Thr Tyr Pro Cys Arg Ala Ala Phe Ile
                370                 375 atgttgtatg ttttcactgt cactgagtca aacctggatg aaaaaaacct taaatgttc   1993
gtctataccc taagtaaaat gaggacgaaa gacaaatatt tgaaagcct  agtccatcag  2053
aatgtttctt tgattctaga agctgtttaa tatcacttat ctacttcatt gcctaagttc  2113
atttcaaaga atttgtattt agaaaaggtt tatattatta gtgaaaacaa actaaaggg   2173
aagttcaagt tctcatgtaa tgccacatat atacttgagg tgtagagatg ttattaagaa  2233
gttttgatgt tagaataatt gcttttggaa aataccaaat gaacgtacag tacaacattt  2293
caaggaaatg aatatattgt tagaccaggt aagcaagttt attttttgtta aagagcactt 2353
ggtggaggta gtaggggcag ggaaaggtca gcataggaga aaagttcat  gaatctggta  2413
aaacagtctc ttgttcttaa gaggagatgt agaaaaatgt gtacaatgtt attataaaca  2473
gacaaatcac gtcttaccac atccatgtag ctactggtgt tagagtcatt aaaatacctt  2533
tttttgcatc tttttttcaaa gtttaatgtg aacttttaga aaagtgatta atgttgccct  2593
aatactttat atgttttttaa tggatttttt tttaagtatt agaaaatgac acataacacg  2653
ggcagctggt tgctcatagg gtccttctct agggagaaac cattgttaat tcaaataagc  2713
tgattttaat gacgttttca actggttttt aaatattcaa tattggtctg tgtttaagtt  2773
tgttatttga atgtaattta catagaggaa tataataatg gagagacttc aaatggaaag  2833
acagaacatt acaagcctaa tgtctccata atttttataaa atgaaatctt agtgtctaaa  2893
tccttgtact gattactaaa attaacccac tcctccccaa caaggtctta taaaccacag  2953
cactttgttc caagttcaga gtttttaaatt gagagcatta acatcaaag  ttataatatc  3013
taaaacaatt tattttttcat caataactgt cagaggtgat ctttattttc taaatatttc  3073
aaacttgaaa acagagtaaa aaagtgatag aaaagttgcc agtttggggt taaagcattt   3133
ttaaagctgc atgttccttg taatcaaaga gatgtgtctg agatctaata gagtaagtta   3193
catttatttt acaaagcagg ataaaaatgt ggctataata cacactacct cccttcacta   3253
cagaaagaac taggtggtgt ctactgctag ggagattata tgaaggccaa aataatgact   3313
tcagcaagag tgactgaact cactctaagg cctttgactg cagaggcacc tgttagggaa   3373
aatcagatgt ctcatataat aaggtgatgt cggaaacacg caaaacaaaa cgaaaaaaga   3433
tttctcagta tacacaactg aatgatgata cttacaattt ttagcaggta gcttttttaat   3493
gtttacagaa attttaattt ttttctattt tgaaatttga ggcttgttta cattgcttag   3553
ataatttaga attttttaact aatgtcaaaa ctacagtgtc aaacattcta ggttgtagtt   3613
actttcagag tagatacagg gttttagatc attacagttt aagttttctg accaattaaa   3673
aaaacataga gaacaaaagc atatttgacc aagcaacaag cttataatta atttttatta   3733
gttgattgat taatgatgta ttgccttttg cccatatata ccctgtgtat ctatacttgg   3793
aagtgtttaa ggttgccatt ggttgaaaac ataagtgtct ctggccatca aagtgatctt   3853
```

-continued

```
gtttacagca gtgcttttgt gaaacaatta tttatttgct gaaagagctc ttctgaactg    3913 tgtccttta atttttgctt agaatagaat ggaacaagtt taaatttcaa ggaaatatga    3973
aggcacttcc ttttttcta agaaggaagt tgctagatga ttccttcatc acacttactt    4033
aaagtactga gaagagtatc tgtaaataaa agggttccaa cctttaaaa agaaggaaa     4093 aaactttttg gtgctccagt gtagggctat ctttttaaaa aatgtcaaca aagggaaat    4153 aaactatcag cttggatggt cacttgaata gaagatggtt atacacagtg ttattgttaa   4213
aattttttta ccttttggtt ggtttgcatc ttttttccat attgttaatt ttataccaaa   4273
atgttaaata tttgtattac ttgaattttg ctcttgtatg gcaaataat tagtgagttt    4333 aaaaaaaatc tatagtttcc aataaacaac tgaaaaatta tcatgagaag ggtatttaaa   4393 cttttttcatg aacattgctt atataa                                        4419
```

<210> SEQ ID NO 31
<211> LENGTH: 24
<212> TYPE: DNA
<213> ORGANISM: Artificial Sequence
<220> FEATURE:
<223> OTHER INFORMATION: synthetic DNA

<400> SEQUENCE: 31
caggaaggaa ggctggaaga gtgc                                           24

<210> SEQ ID NO 32
<211> LENGTH: 245
<212> TYPE: PRT
<213> ORGANISM: Rattus norvegicus

<400> SEQUENCE: 32

Tyr Glu Arg Arg Ser Ala Ile Arg Lys Thr Trp Gly Asn Glu Asn Tyr
 1               5                  10                  15

Val Gln Ser Gln Leu Asn Ala Asn Ile Lys Ile Leu Phe Ala Leu Gly
             20                  25                  30

Thr Pro His Pro Leu Lys Gly Lys Glu Leu Gln Lys Arg Leu Ile Trp
         35                  40                  45

Glu Asp Gln Val Tyr His Asp Ile Ile Gln Asp Phe Thr Asp Ser
     50                  55                  60

Phe His Asn Leu Thr Phe Lys Phe Leu Leu Gln Phe Gly Trp Ala Asn
 65                  70                  75                  80

Thr Phe Cys Pro His Ala Arg Phe Leu Met Thr Ala Asp Asp Ile
                 85                  90                  95

Phe Ile His Met Pro Asn Leu Ile Glu Tyr Leu Gln Gly Leu Glu Gln
            100                 105                 110

Val Gly Val Arg Asp Phe Trp Ile Gly His Val His Arg Gly Gly Pro
        115                 120                 125

Pro Val Arg Asp Lys Ser Ser Lys Tyr Tyr Val Pro Tyr Glu Met Tyr
    130                 135                 140

Lys Trp Pro Ala Tyr Pro Asp Tyr Thr Ala Gly Ala Ala Tyr Val Val
145                 150                 155                 160

Ser Asn Asp Val Ala Ala Lys Ile Tyr Glu Ala Ser Gln Thr Leu Asn
                165                 170                 175

Ser Ser Met Tyr Ile Asp Asp Val Phe Met Gly Leu Cys Ala Asn Lys
            180                 185                 190

Val Gly Val Val Pro Gln Asp His Val Phe Phe Ser Gly Glu Gly Lys

-continued

```
                195                 200                 205
Ile Pro Tyr His Pro Cys Ile Tyr Glu Lys Met Ile Thr Ser His Gly
    210                 215                 220

His Ser Gln Asp Leu Gln Asp Leu Trp Val Glu Ala Thr Asp Pro Lys
225                 230                 235                 240

Val Lys Asp Ile Ser
                245
```